(12) United States Patent
Baty et al.

(10) Patent No.: US 9,512,203 B2
(45) Date of Patent: Dec. 6, 2016

(54) SINGLE-DOMAIN ANTIBODIES THAT BIND TO HIV-1 NEF WITH HIGH AFFINITY

(75) Inventors: Daniel Baty, Marseilles (FR); Martine Jeanne Pierrette Chartier, Marseilles (FR); Patrick Chames, Marseilles (FR); Serge Salomon Benichou, Paris (FR); Stephane Eric Ciogullari, Villemomble (FR); Jerome Christophe Marie Abel Bouchet, Paris (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 727 days.

(21) Appl. No.: 12/734,773

(22) PCT Filed: Nov. 18, 2008

(86) PCT No.: PCT/IB2008/054832
§ 371 (c)(1),
(2), (4) Date: May 21, 2010

(87) PCT Pub. No.: WO2009/066241
PCT Pub. Date: May 28, 2009

(65) Prior Publication Data
US 2013/0330342 A1  Dec. 12, 2013

(30) Foreign Application Priority Data
Nov. 22, 2007 (FR) ...................................... 07 08189

(51) Int. Cl.
| C07K 16/10 | (2006.01) |
| C12N 15/00 | (2006.01) |
| A61K 39/42 | (2006.01) |
| C07K 16/00 | (2006.01) |

(52) U.S. Cl.
CPC ......... *C07K 16/1045* (2013.01); *C07K 16/005* (2013.01); *C07K 2317/22* (2013.01); *C07K 2317/569* (2013.01); *C07K 2317/76* (2013.01); *C07K 2317/92* (2013.01)

(58) Field of Classification Search
CPC ............ C07K 16/1045; C07K 16/005; C07K 2317/76; C07K 2317/569; C07K 2317/22
See application file for complete search history.

(56) References Cited

U.S. PATENT DOCUMENTS

| 6,139,843 A | 10/2000 | Rubinstein et al. | |
| 2006/0246477 A1* | 11/2006 | Hermans et al. | 435/6 |

FOREIGN PATENT DOCUMENTS

FR  2 668 488  4/1992

OTHER PUBLICATIONS

Muyldermans, S., et al., Apr. 2001, Recognition of antigens by single-domain antibody fragments: the superfluous luxury of paired domains, Trends Biochem. Sci. 26(4):230-235.*
Dekker, S., et al., Nov. 2003, Intracellularly expressed single-domain antibody against p15 matrix protein prevents the production of porcine retroviruses, J. Virol. 77(22):12132-12139.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*
Xiang, J., et al., 1995, Framework residues 71 and 93 of the chimeric B72.3 antibody are major determinants of the conformation of heavy-chain hypervariable loops, J. Mol. Biol. 253:385-390.*
Chen, C., et al., Sep. 1992, Generatio and analysis of random point mutations in an antibody CDR2 sequence: many mutated antibodies lose their ability to bind antigen, J. Exp. Med. 176:855-866.*
Choudhry, V., et al., 2006, Antibody-based inhibitors of HIV infection, Expert Opin. Biol. Ther. 6(5):523-531.*
West, Jr., A. P., et al., Oct. 2011, Single-chain Fv-based anti-HIV proteins: potential and limitations, J. Virol. 86(1):195-202.*
Moureau, C., et al., 2000, Specificity of anti-Nef antibodies produced in mice immunized with DNA encoding the HIV-1 nef gene product, Vaccine 18:333-341.*
Forsman, A., et al., Oct. 2008, Llama antibody fragments with cross-subtype human immunodeficiency virus type 1 (HIV-1)-neutralizing properties and high affinity for HIV-1 gp120, J. Virol. 82(24):12069-12081.*
International Search Report for PCT/IB2008/054832, mailed Apr. 9, 2009.
Fujii, Y. et al., "Evidence for the role of human immunodeficiency virus type 1 Nef protein as a growth inhibitor to CD4+ T lymphocytes and for the blocking of the Nef function by anti-Nef antibodies", Vaccine, vol. 11, No. 8, (1993), pp. 837-847.
Silva, F.A. et al., "Camelized Rabbit-derived VH Single-domain Intrabodies Against Vif Strongly Neutralize HIV-1 Infectivity", Journal of Molecular Biology, vol. 340, No. 3, (Jul. 2004), pp. 525-542.
Cazeaux, N. et al., "Comparative study of immune responses induced after immunization with plasmids encoding the HIV-1 Nef protein under the control of the CMV-IE or the muscle-specific desmin promoter", Vaccine, vol. 20, No. 27-28, (Sep. 10, 2002), pp. 3322-3331.

(Continued)

*Primary Examiner* — Jeffrey Parkin
(74) *Attorney, Agent, or Firm* — Young & Thompson

(57) ABSTRACT

The invention relates to antibody fragments with simple heavy chain or sdAbs, characterized in that they consist of anti HIV Nef-protein fragments corresponding to all or a portion of the HHV domains of camelids, particularly llamas.

10 Claims, 10 Drawing Sheets

(56) References Cited

OTHER PUBLICATIONS

Collings, A. et al., "Humoral and cellular immune responses to HIV-1 Nef in mice DNA-immunised with non-replicating or self-replicating expression vectors", Vaccine, vol. 18, (2000), pp. 460-467.

Kawai, M. et al., "Chimeric Human/Murine Monoclonal IgM Antibodies to HIV-1 Nef Antigen Expressed on Chronically Infected Cells", Microbiology and Immunology, vol. 47, No. 3, (2003), pp. 247-253.

* cited by examiner

| sdAb | $k_a \times 10^5$ (1/Ms) | $k_d \times 10^{-4}$ (1/s) | $K_D \times 10^{-9}$ (M) |
|---|---|---|---|
| Nef19P | 0.89 +/- 0.12 | 1.81 +/- 0.04 | 2 |
| Nef19C | 10.6 1 +/- 0.06 | 1.54 +/- 0.04 | 0.14 |

A

B

A

B

SEQUENCE LISTING

```
<160> NUMBER OF SEQ ID NOS: 58

<210> SEQ ID NO 1
<211> LENGTH: 345
<212> TYPE: DNA
<213> ORGANISM: Artificial Sequence
<220> FEATURE:
<223> OTHER INFORMATION: Description of Artificial Sequence: Synthetic
      sdAb Nef19 polynucleotide

<400> SEQUENCE: 1
```

```
gaggtgcagc tggtggagtc tgggggaggc ttggtgcagc ctgggggtc tctgaaactc      60 tcctgtgcag cctctggaag catcttcaga gccaatgcca tgcgctggta ccgccaggct    120
ccaggaaaac agcgcgagtg ggtcgcaagt gttattagtg atgatttcac agactatgta    180
gactctgtga ggggccgatt caccatctcc aaagacaacg cccagaacac ggtgtatctc    240
caaatgaaca gcctgaaacc tgaggacacg gccgtctatt actgtaatgc gaactcggc     300 ggagtcaact actggggcca ggggacccag gtcaccgtct cctca                    345

<210> SEQ ID NO 2
<211> LENGTH: 357
<212> TYPE: DNA
<213> ORGANISM: Artificial Sequence
<220> FEATURE:
<223> OTHER INFORMATION: Description of Artificial Sequence: Synthetic
      sdAb Nef20 polynucleotide

<400> SEQUENCE: 2
gaggtgcagc tggtggagtc tgggggaggc ttggtgcagg ctggagggtc tctgatactc     60
tcctgtgcaa cctctggtag gatcttcggt atcaatgcca tgggctggta ccgccaggct   120
ccagggaagg agcgcgagtt ggtcgcagtt attaccagtg gtggaaacac aaactatgca   180
gactccgtga agggccgatt caccatctcc aaagacaatg ccaagaacac gctgtatctg   240
caaatgaata gcctgaaatt tgaggacacg gcccggtact actgtgtgag atccctccct   300
gggtggttct acggcatgga ctactggggc aaagggaccc aggtcaccgt ctcctca      357

<210> SEQ ID NO 3
<211> LENGTH: 378
<212> TYPE: DNA
<213> ORGANISM: Artificial Sequence
<220> FEATURE:
<223> OTHER INFORMATION: Description of Artificial Sequence: Synthetic
      sdAb Nef1 polynucleotide

<400> SEQUENCE: 3
gaggtgcagc tggtggagtc tgggggagga tcggtgcagg ctggggaatc tctgaggctc     60
acctgtatga gctctggaca cgccttcgct accaatacta tggcgtggtt ccgtctggtg   120
gcagggaagg aacgtgaatt tgtcgcagct gcgtctcggg gtattgagac cgcgctctat   180
gcagactccg tgaggggccg attcaccatc tctagagaca cgccaagaa cacggtgtat   240 ctgcaaatga acagcctgaa atctgaggac acggccgttt attactgtgc acaaagcatt   300
gacaggactg gttactcctt gggtaatatt cggagctatt cctactgggg ccaggggacc   360
caggtcactg tctcctca                                                  378

<210> SEQ ID NO 4
<211> LENGTH: 357
<212> TYPE: DNA
<213> ORGANISM: Artificial Sequence
<220> FEATURE:
<223> OTHER INFORMATION: Description of Artificial Sequence: Synthetic
      sdAb Nef2 polynucleotide

<400> SEQUENCE: 4
gaggtgcagc tggtggagtc tgggggaggc ttggtgcagc ctgggggtc tctgagactc      60 acctgtgcag cctctggatt caccttcagt agcagtgcca tgagctgggt ccgccaggct   120
ccaggaaagg ggctcgagtg ggtctcaaat attagtagtg gtggtggtag cacaagctat   180
gcagacttcg tgaagggccg attcaccatc tccagagaca cgccaagaa catgctgtat   240
```

```
ctgcagatgg acagtttgga acctgaggac acggccgttt attactgtac ggcctggctt    300
tggggttcgg ctgagtatga ctactggggc caggggaccc aggtcaccgt ctcctca      357
```

<210> SEQ ID NO 5
<211> LENGTH: 348
<212> TYPE: DNA
<213> ORGANISM: Artificial Sequence
<220> FEATURE:
<223> OTHER INFORMATION: Description of Artificial Sequence: Synthetic
      sdAb Nef5 polynucleotide

<400> SEQUENCE: 5

```
gaggtgcagc tggtggagtc tgggggaggc ttggtgcagg ctgggggctc tctgagactc    60
ttctgtgcgg cctctggatt caccttcggt accagtaata tggcctggct ccgccaggct   120
ccagggaagc gtcgcgagtg ggtcgcactt attacgatta gtggctacac agactatgca   180
gactccgtga aggaccgatt caccatatcc agagacaacg ccaagaacac ggtgtctctg   240
caaatgaaca gcctgaaacc tgaggacacg gccatttatt tttgcgcccg gcgtgtaggg   300
tctgagtatg atttgtgggg ccaggggacc caggtcactg tctcctca                348
```

<210> SEQ ID NO 6
<211> LENGTH: 348
<212> TYPE: DNA
<213> ORGANISM: Artificial Sequence
<220> FEATURE:
<223> OTHER INFORMATION: Description of Artificial Sequence: Synthetic
      sdAb Nef12 polynucleotide

<400> SEQUENCE: 6

```
gaggtgcagc tggtggagtc tgggggaggc ttggtgcagg ctgggggctc tctgagactc    60
ttctgtgcgg cctctggatt caccttcggt accagtaata tggcctggct ccgccaggct   120
ccagggaagc gtcgcgagtg ggtcgcactt attacgatta gtggctacac agactatgca   180
gactccgtga aggaccgatt caccatatcc agagacaacg ccaagaacac ggtgtctctg   240
caaatgaaca gcctgaaacc tgaggacacg gccatttatt tttgcgcccg gcgtgtaggg   300
tctgagtatg atttgtgggg ccaggggacc caggtcactg tctcctca                348
```

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      sdAb Nef19 polypeptide

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Ser Ile Phe Arg Ala Asn
            20                  25                  30

Ala Met Arg Trp Tyr Arg Gln Ala Pro Gly Lys Gln Arg Glu Trp Val
        35                  40                  45

Ala Ser Val Ile Ser Asp Asp Phe Thr Asp Tyr Val Asp Ser Val Arg
    50                  55                  60

Gly Arg Phe Thr Ile Ser Lys Asp Asn Ala Gln Asn Thr Val Tyr Leu
65                  70                  75                  80

Gln Met Asn Ser Leu Lys Pro Glu Asp Thr Ala Val Tyr Tyr Cys Asn
                85                  90                  95

-continued

```
Ala Gln Leu Gly Gly Val Asn Tyr Trp Gly Gln Gly Thr Gln Val Thr
            100                 105                 110

Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      sdAb Nef20 polypeptide

<400> SEQUENCE: 8

Glu Val Gln Leu Val Glu Ser Gly Gly Gly Leu Val Gln Ala Gly Gly
1               5                   10                  15

Ser Leu Ile Leu Ser Cys Ala Thr Ser Gly Arg Ile Phe Gly Ile Asn
            20                  25                  30

Ala Met Gly Trp Tyr Arg Gln Ala Pro Gly Lys Glu Arg Glu Leu Val
        35                  40                  45

Ala Val Ile Thr Ser Gly Gly Asn Thr Asn Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Phe Glu Asp Thr Ala Arg Tyr Tyr Cys Val
                85                  90                  95

Arg Ser Leu Pro Gly Trp Phe Tyr Gly Met Asp Tyr Trp Gly Lys Gly
            100                 105                 110

Thr Gln Val Thr Val Ser Ser
        115

<210> SEQ ID NO 9
<211> LENGTH: 126
<212> TYPE: PRT
<213> ORGANISM: Artificial Sequence
<220> FEATURE:
<223> OTHER INFORMATION: Description of Artificial Sequence: Synthetic
      sdAb Nef1 polypeptide

<400> SEQUENCE: 9

Glu Val Gln Leu Val Glu Ser Gly Gly Gly Ser Val Gln Ala Gly Glu
1               5                   10                  15

Ser Leu Arg Leu Thr Cys Met Ser Ser Gly His Ala Phe Ala Thr Asn
            20                  25                  30

Thr Met Ala Trp Phe Arg Leu Val Ala Gly Lys Glu Arg Glu Phe Val
        35                  40                  45

Ala Ala Ala Ser Arg Gly Ile Glu Thr Ala Leu Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Gln Ser Ile Asp Arg Thr Gly Tyr Ser Leu Gly Asn Ile Arg Ser
            100                 105                 110

Tyr Ser Tyr Trp Gly Gln Gly Thr Gln Val Thr Val Ser Ser
        115                 120                 125

<210> SEQ ID NO 10
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      sdAb Nef2 polypeptide

<400> SEQUENCE: 10

Glu Val Gln Leu Val Glu Ser Gly Gly Gly Leu Val Gln Pro Gly Gly
1               5                   10                  15

Ser Leu Arg Leu Thr Cys Ala Ala Ser Gly Phe Thr Phe Ser Ser
            20                  25                  30

Ala Met Ser Trp Val Arg Gln Ala Pro Gly Lys Gly Leu Glu Trp Val
            35                  40                  45

Ser Asn Ile Ser Ser Gly Gly Gly Ser Thr Ser Tyr Ala Asp Phe Val
        50                  55                  60

Lys Gly Arg Phe Thr Ile Ser Arg Asp Asn Ala Lys Asn Met Leu Tyr
65                  70                  75                  80

Leu Gln Met Asp Ser Leu Glu Pro Glu Asp Thr Ala Val Tyr Tyr Cys
                85                  90                  95

Thr Ala Trp Leu Trp Gly Ser Ala Glu Tyr Asp Tyr Trp Gly Gln Gly
            100                 105                 110

Thr Gln Val Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      sdAb Nef5 polypeptide

<400> SEQUENCE: 11

Glu Val Gln Leu Val Glu Ser Gly Gly Gly Leu Val His Ala Gly Gly
1               5                   10                  15

Ser Leu Arg Leu Phe Cys Ala Ala Ser Gly Phe Thr Phe Gly Thr Ser
            20                  25                  30

Asn Met Ala Trp Leu Arg Gln Ala Pro Gly Lys Arg Arg Glu Trp Val
            35                  40                  45

Ala Leu Ile Thr Ile Ser Gly Tyr Thr Asp Tyr Ala His Ser Val Lys
        50                  55                  60

Asp Arg Phe Thr Ile Ser Arg Asp Asn Ala Lys Asn Thr Val Ser Leu
65                  70                  75                  80

Gln Met Asn Ser Leu Lys Pro Glu Asp Thr Ala Ile Tyr Phe Cys Ala
                85                  90                  95

Arg Arg Val Gly Ser Glu Tyr Asp Leu Trp Gly Gln Gly Thr Gln Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
      sdAb Nef12 polypeptide

<400> SEQUENCE: 12
```

Glu Val Gln Leu Val Glu Ser Gly Gly Gly Leu Val Gln Ala Gly Gly
1               5                   10                  15

Ser Leu Arg Leu Phe Cys Ala Ala Ser Gly Phe Thr Phe Gly Thr Ser
            20                  25                  30

Asn Met Ala Trp Leu Arg Gln Ala Pro Gly Lys Arg Arg Glu Trp Val
        35                  40                  45

Ala Leu Ile Thr Ile Ser Gly Tyr Thr Asp Tyr Ala His Ser Val Lys
    50                  55                  60

Asp Arg Phe Thr Ile Ser Arg Asp Asn Ala Lys Asn Thr Val Ser Leu
65                  70                  75                  80

Gln Met Asn Ser Leu Lys Pro Glu Asp Thr Ala Ile Tyr Phe Cys Ala
            85                  90                  95

Arg Arg Val Gly Ser Glu Tyr Asp Leu Trp Gly Gln Gly Thr Gln Val
        100                 105                 110

Thr Val Ser Ser
        115

<210> SEQ ID NO 13
<211> LENGTH: 5025
<212> TYPE: DNA
<213> ORGANISM: Artificial Sequence
<220> FEATURE:
<223> OTHER INFORMATION: Description of Artificial Sequence: Synthetic
      pET14bNef13 polynucleotide

<400> SEQUENCE: 13

```
cgtcggccgc catgccggcg ataatggcct gcttctcgcc gaaacgtttg gtggcgggac    60
cagtgacgaa ggcttgagcg agggcgtgca agattccgaa taccgcaagc gacaggccga   120
tcatcgtcgc gctccagcga aagcggtcct cgccgaaaat gacccagagc gctgccggca   180
cctgtcctac gagttgcatg ataaagaaga cagtcataag tgcggcgacg atagtcatgc   240
cccgcgccca ccggaaggag ctgactgggt tgaaggctct caagggcatc ggtcgacgct   300
ctcccttatg cgactcctgc attaggaagc agcccagtag taggttgagg ccgttgagca   360
ccgccgccgc aaggaatggt gcatgcaagg agatggcgcc caacagtccc ccggccacgg   420
ggcctgccac catacccacg ccgaaacaag cgctcatgag cccgaagtgg cgagcccgat   480
cttccccatc ggtgatgtcg gcgatatagg cgccagcaac cgcacctgtg cgccggtga   540
tgccggccac gatgcgtccg gcgtagagga tcgagatctc gatcccgcga aattaatacg   600
actcactata gggagaccac aacggtttcc ctctagaaat aattttgttt aactttaaga   660
aggagatata ccatgggcca ccaccatcat catcacggat ccgaagcaca agaggaggag   720
gaggtgggtt ttccagtcac acctcaggta cctttaagac caatgactta caaggcagct   780
gtagatctta gccacttttt aaaagaaaag ggggactgg aagggctaat tcactcccaa   840
cgaagacaag atatccttga tctgtggatc taccacacac aaggctactt ccctgattgg   900
cagaactaca caccagggcc aggggtcaga tatccactga cctttggatg gtgctacaag   960
ctagtaccag ttgagccaga taaggtagaa gaggccaata aggagagaa caccagcttg  1020
ttacaccctg tgagcctgca tggaatggat gaccctgaga gagaagtgtt agagtggagg  1080
tttgacagcc gcctagcatt tcatcacgtg gcccgagagc tacatccgga gtacttcaag  1140
aactaagctg agcaataact agcataaccc cttggggcct ctaaacgggt cttgagggt  1200
tttttgctga aggaggaac tatatccgga tatccacagg acgggtgtgg tcgccatgat  1260
cgcgtagtcg atagtggctc caagtagcga agcgagcagg actgggcggc ggccaaagcg  1320
```

```
gtcggacagt gctccgagaa cgggtgcgca tagaaattgc atcaacgcat atagcgctag   1380
cagcacgcca tagtgactgg cgatgctgtc ggaatggacg atatcccgca agaggcccgg   1440
cagtaccggc ataaccaagc ctatgcctac agcatccagg gtgacggtgc cgaggatgac   1500
gatgagcgca ttgttagatt tcatacacgg tgcctgactg cgttagcaat ttaactgtga   1560
taaactaccg cattaaagct tatcgatgat aagctgtcaa acatgagaat tcttgaagac   1620
gaaagggcct cgtgatacgc ctatttttat aggttaatgt catgataata atggtttctt   1680
agacgtcagg tggcactttt cggggaaatg tgcgcggaac ccctatttgt ttatttttct   1740
aaatacattc aaatatgtat ccgctcatga gacaataacc ctgataaatg cttcaataat   1800
attgaaaaag gaagagtatg agtattcaac atttccgtgt cgcccttatt ccctttttgc   1860
cggcattttg ccttcctgtt tttgctcacc cagaaacgct ggtgaaagta aaagatgctg   1920
aagatcagtt gggtgcacga gtgggttaca tcgaactgga tctcaacagc ggtaagatcc   1980
ttgagagttt tcgccccgaa gaacgttttc caatgatgag cacttttaaa gttctgctat   2040
gtggcgcggt attatcccgt gttgacgccg ggcaagagca actcggtcgc cgcatacact   2100
attctcagaa tgacttggtt gagtactcac cagtcacaga aaagcatctt acggatggca   2160
tgacagtaag agaattatgc agtgctgcca taaccatgag tgataacact gcggccaact   2220
tacttctgac aacgatcgga ggaccgaagg agctaaccgc ttttttgcac aacatggggg   2280
atcatgtaac tcgccttgat cgttgggaac cggagctgaa tgaagccata ccaaacgacg   2340
agcgtgacac cacgatgcct gcagcaatgg caacaacgtt gcgcaaacta ttaactggcg   2400
aactacttac tctagcttcc cggcaacaat taatagactg gatggaggcg gataaagttg   2460
caggaccact tctgcgctcg gcccttccgg ctggctggtt tattgctgat aaatctggag   2520
ccggtgagcg tgggtctcgc ggtatcattg cagcactggg gccagatggt aagccctccc   2580
gtatcgtagt tatctacacg acggggagtc aggcaactat ggatgaacga atagacaga   2640 tcgctgagat aggtgcctca ctgattaagc attggtaact gtcagaccaa gtttactcat   2700
atatacttta gattgattta aaacttcatt tttaatttaa aaggatctag gtgaagatcc   2760
tttttgataa tctcatgacc aaaatccctt aacgtgagtt ttcgttccac tgagcgtcag   2820
accccgtaga aaagatcaaa ggatcttctt gagatccttt ttttctgcgc gtaatctgct   2880
gcttgcaaac aaaaaaacca ccgctaccag cggtggtttg tttgccggat caagagctac   2940
caactctttt tccgaaggta actggcttca gcagagcgca gataccaaat actgtccttc   3000
tagtgtagcc gtagttaggc caccacttca agaactctgt agcaccgcct acatacctcg   3060
ctctgctaat cctgttacca gtggctgctg ccagtggcga taagtcgtgt cttaccgggt   3120
tggactcaag acgatagtta ccggataagg cgcagcggtc gggctgaacg gggggttcgt   3180
gcacacagcc cagcttggag cgaacgacct acaccgaact gagataccta cagcgtgagc   3240
tatgagaaag cgccacgctt cccgaaggga gaaaggcgga caggtatccg gtaagcggca   3300
gggtcggaac aggagagcgc acgagggagc ttccaggggg aaacgcctgg tatctttata   3360
gtcctgtcgg gtttcgccac ctctgacttg agcgtcgatt tttgtgatgc tcgtcagggg   3420
ggcggagcct atgaaaaaac gccagcaacg cggccttttt acggttcctg gccttttgct   3480
ggccttttgc tcacatgttc tttcctgcgt tatcccctga ttctgtggat aaccgtatta   3540
ccgcctttga gtgagctgat accgctcgcc gcagccgaac gaccgagcgc agcgagtcag   3600
tgagcgagga agcggaagag cgcctgatgc ggtattttct ccttacgcat ctgtgcggta   3660
tttcacaccg catatatggt gcactctcag tacaatctgc tctgatgccg catagttaag   3720
```

```
ccagtataca ctccgctatc gctacgtgac tgggtcatgg ctgcgcccg acacccgcca      3780 acacccgctg acgcgccctg acgggcttgt ctgctcccgg catccgctta cagacaagct      3840
gtgaccgtct ccgggagctg catgtgtcag aggttttcac cgtcatcacc gaaacgcgcg      3900
aggcagctgc ggtaaagctc atcagcgtgg tcgtgaagcg attcacagat gtctgcctgt      3960
tcatccgcgt ccagctcgtt gagtttctcc agaagcgtta atgtctggct tctgataaag      4020
cgggccatgt taagggcggt ttttcctgt ttggtcactg atgcctccgt gtaaggggga      4080
tttctgttca tggggtaat gataccgatg aaacgagaga ggatgctcac gatacgggtt      4140
actgatgatg aacatgcccg gttactggaa cgttgtgagg gtaaacaact ggcggtatgg      4200
atgcggcggg accagagaaa aatcactcag ggtcaatgcc agcgcttcgt taatacagat      4260
gtaggtgttc cacagggtag ccagcagcat cctgcgatgc agatccggaa cataatggtg      4320
cagggcgctg acttccgcgt ttccagactt tacgaaacac ggaaaccgaa gaccattcat      4380
gttgttgctc aggtcgcaga cgttttgcag cagcagtcgc ttcacgttcg ctcgcgtatc      4440
ggtgattcat tctgctaacc agtaaggcaa ccccgccagc ctagccgggt cctcaacgac      4500
aggagcacga tcatgcgcac ccgtggccag gacccaacgc tgcccgagat gcgccgcgtg      4560
cggctgctgg agatggcgga cgcgatggat atgttctgcc aagggttggt ttgcgcattc      4620
acagttctcc gcaagaattg attggctcca attcttggag tggtgaatcc gttagcgagg      4680
tgccgccggc ttccattcag gtcgaggtgg cccggctcca tgcaccgcga cgcaacgcgg      4740
ggaggcagac aagtatagg gcggcgccta caatccatgc caacccgttc catgtgctcg      4800
ccgaggcggc ataaatcgcc gtgacgatca gcggtccagt gatcgaagtt aggctggtaa      4860
gagccgcgag cgatccttga agctgtccct gatggtcgtc atctacctgc ctggacagca      4920
tggcctgcaa cgcgggcatc ccgatgccgc cggaagcgag aagaatcata atggggaagg      4980
ccatccagcc tcgcgtcgcg aacgccagca agacgtagcc cagcg                      5025
```

<210> SEQ ID NO 14
<211> LENGTH: 5034
<212> TYPE: DNA
<213> ORGANISM: Artificial Sequence
<220> FEATURE:
<223> OTHER INFORMATION: Description of Artificial Sequence: Synthetic
      pET14bNefW12 polynucleotide

<400> SEQUENCE: 14

```
cgtcggccgc catgccggcg ataatggcct gcttctcgcc gaaacgtttg gtggcgggac        60
cagtgacgaa ggcttgagcg agggcgtgca agattccgaa taccgcaagc gacaggccga       120
tcatcgtcgc gctccagcga aagcggtcct cgccgaaaat gacccagagc gctgccggca       180
cctgtcctac gagttgcatg ataaagaaga cagtcataag tgcggcgacg atagtcatgc       240
cccgcgccca ccggaaggag ctgactgggt tgaaggctct caagggcatc ggtcgacgct       300
ctcccttatg cgactcctgc attaggaagc agcccagtag taggttgagg ccgttgagca       360
ccgccgccgc aaggaatggt gcatgcaagg agatggcgcc caacagtccc ccggccacgg       420
ggcctgccac cataccccacg ccgaaacaag cgctcatgag cccgaagtgg cgagcccgat       480
cttccccatc ggtgatgtcg gcgatatagg cgccagcaac cgcacctgtg cgccggtga        540 tgccggccac gatgcgtccg gcgtagagga tcgagatctc gatcccgcga aattaatacg       600
actcactata gggagaccac aacgttttcc ctctagaaat aatttgttt aactttaaga       660 aggagatata ccatgggcca ccaccatcat catcacggat ccgcctggct agaagcacaa       720
```

```
gaggaggagg aggtgggttt tccagtcaca cctcaggtac ctttaagacc aatgacttac        780
aaggcagctg tagatcttag ccactttta aaagaaaagg ggggactgga agggctaatt         840
cactcccaac gaagacaaga tatccttgat ctgtggatct accacacaca aggctacttc        900
cctgattggc agaactacac accagggcca ggggtcagat atccactgac ctttggatgg        960
tgctacaagc tagtaccagt tgagccagat aaggtagaag aggccaataa aggagagaac       1020
accagcttgt tacaccctgt gagcctgcat ggaatggatg accctgagag agaagtgtta       1080
gagtggaggt ttgacagccg cctagcattt catcacgtgg cccgagagct gcatccggag       1140
tacttcaaga actaagctga gcaataacta gcataacccc ttggggcctc taaacgggtc       1200
ttgaggggtt ttttgctgaa aggaggaact atatccggat atccacagga cgggtgtggt       1260
cgccatgatc gcgtagtcga tagtggctcc aagtagcgaa gcgagcagga ctgggcggcg       1320
gccaaagcgg tcggacagtg ctccgagaac gggtgcgcat agaaattgca tcaacgcata       1380
tagcgctagc agcacgccat agtgactggc gatgctgtcg gaatggacga tatcccgcaa       1440
gaggcccggc agtaccggca taaccaagcc tatgcctaca gcatccaggg tgacggtgcc       1500
gaggatgacg atgagcgcat tgttagattt catacacggt gcctgactgc gttagcaatt       1560
taactgtgat aaactaccgc attaaagctt atcgatgata agctgtcaaa catgagaatt       1620
cttgaagacg aaagggcctc gtgatacgcc tatttttata ggttaatgtc atgataataa       1680
tggtttctta gacgtcaggt ggcactttc ggggaaatgt gcgcggaacc cctatttgtt        1740
tattttccta aatacattca aatatgtatc cgctcatgag acaataaccc tgataaatgc       1800
ttcaataata ttgaaaaagg aagagtatga gtattcaaca tttccgtgtc gcccttattc       1860 cctttttgc ggcattttgc cttcctgttt ttgctcaccc agaaacgctg gtgaaagtaa        1920
aagatgctga agatcagttg ggtgcacgag tgggttacat cgaactggat ctcaacagcg       1980
gtaagatcct tgagttttt cgccccgaag aacgttttcc aatgatgagc acttttaaag       2040
ttctgctatg tggcgcggta ttatcccgtg ttgacgccgg gcaagagcaa ctcggtcgcc       2100
gcatacacta ttctcagaat gacttggttg agtactcacc agtcacagaa aagcatctta       2160
cggatggcat gacagtaaga gaattatgca gtgctgccat aaccatgagt gataacactg       2220
cggccaactt acttctgaca acgatcggag gaccgaagga gctaaccgct ttttgcaca        2280 acatggggga tcatgtaact cgccttgatc gttgggaacc ggagctgaat gaagccatac       2340
caaacgacga gcgtgacacc acgatgcctg cagcaatggc aacaacgttg cgcaaactat       2400
taactggcga actacttact ctagcttccc ggcaacaatt aatagactgg atggaggcgg       2460
ataaagttgc aggaccactt ctgcgctcgg cccttccggc tggctggttt attgctgata       2520
aatctggagc cggtgagcgt gggtctcgcg gtatcattgc agcactgggg ccagatggta       2580
agccctcccg tatcgtagtt atctacacga cggggagtca ggcaactatg gatgaacgaa       2640
atagacagat cgctgagata ggtgcctcac tgattaagca ttggtaactg tcagaccaag       2700
tttactcata tatactttag attgatttaa aacttcattt ttaatttaaa aggatctagg       2760
tgaagatcct ttttgataat ctcatgacca aaatccctta acgtgagttt tcgttccact       2820
gagcgtcaga ccccgtagaa aagatcaaag gatcttcttg agatcctttt tttctgcgcg       2880
taatctgctg cttgcaaaca aaaaaaccac cgctaccagc ggtggtttgt ttgccggatc       2940
aagagctacc aactcttttt ccgaaggtaa ctggcttcag cagagcgcag ataccaaata       3000
ctgtccttct agtgtagccg tagttaggcc accacttcaa gaactctgta gcaccgccta       3060
```

```
catacctcgc tctgctaatc ctgttaccag tggctgctgc cagtggcgat aagtcgtgtc    3120
ttaccgggtt ggactcaaga cgatagttac cggataaggc gcagcggtcg ggctgaacgg    3180
ggggttcgtg cacacagccc agcttggagc gaacgaccta caccgaactg agatacctac    3240
agcgtgagct atgagaaagc gccacgcttc ccgaagggag aaaggcggac aggtatccgg    3300
taagcggcag ggtcggaaca ggagagcgca cgagggagct tccaggggga aacgcctggt    3360
atctttatag tcctgtcggg tttcgccacc tctgacttga gcgtcgattt ttgtgatgct    3420 cgtcagggggg gcggagccta tggaaaaacg ccagcaacgg gcctttttta cggttcctgg    3480 cctttttgctg gccttttgct cacatgttct ttcctgcgtt atccctgat tctgtggata    3540 accgtattac cgcctttgag tgagctgata ccgctcgccg cagccgaacg accgagcgca    3600
gcgagtcagt gagcgaggaa gcggaagagc gcctgatgcg gtattttctc cttacgcatc    3660
tgtgcggtat tcacaccgc atatatggtg cactctcagt acaatctgct ctgatgccgc    3720
atagttaagc cagtatacac tccgctatcg ctacgtgact gggtcatggc tgcgccccga    3780
cacccgccaa cacccgctga cgcgccctga cgggcttgtc tgctcccggc atccgcttac    3840
agacaagctg tgaccgtctc cgggagctgc atgtgtcaga ggttttcacc gtcatcaccg    3900
aaacgcgcga ggcagctgcg gtaaagctca tcagcgtggt cgtgaagcga ttcacagatg    3960
tctgcctgtt catccgcgtc cagctcgttg agtttctcca gaagcgttaa tgtctggctt    4020
ctgataaagc gggccatgtt aagggcggtt ttttcctgtt tggtcactga tgcctccgtg    4080
taagggggat ttctgttcat gggggtaatg ataccgatga acgagagag gatgctcacg    4140 atacgggtta ctgatgatga acatgcccgg ttactggaac gttgtgaggg taaacaactg    4200
gcggtatgga tgcggcggga ccagagaaaa atcactcagg gtcaatgcca gcgcttcgtt    4260
aatacagatg taggtgttcc acagggtagc cagcagcatc ctgcgatgca gatccggaac    4320
ataatggtgc agggcgctga cttccgcgtt tccagacttt acgaaacacg gaaaccgaag    4380
accattcatg ttgttgctca ggtcgcagac gttttgcagc agcagtcgct tcacgttcgc    4440
tcgcgtatcg gtgattcatt ctgctaacca gtaaggcaac cccgccagcc tagccgggtc    4500
ctcaacgaca ggagcacgat catgcgcacc cgtggccagg acccaacgct gcccgagatg    4560
cgccgcgtgc ggctgctgga tggcggac gcgatggata tgttctgcca agggttggtt    4620
tgcgcattca cagttctccg caagaattga ttggctccaa ttcttggagt ggtgaatccg    4680
ttagcgaggt gccgccggct tccattcagg tcgaggtggc ccggctccat gcaccgcgac    4740
gcaacgcggg gaggcagaca aggtataggg cggcgcctac aatccatgcc aacccgttcc    4800
atgtgctcgc cgaggcggca taaatcgccg tgacgatcag cggtccagtg atcgaagtta    4860
ggctggtaag agccgcgagc gatccttgaa gctgtccctg atggtcgtca tctacctgcc    4920
tggacagcat ggcctgcaac gcgggcatcc cgatgccgcc ggaagcgaga agaatcataa    4980
tggggaaggc catccagcct cgcgtcgcga acgccagcaa gacgtagccc agcg          5034
```

<210> SEQ ID NO 15
<211> LENGTH: 5044
<212> TYPE: DNA
<213> ORGANISM: Artificial Sequence
<220> FEATURE:
<223> OTHER INFORMATION: Description of Artificial Sequence: Synthetic
      pET14bNefW10 polynucleotide

<400> SEQUENCE: 15

```
cgtcggccgc catgccggcg ataatggcct gcttctcgcc gaaacgtttg gtggcgggac      60
```

|  |  |
|---|---|
| cagtgacgaa ggcttgagcg agggcgtgca agattccgaa taccgcaagc gacaggccga | 120 |
| tcatcgtcgc gctccagcga aagcggtcct cgccgaaaat gacccagagc gctgccggca | 180 |
| cctgtcctac gagttgcatg ataaagaaga cagtcataag tgcggcgacg atagtcatgc | 240 |
| cccgcgccca ccggaaggag ctgactgggt tgaaggctct caagggcatc ggtcgacgct | 300 |
| ctcccttatg cgactcctgc attaggaagc agcccagtag taggttgagg ccgttgagca | 360 |
| ccgccgccgc aaggaatggt gcatgcaagg agatggcgcc caacagtccc ccggccacgg | 420 |
| ggcctgccac catacccacg ccgaaacaag cgctcatgag cccgaagtgg cgagcccgat | 480 |
| cttccccatc ggtgatgtcg gcgatatagg cgccagcaac cgcacctgtg cgccggtga | 540 |
| tgccggccac gatgcgtccg gcgtagagga tcgagatctc gatcccgcga aattaatacg | 600 |
| actcactata gggagaccac aacggtttcc ctctagaaat aattttgttt aactttaaga | 660 |
| aggagatata ccatgggctg gctcgaggcg caggaggagg aggaggtggg ttttccagtc | 720 |
| acacctcagg tacctttaag accaatgact tacaaggcag ctgtagatct tagccacttt | 780 |
| ttaaaagaaa aggggggact ggaagggcta attcactccc aacgaagaca agatatcctt | 840 |
| gatctgtgga tctaccacac acaaggctac ttccctgatt ggcagaacta cacaccaggg | 900 |
| ccaggggtca gatatccact gacctttgga tggtgctaca agctagtacc agttgagcca | 960 |
| gataaggtag aagaggccaa taaaggagag aacaccagct tgttacaccc tgtgagcctg | 1020 |
| catggaatgg atgaccctga gagagaagtg ttagagtgga ggtttgacag ccgcctagca | 1080 |
| tttcatcacg tggcccgaga gctgcatccg gagtacttca agaacgcggc cgcacaccac | 1140 |
| catcatcatc acgatcccta agcttgctga gcaataacta gcataacccc ttggggcctc | 1200 |
| taaacgggtc ttgaggggtt ttttgctgaa aggaggaact atatccggat atccacagga | 1260 |
| cgggtgtggt cgccatgatc gcgtagtcga tagtggctcc aagtagcgaa gcgagcagga | 1320 |
| ctgggcggcg ccaaagcgg tcggacagtg ctccgagaac gggtgcgcat agaaattgca | 1380 |
| tcaacgcata tagcgctagc agcacgccat agtgactggc gatgctgtcg gaatggacga | 1440 |
| tatcccgcaa gaggcccggc agtaccggca taaccaagcc tatgcctaca gcatccaggg | 1500 |
| tgacggtgcc gaggatgacg atgagcgcat tgttagattt catacacggt gcctgactgc | 1560 |
| gttagcaatt taactgtgat aaactaccgc attaaagctt atcgatgata agctgtcaaa | 1620 |
| catgagaatt cttgaagacg aaagggcctc gtgatacgcc tatttttata ggttaatgtc | 1680 |
| atgataataa tggtttctta gacgtcaggt ggcacttttc ggggaaatgt gcgcggaacc | 1740 |
| cctatttgtt tatttttcta aatacattca aatatgtatc cgctcatgag acaataaccc | 1800 |
| tgataaatgc ttcaataata ttgaaaaagg aagagtatga gtattcaaca tttccgtgtc | 1860 |
| gcccttattc ccttttttgc ggcattttgc cttcctgttt ttgctcaccc agaaacgctg | 1920 |
| gtgaaagtaa aagatgctga agatcagttg ggtgcacgag tgggttacat cgaactggat | 1980 |
| ctcaacagcg gtaagatcct tgagagtttt cgccccgaag aacgttttcc aatgatgagc | 2040 |
| acttttaaag ttctgctatg tggcgcggta ttatcccgtg ttgacgccgg caagagcaa | 2100 |
| ctcggtcgcc gcatacacta ttctcagaat gacttggttg agtactcacc agtcacagaa | 2160 |
| aagcatctta cggatggcat gacagtaaga gaattatgca gtgctgccat aaccatgagt | 2220 |
| gataacactg cggccaactt acttctgaca acgatcggag gaccgaagga gctaaccgct | 2280 |
| tttttgcaca acatggggga tcatgtaact cgccttgatc gttgggaacc ggagctgaat | 2340 |
| gaagccatac caaacgacga gcgtgacacc acgatgcctg cagcaatggc aacaacgttg | 2400 |
| cgcaaactat taactggcga actacttact ctagcttccc ggcaacaatt aatagactgg | 2460 |

```
atggaggcgg ataaagttgc aggaccactt ctgcgctcgg cccttccggc tggctggttt    2520
attgctgata aatctggagc cggtgagcgt gggtctcgcg gtatcattgc agcactgggg    2580
ccagatggta agccctcccg tatcgtagtt atctacacga cggggagtca ggcaactatg    2640
gatgaacgaa atagacagat cgctgagata ggtgcctcac tgattaagca ttggtaactg    2700
tcagaccaag tttactcata tatactttag attgatttaa aacttcattt ttaatttaaa    2760
aggatctagg tgaagatcct ttttgataat ctcatgacca aaatccctta acgtgagttt    2820
tcgttccact gagcgtcaga ccccgtagaa aagatcaaag gatcttcttg agatcctttt    2880
tttctgcgcg taatctgctg cttgcaaaca aaaaaaccac cgctaccagc ggtggtttgt    2940
ttgccggatc aagagctacc aactcttttt ccgaaggtaa ctggcttcag cagagcgcag    3000
ataccaaata ctgtccttct agtgtagccg tagttaggcc accacttcaa gaactctgta    3060
gcaccgccta catacctcgc tctgctaatc ctgttaccag tggctgctgc cagtggcgat    3120
aagtcgtgtc ttaccgggtt ggactcaaga cgatagttac cggataaggc gcagcggtcg    3180
ggctgaacgg ggggttcgtg cacacagccc agcttggagc gaacgaccta caccgaactg    3240
agatacctac agcgtgagct atgagaaagc gccacgcttc ccgaagggag aaaggcggac    3300
aggtatccgg taagcggcag ggtcggaaca ggagagcgca cgagggagct tccaggggga    3360
aacgcctggt atctttatag tcctgtcggg tttcgccacc tctgacttga gcgtcgattt    3420
ttgtgatgct cgtcaggggg gcggagccta tggaaaaacg ccagcaacgc ggccttttta    3480
cggttcctgg ccttttgctg gccttttgct cacatgttct ttcctgcgtt atcccctgat    3540
tctgtggata accgtattac cgcctttgag tgagctgata ccgctcgccg cagccgaacg    3600
accgagcgca gcgagtcagt gagcgaggaa gcggaagagc gcctgatgcg gtattttctc    3660
cttacgcatc tgtgcggtat ttcacaccgc atatatggtg cactctcagt acaatctgct    3720
ctgatgccgc atagttaagc cagtatacac tccgctatcg ctacgtgact gggtcatggc    3780
tgcgccccga cacccgccaa cacccgctga cgcgccctga cgggcttgtc tgctcccggc    3840
atccgcttac agacaagctg tgaccgtctc cgggagctgc atgtgtcaga ggttttcacc    3900
gtcatcaccg aaacgcgcga ggcagctgcg gtaaagctca tcagcgtggt cgtgaagcga    3960
ttcacagatg tctgcctgtt catccgcgtc cagctcgttg agtttctcca gaagcgttaa    4020
tgtctggctt ctgataaagc gggccatgtt aagggcggtt ttttcctgtt tggtcactga    4080
tgcctccgtg taagggggat ttctgttcat gggggtaatg ataccgatga acgagagag    4140 gatgctcacg atacgggtta ctgatgatga acatgcccgg ttactggaac gttgtgaggg    4200
taaacaactg gcggtatgga tgcggcggga ccagagaaaa atcactcagg gtcaatgcca    4260
gcgcttcgtt aatacagatg taggtgttcc acagggtagc cagcagcatc ctgcgatgca    4320
gatccggaac ataatggtgc agggcgctga cttccgcgtt tccagacttt acgaaacacg    4380
gaaaccgaag accattcatg ttgttgctca ggtcgcagac gttttgcagc agcagtcgct    4440
tcacgttcgc tcgcgtatcg gtgattcatt ctgctaacca gtaaggcaac cccgccagcc    4500
tagccgggtc tcaacgacaa ggagcacgat catgcgcacc cgtggccagg acccaacgct    4560
gcccgagatg cgccgcgtgc ggctgctgga gatggcggac gcgatggata tgttctgcca    4620
agggttggtt tgcgcattca cagttctccg caagaattga ttggctccaa ttcttggagt    4680
ggtgaatccg ttagcgaggt gccgccggct tccattcagg tcgaggtggc ccggctccat    4740
gcaccgcgac gcaacgcggg gaggcagaca aggtataggg cggcgcctac aatccatgcc    4800
```

```
aacccgttcc atgtgctcgc cgaggcggca taaatcgccg tgacgatcag cggtccagtg    4860
atcgaagtta ggctggtaag agccgcgagc gatccttgaa gctgtccctg atggtcgtca    4920
tctacctgcc tggacagcat ggcctgcaac gcgggcatcc cgatgccgcc ggaagcgaga    4980
agaatcataa tggggaaggc catccagcct cgcgtcgcga acgccagcaa gacgtagccc    5040
agcg                                                                 5044
```

<210> SEQ ID NO 16
<211> LENGTH: 4548
<212> TYPE: DNA
<213> ORGANISM: Artificial Sequence
<220> FEATURE:
<223> OTHER INFORMATION: Description of Artificial Sequence: Synthetic
    pHen6HisGS polynucleotide

<400> SEQUENCE: 16

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
catgcaaatt ctatttcaag gagacagtca taatgaaata cctattgcct acggcagccg     300
ctggattgtt attactcgcg gcccagccgg ccatggccca ggtgcagctg caggtcgacc     360
tcgagatcaa cgggcggcc gcagaacaaa aactcatctc agaagaggat ctgaatgggg     420
ccgcacatca ccaccatcac catgggagct agactgttga agttgtttta gcaaaacctc     480
atacagaaaa ttcatttact aacgtctgga agacgacaa actttagat cgttacgcta     540 actatgaggg ctgtctgtgg aatgctacag gcgttgtggt ttgtactggt gacgaaactc     600
agtgttacgg tacatgggtt cctattgggc ttgctatccc tgaaaatgag ggtggtggct     660
ctgagggtgg cggttctgag ggtggcggtt ctgagggtgg cggtactaaa cctcctgagt     720
acggtgatac acctattccg ggctatactt atatcaaccc tctcgacggc acttatccgc     780
ctggtactga gcaaaacccc gctaatccta atccttctct tgaggagtct cagcctctta     840
atactttcat gtttcagaat aataggttcc gaaataggca gggtgcatta actgtttata     900
cgggcactgt tactcaaggc actgacccc ttaaaactta ttaccagtac actcctgtat     960
catcaaaagc catgtatgac gcttactgga acggtaaatt cagagactgc gctttccatt    1020
ctggctttaa tgaggatcca ttcgtttgtg aatatcaagg ccaatcgtct gacctgcctc    1080
aacctcctgt caatgctggc ggcggctctg gtggtggttc tggtggcggc tctgagggtg    1140
gcggctctga gggtggcggt tctgagggtg gcggctctga gggtggcggt tccggtggcg    1200
gctccggttc cggtgatttt gattatgaaa aatggcaaa cgctaataag ggggctatga    1260
ccgaaaatgc cgatgaaaac gcgctacagt ctgacgctaa aggcaaactt gattctgtcg    1320
ctactgatta cggtgctgct atcgatggtt tcattggtga cgtttccggc cttgctaatg    1380
gtaatggtgc tactggtgat tttgctggct ctaattccca aatggctcaa gtcggtgacg    1440
gtgataattc acctttaatg aataattttc cgtcaatattt accttctttg cctcagtcgg    1500
ttgaatgtcg cccttatgtc tttggcgctg gtaaaccata tgaattttct attgattgtg    1560
acaaaataaa cttattccgt ggtgtctttg cgtttcttt atatgttgcc acctttatgt    1620
atgtattttc gacgtttgct aacatactgc gtaataagga gtcttaataa gaattcactg    1680
gccgtcgttt tacaacgtcg tgactgggaa aaccctggcg ttacccaact taatcgcctt    1740
```

```
gcagcacatc cccctttcgc cagctggcgt aatagcgaag aggcccgcac cgatcgccct    1800
tcccaacagt tgcgcagcct gaatggcgaa tggcgcctga tgcggtattt tctccttacg    1860
catctgtgcg gtatttcaca ccgcatacgt caaagcaacc atagtacgcg ccctgtagcg    1920
gcgcattaag cgcggcgggt gtggtggtta cgcgcagcgt gaccgctaca cttgccagcg    1980
ccctagcgcc cgctcctttc gctttcttcc cttcctttct cgccacgttc gccggctttc    2040
cccgtcaagc tctaaatcgg gggctccctt tagggttccg atttagtgct ttacggcacc    2100
tcgaccccaa aaaacttgat tgggtgatg gttcacgtag tgggccatcg ccctgataga    2160 cggttttcg cccttgacg ttggagtcca cgttctttaa tagtggactc ttgttccaaa    2220
ctggaacaac actcaaccct atctcgggct attctttga tttataaggg attttgccga    2280
tttcggccta ttggttaaaa aatgagctga tttaacaaaa attaacgcg aattttaaca    2340 aaatattaac gtttacaatt ttatggtgca ctctcagtac aatctgctct gatgccgcat    2400
agttaagcca gccccgacac ccgccaacac ccgctgacgc gccctgacgg gcttgtctgc    2460
tcccggcatc cgcttacaga caagctgtga ccgtctccgg gagctgcatg tgtcagaggt    2520
tttcaccgtc atcaccgaaa cgcgcgagac gaaagggcct cgtgatacgc ctattttat    2580 aggttaatgt catgataata atggttctt agacgtcagg tggcactttt cggggaaatg    2640
tgcgcggaac ccctatttgt ttattttct aaatacattc aaatatgtat ccgctcatga    2700
gacaataacc ctgataaatg cttcaataat attgaaaaag gaagagtatg agtattcaac    2760
atttccgtgt cgcccttatt cccttttttg cggcattttg ccttcctgtt tttgctcacc    2820
cagaaacgct ggtgaaagta aaagatgctg aagatcagtt gggtgcacga gtgggttaca    2880
tcgaactgga tctcaacagc ggtaagatcc ttgagagttt cgccccgaa gaacgttttc    2940 caatgatgag cacttttaaa gttctgctat gtggcgcggt attatcccgt attgacgccg    3000
ggcaagagca actcggtcgc cgcatacact attctcagaa tgacttggtt gagtactcac    3060
cagtcacaga aaagcatctt acggatggca tgacagtaag agaattatgc agtgctgcca    3120
taaccatgag tgataacact gcggccaact tacttctgac aacgatcgga ggaccgaagg    3180
agctaaccgc ttttttgcac aacatggggg atcatgtaac tcgccttgat cgttgggaac    3240
cggagctgaa tgaagccata ccaaacgacg agcgtgacac cacgatgcct gtagcaatgg    3300
caacaacgtt gcgcaaacta ttaactggcg aactacttac tctagcttcc cggcaacaat    3360
taatagactg gatggaggcg gataaagttg caggaccact tctgcgctcg gcccttccgg    3420
ctggctggtt tattgctgat aaatctggag ccggtgagcg tgggtctcgc ggtatcattg    3480
cagcactggg gccagatggt aagccctccc gtatcgtagt tatctacacg acggggagtc    3540
aggcaactat ggatgaacga atagacaga tcgctgagat aggtgcctca ctgattaagc    3600
attggtaact gtcagaccaa gtttactcat atatacttta gattgattta aaacttcatt    3660
tttaatttaa aaggatctag gtgaagatcc ttttgataa tctcatgacc aaaatccctt    3720
aacgtgagtt ttcgttccac tgagcgtcag accccgtaga aaagatcaaa ggatcttctt    3780
gagatccttt ttttctgcgc gtaatctgct gcttgcaaac aaaaaaacca ccgctaccag    3840
cggtggtttg tttgccggat caagagctac caactctttt tccgaaggta actggcttca    3900
gcagagcgca gataccaaat actgtccttc tagtgtagcc gtagttaggc caccacttca    3960
agaactctgt agcaccgcct acatacctcg ctctgctaat cctgttacca gtggctgctg    4020
ccagtggcga taagtcgtgt cttaccgggt tggactcaag acgatagtta ccggataagg    4080
cgcagcggtc gggctgaacg ggggttcgt gcacacagcc cagcttggag cgaacgacct    4140
```

```
acaccgaact gagataccta cagcgtgagc tatgagaaag cgccacgctt cccgaaggga    4200
gaaaggcgga caggtatccg gtaagcggca gggtcggaac aggagagcgc acgagggagc    4260 ttccagggg aaacgcctgg tatctttata gtcctgtcgg gtttcgccac ctctgacttg     4320
agcgtcgatt tttgtgatgc tcgtcagggg ggcggagcct atggaaaaac gccagcaacg    4380 cggcctttt acggttcctg gccttttgct ggccttttgc tcacatgttc tttcctgcgt     4440
tatcccctga ttctgtggat aaccgtatta ccgcctttga gtgagctgat accgctcgcc    4500
gcagccgaac gaccgagcgc agcgagtcag tgagcgagga agcggaag                 4548
```

<210> SEQ ID NO 17
<211> LENGTH: 5877
<212> TYPE: DNA
<213> ORGANISM: Artificial Sequence
<220> FEATURE:
<223> OTHER INFORMATION: Description of Artificial Sequence: Synthetic
      pHenPhoA6His polynucleotide

<400> SEQUENCE: 17

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
catgcaaatt ctatttcaag gagacagtca taatgaaata cctattgcct acggcagccg    300
ctggattgtt attactcgcg gcccagccgg ccatggcagc cgatcctcga gctcccgg      360 gctgcagccc tgttctggaa accgggctg ctcagggcga tattactgca cccggcggtg     420
ctcgccgttt aacgggtgat cagactgccg ctctgcgtga ttctcttagc gataaacctg    480
caaaaaatat tattttgctg attggcgatg ggatggggga ctcggaaatt actgccgcac    540
gtaattatgc cgaaggtgcg ggcggctttt ttaaaggtat agatgcctta ccgcttaccg    600
ggcaatacac tcactatgcg ctgaataaaa aaaccggcaa accggactac gtcaccgact    660
cggctgcatc agcaaccgcc tggtcaaccg gtgtcaaaac ctataacggc gcgctgggcg    720
tcgatattca cgaaaaagat cacccaacga ttctggaaat ggcaaaagcc gcaggtctgg    780
cgaccggtaa cgtttctacc gcagagttgc aggatgccac gccgctgcg ctggtggcac     840 atgtgacctc gcgcaaatgc tacggtccga gcgcgaccag tgaaaaatgt ccgggtaacg    900
ctctggaaaa aggcggaaaa ggatcgatta ccgaacagct gcttaacgct cgtgccgacg    960
ttacgcttgg cggcggcgca aaaaccttg ctgaaacggc aaccgctggt gaatggcagg    1020
gaaaaacgct gcgtgaacag gcacaggcgc gtggttatca gttggtgagc gatgctgcct    1080
cactgaattc ggtgacggaa gcgaatcagc aaaaacccct gcttggcctg tttgctgacg    1140
gcaatatgcc agtgcgctgg ctaggaccga agcaacgta ccacggcaat atcgataagc     1200
ccgcagtcac ctgtacgcca aatccgcaac gtaatgacag tgtaccaacc ctggcgcaga    1260
tgaccgacaa agccattgaa ttgttgagta aaaatgagaa aggcttttc ctgcaagttg     1320 aaggtgcgtc aatcgataaa caggatcatg ctgcgaatcc ttgtgggcaa attggcgaga    1380
cggtcgatct cgatgaagcc gtacaacggg cgctggaatt cgctaaaaag gagggtaaca    1440
cgctggtcat agtcaccgct gatcacgccc acgccagcca gattgttgcg ccggatacca    1500
aagctccggg cctcacccag gcgctaaata ccaaagatgg cgcagtgatg gtgatgagtt    1560
acgggaactc cgaagaggat tcacaagaac ataccggcag tcagttgcgt attgcggcgt    1620
```

```
atggcccgca tgccgccaat gttgttggac tgaccgacca gaccgatctc ttctacacca      1680
tgaaagccgc tctggggctg aaagcggccg cagaacaaaa actcatctca gaagaggatc      1740
tgaatggggc cgcacatcac caccatcacc atgggagcta gactgttgaa agttgtttag      1800
caaaacctca tacagaaaat tcatttacta acgtctggaa agacgacaaa actttagatc      1860
gttacgctaa ctatgagggc tgtctgtgga atgctacagg cgttgtggtt tgtactggtg      1920
acgaaactca gtgttacggt acatgggttc ctattgggct tgctatccct gaaaatgagg      1980
gtggtggctc tgagggtggc ggttctgagg gtggcggttc tgagggtggc ggtactaaac      2040
ctcctgagta cggtgataca cctattccgg gctatactta tatcaaccct ctcgacggca      2100
cttatccgcc tggtactgag caaaaccccg ctaatcctaa tccttctctt gaggagtctc      2160
agcctcttaa tactttcatg tttcagaata ataggttccg aaataggcag gtgcattaa       2220 ctgtttatac gggcactgtt actcaaggca ctgaccccgt taaaacttat taccagtaca      2280
ctcctgtatc atcaaaagcc atgtatgacg cttactggaa cggtaaattc agagactgcg      2340 cttttccattc tggctttaat gaggatccat tcgtttgtga atatcaaggc caatcgtctg     2400
acctgcctca acctcctgtc aatgctggcg gcggctctgg tggtggttct ggtgccggct      2460
ctgagggtgg cggctctgag ggtggcggtt ctgagggtgg cggctctgag ggtggcggtt      2520
ccggtggcgg ctccggttcc ggtgattttg attatgaaaa aatggcaaac gctaataagg      2580
gggctatgac cgaaaatgcc gatgaaaacg cgctacagtc tgacgctaaa ggcaaacttg      2640
attctgtcgc tactgattac ggtgctgcta tcgatggttt cattggtgac gtttccggcc      2700
ttgctaatgg taatggtgct actggtgatt ttgctggctc taattcccaa atggctcaag      2760
tcggtgacgg tgataattca cctttaatga ataatttccg tcaatattta ccttctttgc      2820
ctcagtcggt tgaatgtcgc ccttatgtct ttggcgctgg taaaccatat gaattttcta     2880
ttgattgtga caaaataaac ttattccgtg gtgtctttgc gtttctttta tatgttgcca      2940
cctttatgta tgtattttcg acgtttgcta acatactgcg taataaggag tcttaataag      3000
aattcactgg ccgtcgtttt acaacgtcgt gactgggaaa accctggcgt tacccaactt      3060
aatcgccttg cagcacatcc ccctttcgcc agctggcgta tagcgaaga ggcccgcacc       3120 gatcgccctt cccaacagtt gcgcagcctg aatggcgaat ggcgcctgat gcggtatttt      3180
ctccttacgc atctgtgcgg tatttcacac cgcatacgtc aaagcaacca tagtacgcgc      3240
cctgtagcgg cgcattaagc gcggcgggtg tggtggttac gcgcagcgtg accgctacac      3300
ttgccagcgc cctagcgccc gctcctttcg ctttcttccc ttcctttctc gccacgttcg      3360
ccggctttcc ccgtcaagct ctaaatcggg ggctcccttt agggttccga tttagtgctt      3420
tacggcacct cgaccccaaa aaacttgatt tgggtgatgg ttcacgtagt gggccatcgc      3480
cctgatagac ggtttttcgc cctttgacgt tggagtccac gttctttaat agtggactct      3540
tgttccaaac tggaacaaca ctcaacccta tctcggcta ttcttttgat ttataaggga      3600
ttttgccgat ttcggcctat tggttaaaaa atgagctgat ttaacaaaaa tttaacgcga      3660
attttaacaa aatattaacg tttacaattt tatggtgcac tctcagtaca atctgctctg      3720
atgccgcata gttaagccag ccccgacacc cgccaacacc cgctgacgcg ccctgacggg      3780
cttgtctgct cccggcatcc gcttacagac aagctgtgac cgtctccggg agctgcatgt      3840
gtcagaggtt ttcaccgtca tcaccgaaac gcgcgagacg aaagggcctc gtgatacgcc      3900 tattttata ggttaatgtc atgataataa tggtttctta gacgtcaggt ggcactttc        3960
```

```
ggggaaatgt gcgcggaacc cctatttgtt tattttttcta aatacattca aatatgtatc    4020
cgctcatgag acaataaccc tgataaatgc ttcaataata ttgaaaaagg aagagtatga    4080
gtattcaaca tttccgtgtc gcccttattc cttttttgc ggcattttgc cttcctgttt     4140
ttgctcaccc agaaacgctg gtgaaagtaa aagatgctga agatcagttg ggtgcacgag    4200
tgggttacat cgaactggat ctcaacagcg gtaagatcct tgagagtttt cgccccgaag    4260
aacgttttcc aatgatgagc acttttaaag ttctgctatg tggcgcggta ttatcccgta    4320
ttgacgccgg gcaagagcaa ctcggtcgcc gcatacacta ttctcagaat gacttggttg    4380
agtactcacc agtcacagaa aagcatctta cggatggcat gacagtaaga gaattatgca    4440
gtgctgccat aaccatgagt gataacactg cggccaactt acttctgaca acgatcggag    4500
gaccgaagga gctaaccgct ttttgcaca acatggggga tcatgtaact cgccttgatc    4560
gttgggaacc ggagctgaat gaagccatac caaacgacga gcgtgacacc acgatgcctg    4620
tagcaatggc aacaacgttg cgcaaactat taactggcga actacttact ctagcttccc    4680
ggcaacaatt aatagactgg atggaggcgg ataaagttgc aggaccactt ctgcgctcgg    4740
cccttccggc tggctggttt attgctgata atctggagcc cggtgagcgt gggtctcgcg    4800
gtatcattgc agcactgggg ccagatggta agccctcccg tatcgtagtt atctacacga    4860
cggggagtca ggcaactatg gatgaacgaa atagacagat cgctgagata ggtgcctcac    4920
tgattaagca ttggtaactg tcagaccaag tttactcata tactttag attgatttaa     4980 aacttcattt ttaatttaaa aggatctagg tgaagatcct ttttgataat ctcatgacca    5040
aaatccctta acgtgagttt tcgttccact gagcgtcaga ccccgtagaa aagatcaaag    5100
gatcttcttg agatcctttt ttctgcgcg taatctgctg cttgcaaaca aaaaaaccac     5160
cgctaccagc ggtggtttgt tgccggatc aagagctacc aactcttttt ccgaaggtaa     5220
ctggcttcag cagagcgcag ataccaaata ctgtccttct agtgtagccg tagttaggcc    5280
accacttcaa gaactctgta gcaccgccta catacctcgc tctgctaatc ctgttaccag    5340
tggctgctgc cagtggcgat aagtcgtgtc ttaccgggtt ggactcaaga cgatagttac    5400
cggataaggc gcagcggtcg ggctgaacgg ggggttcgtg cacacagccc agcttggagc    5460
gaacgaccta caccgaactg agatacctac agcgtgagct atgagaaagc gccacgcttc    5520
ccgaagggag aaaggcggac aggtatccgg taagcggcag ggtcggaaca ggagagcgca    5580
cgagggagct ccaggggga acgcctggt atctttatag tcctgtcggg tttcgccacc      5640
tctgacttga gcgtcgattt ttgtgatgct cgtcagggg gcggagccta tggaaaaacg     5700
ccagcaacgc ggccttttta cggttcctgg ccttttgctg gccttttgct cacatgttct    5760
ttcctgcgtt atcccctgat tctgtggata accgtattac cgcctttgag tgagctgata    5820
ccgctcgccg cagccgaacg accgagcgca gcgagtcagt gagcgaggaa gcggaag      5877
```

<210> SEQ ID NO 18
<211> LENGTH: 4857
<212> TYPE: DNA
<213> ORGANISM: Artificial Sequence
<220> FEATURE:
<223> OTHER INFORMATION: Description of Artificial Sequence: Synthetic
      pHen-sdAb Nef1 polynucleotide

<400> SEQUENCE: 18

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
```

```
tcactcatta ggcacccag  gctttacact ttatgcttcc ggctcgtatg ttgtgtggaa     180
ttgtgagcgg ataacaattt cacacaggaa acagctatga ccatgattac gccaagcttg    240
catgcaaatt ctatttcaag gagacagtca taatgaaata cctattgcct acggcagccg    300
ctggattgtt attactcgcg gcccagccgg ccatggccga ggtgcagctg gtggagtctg    360
ggggaggctt ggtgcagcct ggggggtctc tgaaactctc ctgtgcagcc tctggaagca    420
tcttcagagc caatgccatg cgctggtacc gccaggctcc aggaaaacag cgcgagtggg    480
tcgcaagtgt tattagtgat gatttcacag actatgtaga ctctgtgagg ggccgattca    540
ccatctccaa agacaacgcc cagaacacgt gtatctccca aatgaacagc ctgaaacctg    600
aggacacggc cgtctattac tgtaatgcgc aactcggcgg agtcaactac tggggccagg    660
ggacccaggt caccgtctcc tcagcggccg cagaacaaaa actcatctca agaggatc     720
tgaatgggc  cgcacatcac caccatcacc atgggagcta gactgttgaa agttgtttag    780
caaaacctca tacagaaaat tcatttacta acgtctggaa agacgacaaa actttagatc    840
gttacgctaa ctatgagggc tgtctgtgga atgctacagg cgttgtggtt tgtactggtg    900
acgaaactca gtgttacggt acatgggttc ctattgggct tgctatccct gaaaatgagg    960
gtggtggctc tgagggtggc ggttctgagg gtggcggttc tgagggtggc ggtactaaac   1020
ctcctgagta cggtgataca cctattccgg gctatactta tatcaaccct ctcgacggca   1080
cttatccgcc tggtactgag caaaaccccg ctaatcctaa tccttctctt gaggagtctc   1140
agcctcttaa tactttcatg tttcagaata taggttccg  aaataggcag gtgcattaa    1200
ctgtttatac gggcactgtt actcaaggca ctgaccccgt taaaacttat taccagtaca   1260
ctcctgtatc atcaaaagcc atgtatgacg cttactggaa cggtaaattc agagactgcg   1320
cttttccatt ggctttaat  gaggatccat tcgtttgtga atatcaaggc caatcgtctg   1380
acctgcctca acctcctgtc aatgctggcg gcggctctgg tggtggttct ggtggcggct   1440
ctgagggtgg cggctctgag ggtggcggtt ctgagggtgg cggctctgag ggtggcggtt   1500
ccggtggcgg ctccggttcc ggtgatttg  attatgaaaa aatggcaaac gctaataagg   1560
gggctatgac cgaaaatgcc gatgaaaacg cgctacagtc tgacgctaaa ggcaaacttg   1620
attctgtcgc tactgattac ggtgctgcta tcgatggttt cattggtgac gtttccggcc   1680
ttgctaatgg taatggtgct actggtgatt tgctggctc  taattcccaa atggctcaag   1740
tcggtgacgg tgataattca cctttaatga ataatttccg tcaatattta ccttctttgc   1800
ctcagtcggt tgaatgtcgc ccttatgtct ttggcgctgg taaaccatat gaattttcta   1860
ttgattgtga caaaataaac ttattccgtg gtgtctttgc gtttctttta tatgttgcca   1920
cctttatgta tgtattttcg acgtttgcta acatactgcg taataaggag tcttaataag   1980
aattcactgg ccgtcgtttt acaacgtcgt gactgggaaa accctggcgt tacccaactt   2040
aatcgccttg cagcacatcc ccctttcgcc agctggcgta atagcgaaga ggcccgcacc   2100
gatcgccctt cccaacagtt gcgcagcctg aatggcgaat ggcgcctgat gcggtatttt   2160
ctccttacgc atctgtgcgg tatttcacac cgcatacgtc aaagcaacca tagtacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt tgggtgatgg ttcacgtagt gggccatcgc   2460
cctgatagac ggtttttcgc cctttgacgt tggagtccac gttctttaat agtggactct   2520
```

```
tgttccaaac tggaacaaca ctcaaccctc tctcgggcta ttcttttgat ttataaggga    2580
ttttgccgat ttcggcctat tggttaaaaa atgagctgat ttaacaaaaa tttaacgcga    2640
attttaacaa atattaacg tttacaattt tatggtgcac tctcagtaca atctgctctg     2700
atgccgcata gttaagccag ccccgacacc cgccaacacc cgctgacgcg ccctgacggg    2760
cttgtctgct cccggcatcc gcttacagac aagctgtgac cgtctccggg agctgcatgt    2820
gtcagaggtt ttcaccgtca tcaccgaaac gcgcgagacg aaagggcctc gtgatacgcc    2880
tatttttata ggttaatgtc atgataataa tggtttctta gacgtcaggt ggcacttttc    2940
ggggaaatgt gcgcggaacc cctatttgtt tatttttcta atacattca aatatgtatc     3000
cgctcatgag acaataaccc tgataaatgc ttcaataata ttgaaaaagg aagagtatga    3060
gtattcaaca tttccgtgtc gcccttattc ccttttttgc ggcattttgc cttcctgttt    3120
ttgctcaccc agaaacgctg gtgaaagtaa aagatgctga agatcagttg ggtgcacgag    3180
tgggttacat cgaactggat ctcaacagcg gtaagatcct tgagagtttt cgccccgaag    3240
aacgttttcc aatgatgagc acttttaaag ttctgctatg tggcgcggta ttatcccgta    3300
ttgacgccgg gcaagagcaa ctcggtcgcc gcatacacta ttctcagaat gacttggttg    3360
agtactcacc agtcacagaa aagcatctta cggatggcat gacagtaaga gaattatgca    3420
gtgctgccat aaccatgagt gataacactg cggccaactt acttctgaca acgatcggag    3480
gaccgaagga gctaaccgct tttttgcaca acatggggga tcatgtaact cgccttgatc    3540
gttgggaacc ggagctgaat gaagccatac caaacgacga gcgtgacacc acgatgcctg    3600
tagcaatggc aacaacgttg cgcaaactat taactggcga actacttact ctagcttccc    3660
ggcaacaatt aatagactgg atggaggcgg ataaagttgc aggaccactt ctgcgctcgg    3720
cccttccggc tggctggttt attgctgata aatctggagc cggtgagcgt gggtctcgcg    3780
gtatcattgc agcactgggg ccagatggta agccctcccg tatcgtagtt atctacacga    3840
cggggagtca ggcaactatg gatgaacgaa atagacagat cgctgagata ggtgcctcac    3900
tgattaagca ttggtaactg tcagaccaag tttactcata tatactttag attgatttaa    3960
aacttcattt ttaatttaaa aggatctagg tgaagatcct ttttgataat ctcatgacca    4020
aaatccctta acgtgagttt tcgttccact gagcgtcaga ccccgtagaa aagatcaaag    4080
gatcttcttg agatcctttt tttctgcgcg taatctgctg cttgcaaaca aaaaaaccac    4140
cgctaccagc ggtggtttgt ttgccggatc aagagctacc aactcttttt ccgaaggtaa    4200
ctggcttcag cagagcgcag ataccaaata ctgtccttct agtgtagccg tagttaggcc    4260
accacttcaa gaactctgta gcaccgccta catacctcgc tctgctaatc ctgttaccag    4320
tggctgctgc cagtggcgat aagtcgtgtc ttaccgggtt ggactcaaga cgatagttac    4380
cggataaggc gcagcggtcg ggctgaacgg ggggttcgtg cacacagccc agcttggagc    4440
gaacgaccta caccgaactg agatacctac agcgtgagct atgagaaagc gccacgcttc    4500
ccgaagggag aaaggcggac aggtatccgg taagcggcag ggtcggaaca ggagagcgca    4560
cgagggagct tccaggggga aacgcctggt atctttatag tcctgtcggg tttcgccacc    4620
tctgacttga gcgtcgattt ttgtgatgct cgtcaggggg gcggagccta tggaaaaacg    4680
ccagcaacgc ggcctttta cggttcctgg ccttttgctg gccttttgct cacatgttct    4740
ttcctgcgtt atcccctgat tctgtggata accgtattac cgcctttgag tgagctgata    4800
ccgctcgccg cagccgaacg accgagcgca gcgagtcagt gagcgaggaa gcggaag      4857
```

<210> SEQ ID NO 19
<211> LENGTH: 4869
<212> TYPE: DNA
<213> ORGANISM: Artificial Sequence
<220> FEATURE:
<223> OTHER INFORMATION: Description of Artificial Sequence: Synthetic pHen-sdAb Nef2 polynucleotide

<400> SEQUENCE: 19

| | | | | | |
|---|---|---|---|---|---|
| agcgcccaat | acgcaaaccg | cctctccccg | cgcgttggcc | gattcattaa tgcagctggc | 60 |
| acgacaggtt | tcccgactgg | aaagcgggca | gtgagcgcaa | cgcaattaat gtgagttagc | 120 |
| tcactcatta | ggcaccccag | gctttacact | ttatgcttcc | ggctcgtatg ttgtgtggaa | 180 |
| ttgtgagcgg | ataacaattt | cacacaggaa | acagctatga | ccatgattac gccaagcttg | 240 |
| catgcaaatt | ctatttcaag | gagacagtca | taatgaaata | cctattgcct acggcagccg | 300 |
| ctggattgtt | attactcgcg | gcccagccgg | ccatggccga | ggtgcagctg gtggagtctg | 360 |
| ggggaggctt | ggtgcaggct | ggagggtctc | tgatactctc | ctgtgcaacc tctggtagga | 420 |
| tcttcggtat | caatgccatg | ggctggtacc | gccaggctcc | agggaaggag cgcgagttgg | 480 |
| tcgcagttat | taccagtggt | ggaaacacaa | actatgcaga | ctccgtgaag gccgattca | 540 |
| ccatctccaa | agacaatgcc | aagaacacgc | tgtatctgca | aatgaatagc ctgaaatttg | 600 |
| aggacacggc | ccggtactac | tgtgtgagat | ccctccctgg | gtggttctac ggcatggact | 660 |
| actgggcaa | agggacccag | gtcaccgtct | cctcagcggc | cgcagaacaa aaactcatct | 720 |
| cagaagagga | tctgaatggg | gccgcacatc | accaccatca | ccatgggagc tagactgttg | 780 |
| aaagttgttt | agcaaaacct | catacagaaa | attcatttac | taacgtctgg aaagacgaca | 840 |
| aaactttaga | tcgttacgct | aactatgagg | gctgtctgtg | aatgctaca ggcgttgtgg | 900 |
| tttgtactgg | tgacgaaact | cagtgttacg | gtacatgggt | tcctattggg cttgctatcc | 960 |
| ctgaaaatga | gggtggtggc | tctgagggtg | gcggttctga | gggtggcggt tctgagggtg | 1020 |
| gcggtactaa | acctcctgag | tacggtgata | cacctattcc | gggctatact tatatcaacc | 1080 |
| ctctcgacgg | cacttatccg | cctggtactg | agcaaaaccc | cgctaatcct aatccttctc | 1140 |
| ttgaggagtc | tcagcctctt | aatactttca | tgtttcagaa | taataggttc cgaaataggc | 1200 |
| agggtgcatt | aactgtttat | acgggcactg | ttactcaagg | cactgacccc gttaaaactt | 1260 |
| attaccagta | cactcctgta | tcatcaaaag | ccatgtatga | cgcttactgg aacggtaaat | 1320 |
| tcagagactg | cgctttccat | tctggcttta | atgaggatcc | attcgtttgt gaatatcaag | 1380 |
| gccaatcgtc | tgacctgcct | caacctcctg | tcaatgctgg | cggcggctct ggtggtggtt | 1440 |
| ctggtggcgg | ctctgagggt | ggcggctctg | agggtggcgg | ttctgagggt ggcggctctg | 1500 |
| agggtggcgg | ttccggtggc | ggctccggtt | ccggtgattt | tgattatgaa aaaatggcaa | 1560 |
| acgctaataa | gggggctatg | accgaaaatg | ccgatgaaaa | cgcgctacag tctgacgcta | 1620 |
| aaggcaaact | tgattctgtc | gctactgatt | acggtgctgc | tatcgatggt ttcattggtg | 1680 |
| acgtttccgg | ccttgctaat | ggtaatggtg | ctactggtga | ttttgctggc tctaattccc | 1740 |
| aaatggctca | agtcggtgac | ggtgataatt | cacctttaat | gaataatttc cgtcaatatt | 1800 |
| taccttcttt | gcctcagtcg | gttgaatgtc | gcccttatgt | ctttggcgct ggtaaaccat | 1860 |
| atgaattttc | tattgattgt | gacaaaataa | acttattccg | tggtgtcttt gcgtttcttt | 1920 |
| tatatgttgc | cacctttatg | tatgtatttt | cgacgtttgc | taacatactg cgtaataagg | 1980 |
| agtcttaata | agaattcact | ggccgtcgtt | ttacaacgtc | gtgactggga aaaccctggc | 2040 |

```
gttacccaac ttaatcgcct tgcagcacat cccccttttcg ccagctggcg taatagcgaa    2100
gaggcccgca ccgatcgccc ttcccaacag ttgcgcagcc tgaatggcga atggcgcctg    2160
atgcggtatt ttctccttac gcatctgtgc ggtatttcac accgcatacg tcaaagcaac    2220
catagtacgc gccctgtagc ggcgcattaa gcgcggcggg tgtggtggtt acgcgcagcg    2280
tgaccgctac acttgccagc gccctagcgc ccgctccttt cgctttcttc ccttcctttc    2340
tcgccacgtt cgccggcttt ccccgtcaag ctctaaatcg gggctccct ttagggttcc     2400 gatttagtgc tttacggcac ctcgacccca aaaaacttga tttgggtgat ggttcacgta    2460
gtgggccatc gccctgatag acggttttc gcccttttgac gttggagtcc acgttcttta    2520
atagtggact cttgttccaa actggaacaa cactcaaccc tatctcgggc tattcttttg    2580
atttataagg gattttgccg atttcggcct attggttaaa aaatgagctg atttaacaaa    2640
aatttaacgc gaattttaac aaaatattaa cgtttacaat tttatggtgc actctcagta    2700
caatctgctc tgatgccgca tagttaagcc agccccgaca cccgccaaca cccgctgacg    2760
cgccctgacg ggcttgtctg ctcccggcat ccgcttacag acaagctgtg accgtctccg    2820
ggagctgcat gtgtcagagg ttttcaccgt catcaccgaa acgcgcgaga cgaaagggcc    2880
tcgtgatacg cctattttta taggttaatg tcatgataat aatggtttct tagacgtcag    2940
gtggcacttt tcggggaaat gtgcgcggaa ccccctatttg tttatttttc taaatacatt   3000
caaatatgta tccgctcatg agacaataac cctgataaat gcttcaataa tattgaaaaa    3060
ggaagagtat gagtattcaa catttccgtg tcgcccttat cccttttttt gcggcatttt    3120
gccttcctgt ttttgctcac ccagaaacgc tggtgaaagt aaaagatgct gaagatcagt    3180
tgggtgcacg agtgggttac atcgaactgg atctcaacag cggtaagatc cttgagagtt    3240
ttcgccccga agaacgtttt ccaatgatga gcacttttaa agttctgcta tgtggcgcgg    3300
tattatcccg tattgacgcc gggcaagagc aactcggtcg ccgcatacac tattctcaga    3360
atgacttggt tgagtactca ccagtcacag aaaagcatct tacgatggc atgacagtaa     3420 gagaattatg cagtgctgcc ataaccatga gtgataacac tgcggccaac ttacttctga    3480
caacgatcgg aggaccgaag gagctaaccg cttttttgca caacatgggg gatcatgtaa    3540
ctcgccttga tcgttgggaa ccggagctga atgaagccat accaaacgac gagcgtgaca    3600
ccacgatgcc tgtagcaatg gcaacaacgt tgcgcaaact attaactggc gaactactta    3660
ctctagcttc ccggcaacaa ttaatagact ggatggaggc ggataaagtt gcaggaccac    3720
ttctgcgctc ggcccttccg gctggctggt ttattgctga taaatctgga gccggtgagc    3780
gtgggtctcg cggtatcatt gcagcactgg ggccagatgg taagccctcc cgtatcgtag    3840
ttatctacac gacggggagt caggcaacta tggatgaacg aaatagacag atcgctgaga    3900
taggtgcctc actgattaag cattggtaac tgtcagacca agtttactca tatatacttt    3960
agattgattt aaaacttcat ttttaattta aaaggatcta ggtgaagatc ctttttgata    4020
atctcatgac caaaatccct taacgtgagt tttcgttcca ctgagcgtca gaccccgtag    4080
aaaagatcaa aggatcttct tgagatcctt ttttttctgcg cgtaatctgc tgcttgcaaa    4140
caaaaaaacc accgctacca gcggtggttt gtttgccgga tcaagagcta ccaactcttt    4200
ttccgaaggt aactggcttc agcagagcgc agataccaaa tactgtcctt ctagtgtagc    4260
cgtagttagg ccaccacttc aagaactctg tagcaccgcc tacatacctc gctctgctaa    4320
tcctgttacc agtggctgct gccagtggcg ataagtcgtg tcttaccggg ttggactcaa    4380
gacgatagtt accggataag gcgcagcggt cgggctgaac ggggggttcg tgcacacagc    4440
```

```
ccagcttgga gcgaacgacc tacaccgaac tgagatacct acagcgtgag ctatgagaaa    4500
gcgccacgct tcccgaaggg agaaaggcgg acaggtatcc ggtaagcggc agggtcggaa    4560
caggagagcg cacgagggag cttccagggg gaaacgcctg gtatctttat agtcctgtcg    4620
ggtttcgcca cctctgactt gagcgtcgat ttttgtgatg ctcgtcaggg gggcggagcc    4680
tatggaaaaa cgccagcaac gcggcctttt tacggttcct ggccttttgc tggccttttg    4740
ctcacatgtt ctttcctgcg ttatccctg attctgtgga taaccgtatt accgcctttg     4800
agtgagctga taccgctcgc cgcagccgaa cgaccgagcg cagcgagtca gtgagcgagg    4860
aagcggaag                                                              4869
```

<210> SEQ ID NO 20
<211> LENGTH: 4890
<212> TYPE: DNA
<213> ORGANISM: Artificial Sequence
<220> FEATURE:
<223> OTHER INFORMATION: Description of Artificial Sequence: Synthetic
      pHen-sdAb Nef5 polynucleotide

<400> SEQUENCE: 20

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagcttg   240
catgcaaatt ctatttcaag gagacagtca taatgaaata cctattgcct acggcagccg   300
ctggattgtt attactcgcg gcccagccgg ccatggccga ggtgcagctg gtggagtctg   360
ggggaggatc ggtgcaggct ggggaatctc tgaggctcac ctgtatgagc tctggacacg   420
ccttcgctac caatactatg gcgtggttcc gtctggtggc agggaaggaa cgtgaatttg   480
tcgcagctgc gtctcggggt attgagaccg cgctctatgc agactccgtg aggggccgat   540
tcaccatctc tagagacaac gccaagaaca cggtgtatct gcaaatgaac agcctgaaat   600
ctgaggacac ggccgtttat tactgtgcac aaagcattga caggactggt tactccttgg   660
gtaatattcg gagctattcc tactggggcc aggggaccca ggtcactgtc tcctcagcgg   720
ccgcagaaca aaaactcatc tcagaagagg atctgaatgg ggccgcacat caccaccatc   780
accatgggag ctagactgtt gaaagttgtt tagcaaaacc tcatacagaa aattcattta   840
ctaacgtctg gaaagacgac aaaactttag atcgttacgc taactatgag ggctgtctgt   900
ggaatgctac aggcgttgtg gtttgtactg gtgacgaaac tcagtgttac ggtacatggg   960
ttcctattgg gcttgctatc cctgaaaatg agggtggtgg ctctgagggt ggcggttctg  1020
agggtggcgg ttctgagggt ggcggtacta aacctcctga gtacggtgat acacctattc  1080
cgggctatac ttatatcaac cctctcgacg gcacttatcc gcctggtact gagcaaaacc  1140
ccgctaatcc taatccttct cttgaggagt ctcagcctct taatactttc atgtttcaga  1200
ataataggtt ccgaaatagg cagggtgcat taactgttta tacgggcact gttactcaag  1260
gcactgaccc cgttaaaact tattaccagt acactcctgt atcatcaaaa gccatgtatg  1320
acgcttactg gaacggtaaa ttcagagact gcgctttcca ttctggcttt aatgaggatc  1380
cattcgtttg tgaatatcaa ggccaatcgt ctgacctgcc tcaacctcct gtcaatgctg  1440
gcggcggctc tggtggtggt tctggtggcg gctctgaggg tggcggctct gagggtggcg  1500
gttctgaggg tggcggctct gagggtggcg gttccggtgg cggctccggt tccggtgatt  1560
```

```
ttgattatga aaaaatggca aacgctaata aggggggctat gaccgaaaat gccgatgaaa    1620
acgcgctaca gtctgacgct aaaggcaaac ttgattctgt cgctactgat tacggtgctg    1680
ctatcgatgg tttcattggt gacgtttccg gccttgctaa tggtaatggt gctactggtg    1740
attttgctgg ctctaattcc caaatggctc aagtcggtga cggtgataat tcacctttaa    1800
tgaataattt ccgtcaatat ttaccttctt tgcctcagtc ggttgaatgt cgcccttatg    1860
tctttggcgc tggtaaacca tatgaatttt ctattgattg tgacaaaata aacttattcc    1920
gtggtgtctt tgcgtttctt ttatatgttg ccacctttat gtatgtattt tcgacgtttg    1980
ctaacatact gcgtaataag gagtcttaat aagaattcac tggccgtcgt tttacaacgt    2040
cgtgactggg aaaaccctgg cgttacccaa cttaatcgcc ttgcagcaca tccccctttc    2100
gccagctggg gtaatagcga gaggcccgc accgatcgcc cttcccaaca gttgcgcagc    2160
ctgaatggcg aatggcgcct gatgcggtat tttctcctta cgcatctgtg cggtatttca    2220
caccgcatac gtcaaagcaa ccatagtacg cgccctgtag cggcgcatta agcgcggcgg    2280
gtgtggtggt tacgcgcagc gtgaccgcta cacttgccag cgccctagcg cccgctcctt    2340
tcgctttctt cccttccttt ctcgccacgt tcgccggctt tccccgtcaa gctctaaatc    2400
gggggctccc tttagggttc cgatttagtg ctttacggca cctcgacccc aaaaaacttg    2460
atttgggtga tggttcacgt agtgggccat cgccctgata cggtttttt cgccctttga    2520 cgttggagtc cacgttcttt aatagtggac tcttgttcca aactggaaca cactcaacc    2580 ctatctcggg ctattctttt gatttataag gattttgcc gatttcggcc tattggttaa    2640
aaaatgagct gatttaacaa aaatttaacg cgaatttaa caaaatatta cgtttacaa    2700 ttttatggtg cactctcagt acaatctgct ctgatgccgc atagttaagc cagccccgac    2760
acccgccaac acccgctgac gcgccctgac gggcttgtct gctcccggca tccgcttaca    2820
gacaagctgt gaccgtctcc gggagctgca tgtgtcagag gttttcaccg tcatcaccga    2880
aacgcgcgag acgaaagggc ctcgtgatac gcctattttt ataggttaat gtcatgataa    2940
taatggtttc ttagacgtca ggtggcactt ttcggggaaa tgtgcgcgga acccctattt    3000
gtttattttt ctaaatacat tcaaatatgt atccgctcat gagacaataa ccctgataaa    3060
tgcttcaata atattgaaaa aggaagagta tgagtattca acatttccgt gtcgccctta    3120 ttccctttt tgcggcattt tgccttcctg ttttgctca cccagaaacg ctggtgaaag    3180
taaaagatgc tgaagatcag ttgggtgcac gagtgggtta catcgaactg gatctcaaca    3240
gcggtaagat ccttgagagt tttcgccccg aagaacgttt tccaatgatg agcactttta    3300
aagttctgct atgtggcgcg gtattatccc gtattgacgc cgggcaagag caactcggtc    3360
gccgcataca ctattctcag aatgacttgg ttgagtactc accagtcaca gaaaagcatc    3420
ttacggatgg catgacagta agagaattat gcagtgctgc cataaccatg agtgataaca    3480
ctgcggccaa cttacttctg acaacgatcg gaggaccgaa ggagctaacc gcttttttgc    3540
acaacatggg ggatcatgta actcgccttg atcgttggga accggagctg aatgaagcca    3600
taccaaacga cgagcgtgac accacgatgc ctgtagcaat ggcaacaacg ttgcgcaaac    3660
tattaactgg cgaactactt actctagctt cccggcaaca attaatagac tggatggagg    3720
cggataaagt tgcaggacca cttctgcgct cggcccttcc ggctggctgg tttattgctg    3780
ataaatctgg agccggtgag cgtgggtctc gcggtatcat tgcagcactg gggccagatg    3840
gtaagccctc ccgtatcgta gttatctaca cgacggggag tcaggcaact atggatgaac    3900
```

```
gaaatagaca gatcgctgag ataggtgcct cactgattaa gcattggtaa ctgtcagacc    3960
aagtttactc atatatactt tagattgatt taaaacttca ttttaattt aaaaggatct    4020 aggtgaagat cctttttgat aatctcatga ccaaaatccc ttaacgtgag ttttcgttcc    4080
actgagcgtc agaccccgta gaaaagatca aaggatcttc ttgagatcct ttttttctgc    4140
gcgtaatctg ctgcttgcaa acaaaaaaac caccgctacc agcggtggtt tgtttgccgg    4200
atcaagagct accaactctt tttccgaagg taactggctt cagcagagcg cagataccaa    4260
atactgtcct tctagtgtag ccgtagttag gccaccactt caagaactct gtagcaccgc    4320
ctacatacct cgctctgcta atcctgttac cagtggctgc tgccagtggc gataagtcgt    4380
gtcttaccgg gttggactca agacgatagt taccggataa ggcgcagcgg tcgggctgaa    4440
cggggggttc gtgcacacag cccagcttgg agcgaacgac ctacaccgaa ctgagatacc    4500
tacagcgtga gctatgagaa agcgccacgc ttcccgaagg gagaaaggcg gacaggtatc    4560
cggtaagcgg cagggtcgga acaggagagc gcacgaggga gcttccaggg ggaaacgcct    4620
ggtatcttta tagtcctgtc gggtttcgcc acctctgact tgagcgtcga ttttgtgat    4680 gctcgtcagg gggcggagc ctatggaaaa acgccagcaa cgcggccttt ttacggttcc    4740
tggccttttg ctggccttt gctcacatgt tctttcctgc gttatcccct gattctgtgg    4800
ataaccgtat taccgccttt gagtgagctg ataccgctcg ccgcagccga acgaccgagc    4860
gcagcgagtc agtgagcgag gaagcggaag                                    4890
```

<210> SEQ ID NO 21
<211> LENGTH: 4869
<212> TYPE: DNA
<213> ORGANISM: Artificial Sequence
<220> FEATURE:
<223> OTHER INFORMATION: Description of Artificial Sequence: Synthetic
      pHen-sdAb Nef12 polynucleotide

<400> SEQUENCE: 21

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
catgcaaatt ctatttcaag agacagtca taatgaaata cctattgcct acggcagccg     300
ctggattgtt attactcgcg gcccagccgg ccatggccga ggtgcagctg gtggagtctg     360
ggggaggctt ggtgcagcct ggggggtctc tgagactcac ctgtgcagcc tctggattca     420
ccttcagtag cagtgccatg agctgggtcc gccaggctcc aggaaagggg ctcgagtggg     480
tctcaaatat tagtagtggt ggtggtagca caagctatgc agacttcgtg aagggccgat     540
tcaccatctc cagagacaac gccaagaaca tgctgtatct gcagatggac agtttggaac     600
ctgaggacac ggccgtttat tactgtacgg cctggctttg gggttcggct gagtatgact     660
actggggcca ggggacccag gtcaccgtct cctcagcggc cgcagaacaa aaactcatct     720
cagaagagga tctgaatggg gccgcacatc accaccatca ccatgggagc tagactgttg     780
aaagttgttt agcaaaacct catacagaaa attcatttac taacgtctgg aaagacgaca     840
aaactttaga tcgttacgct aactatgagg gctgtctgtg gaatgctaca ggcgttgtgg     900
tttgtactgg tgacgaaact cagtgttacg gtacatgggt tcctattggg cttgctatcc     960
ctgaaaatga gggtggtggc tctgagggtg gcggttctga gggtggcggt tctgagggtg    1020
```

| | | | | | |
|---|---|---|---|---|---|
| gcggtactaa | acctcctgag | tacggtgata | cacctattcc | gggctatact | tatatcaacc | 1080 |
| ctctcgacgg | cacttatccg | cctggtactg | agcaaaaccc | cgctaatcct | aatccttctc | 1140 |
| ttgaggagtc | tcagcctctt | aatactttca | tgtttcagaa | taataggttc | cgaaataggc | 1200 |
| agggtgcatt | aactgtttat | acgggcactg | ttactcaagg | cactgacccc | gttaaaactt | 1260 |
| attaccagta | cactcctgta | tcatcaaaag | ccatgtatga | cgcttactgg | aacggtaaat | 1320 |
| tcagagactg | cgcttttccat | tctggcttta | atgaggatcc | attcgtttgt | gaatatcaag | 1380 |
| gccaatcgtc | tgacctgcct | caacctcctg | tcaatgctgg | cggcggctct | ggtggtggtt | 1440 |
| ctggtggcgg | ctctgagggt | ggcggctctg | agggtggcgg | ttctgagggt | ggcggctctg | 1500 |
| agggtggcgg | ttccggtggc | ggctccggtt | ccggtgattt | tgattatgaa | aaaatggcaa | 1560 |
| acgctaataa | gggggctatg | accgaaaatg | ccgatgaaaa | cgcgctacag | tctgacgcta | 1620 |
| aaggcaaaact | tgattctgtc | gctactgatt | acggtgctgc | tatcgatggt | ttcattggtg | 1680 |
| acgtttccgg | ccttgctaat | ggtaatggtg | ctactggtga | ttttgctggc | tctaattccc | 1740 |
| aaatggctca | agtcggtgac | ggtgataatt | cacctttaat | gaataatttc | cgtcaatatt | 1800 |
| taccttcttt | gcctcagtcg | gttgaatgtc | gcccttatgt | cttggcgct | ggtaaaccat | 1860 |
| atgaattttc | tattgattgt | gacaaaataa | acttattccg | tggtgtcttt | gcgtttcttt | 1920 |
| tatatgttgc | cacctttatg | tatgtatttt | cgacgtttgc | taacatactg | cgtaataagg | 1980 |
| agtcttaata | agaattcact | ggccgtcgtt | ttacaacgtc | gtgactggga | aaaccctggc | 2040 |
| gttacccaac | ttaatcgcct | tgcagcacat | ccccctttcg | ccagctggcg | taatagcgaa | 2100 |
| gaggcccgca | ccgatcgccc | ttcccaacag | ttgcgcagcc | tgaatggcga | atggcgcctg | 2160 |
| atgcggtatt | ttctccttac | gcatctgtgc | ggtatttcac | accgcatacg | tcaaagcaac | 2220 |
| catagtacgc | gccctgtagc | ggcgcattaa | gcgcggcggg | tgtggtggtt | acgcgcagcg | 2280 |
| tgaccgctac | acttgccagc | gccctagcgc | ccgctccttt | cgctttcttc | ccttcctttc | 2340 |
| tcgccacgtt | cgccggcttt | ccccgtcaag | ctctaaatcg | ggggctccct | ttagggttcc | 2400 |
| gatttagtgc | tttacggcac | ctcgaccccca | aaaaacttga | tttgggtgat | ggttcacgta | 2460 |
| gtgggccatc | gccctgatag | acggtttttc | gccctttgac | gttggagtcc | acgttcttta | 2520 |
| atagtggact | cttgttccaa | actggaacaa | cactcaaccc | tatctcgggc | tattcttttg | 2580 |
| atttataagg | gattttgccg | atttcggcct | attggttaaa | aaatgagctg | atttaacaaa | 2640 |
| aatttaacgc | gaattttaac | aaaatattaa | cgtttacaat | tttatggtgc | actctcagta | 2700 |
| caatctgctc | tgatgccgca | tagttaagcc | agccccgaca | cccgccaaca | cccgctgacg | 2760 |
| cgccctgacg | ggcttgtctg | ctcccggcat | ccgcttacag | acaagctgtg | accgtctccg | 2820 |
| ggagctgcat | gtgtcagagg | ttttcaccgt | catcaccgaa | acgcgcgaga | cgaaagggcc | 2880 |
| tcgtgatacg | cctatttta | taggttaatg | tcatgataat | aatggtttct | tagacgtcag | 2940 |
| gtggcacttt | tcggggaaat | gtgcgcggaa | cccctatttg | tttatttttc | taaatacatt | 3000 |
| caaatatgta | tccgctcatg | agacaataac | cctgataaat | gcttcaataa | tattgaaaaa | 3060 |
| ggaagagtat | gagtattcaa | catttccgtg | tcgcccttat | ccctttttt | gcggcatttt | 3120 |
| gccttcctgt | ttttgctcac | ccagaaacgc | tggtgaaagt | aaaagatgct | gaagatcagt | 3180 |
| tgggtgcacg | agtgggttac | atcgaactgg | atctcaacag | cggtaagatc | cttgagagtt | 3240 |
| ttcgccccga | agaacgtttt | ccaatgatga | gcacttttaa | agttctgcta | tgtggcgcgg | 3300 |
| tattatcccg | tattgacgcc | gggcaagagc | aactcggtcg | ccgcatacac | tattctcaga | 3360 |
| atgacttggt | tgagtactca | ccagtcacag | aaaagcatct | tacggatggc | atgacagtaa | 3420 |

```
gagaattatg cagtgctgcc ataaccatga gtgataacac tgcggccaac ttacttctga    3480
caacgatcgg aggaccgaag gagctaaccg cttttttgca caacatgggg gatcatgtaa    3540
ctcgccttga tcgttgggaa ccggagctga atgaagccat accaaacgac gagcgtgaca    3600
ccacgatgcc tgtagcaatg gcaacaacgt tgcgcaaact attaactggc gaactactta    3660
ctctagcttc ccggcaacaa ttaatagact ggatggaggc ggataaagtt gcaggaccac    3720
ttctgcgctc ggcccttccg gctggctggt ttattgctga taaatctgga gccggtgagc    3780
gtgggtctcg cggtatcatt gcagcactgg ggccagatgg taagccctcc cgtatcgtag    3840
ttatctacac gacggggagt caggcaacta tggatgaacg aaatagacag atcgctgaga    3900
taggtgcctc actgattaag cattggtaac tgtcagacca agtttactca tatatacttt    3960
agattgattt aaaacttcat ttttaattta aaaggatcta ggtgaagatc ctttttgata    4020
atctcatgac caaaatccct aacgtgagt tttcgttcca ctgagcgtca gaccccgtag    4080
aaaagatcaa aggatcttct tgagatcctt ttttttctgcg cgtaatctgc tgcttgcaaa    4140
caaaaaaacc accgctacca gcggtggttt gtttgccgga tcaagagcta ccaactcttt    4200
ttccgaaggt aactggcttc agcagagcgc agataccaaa tactgtcctt ctagtgtagc    4260
cgtagttagg ccaccacttc aagaactctg tagcaccgcc tacatacctc gctctgctaa    4320
tcctgttacc agtggctgct gccagtggcg ataagtcgtg tcttaccggg ttggactcaa    4380
gacgatagtt accggataag gcgcagcggt cgggctgaac ggggggttcg tgcacacagc    4440
ccagcttgga gcgaacgacc tacaccgaac tgagatacct acagcgtgag ctatgagaaa    4500
gcgccacgct tcccgaaggg agaaaggcgg acaggtatcc ggtaagcggc agggtcggaa    4560
caggagagcg cacgagggag cttccagggg gaaacgcctg gtatctttat agtcctgtcg    4620
ggtttcgcca cctctgactt gagcgtcgat ttttgtgatg ctcgtcaggg gggcggagcc    4680
tatgaaaaaa cgccagcaac gcggcctttt tacggttcct ggccttttgc tggccttttg    4740
ctcacatgtt ctttcctgcg ttatcccctg attctgtgga taaccgtatt accgcctttg    4800
agtgagctga taccgctcgc cgcagccgaa cgaccgagcg cagcgagtca gtgagcgagg    4860
aagcggaag                                                           4869
```

<210> SEQ ID NO 22
<211> LENGTH: 4860
<212> TYPE: DNA
<213> ORGANISM: Artificial Sequence
<220> FEATURE:
<223> OTHER INFORMATION: Description of Artificial Sequence: Synthetic
      pHen-sdAb Nef19 polynucleotide

<400> SEQUENCE: 22

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
catgcaaatt ctatttcaag gagacagtca taatgaaata cctattgcct acggcagccg     300
ctggattgtt attactcgcg gcccagccgg ccatggccga ggtgcagctg gtggagtctg     360
ggggaggctt ggtgcaggct gggggctctc tgagactctt ctgtgcggcc tctggattca     420
ccttcggtac cagtaatatg gcctggctcc gccaggctcc agggaagcgt cgcgagtggg     480
tcgcacttat tacgattagt ggctacacag actatgcaga ctccgtgaag gaccgattca     540
```

```
ccatatccag agacaacgcc aagaacacgg tgtctctgca aatgaacagc ctgaaacctg    600
aggacacggc catttatttt tgcgcccggc gtgtagggtc tgagtatgat tgtggggcc     660 aggggaccca ggtcactgtc tcctcagcgg ccgcagaaca aaaactcatc tcagaagagg    720
atctgaatgg ggccgcacat caccaccatc accatgggag ctagactgtt gaaagttgtt    780
tagcaaaacc tcatacagaa aattcattta ctaacgtctg gaaagacgac aaaactttag    840
atcgttacgc taactatgag ggctgtctgt ggaatgctac aggcgttgtg gtttgtactg    900
gtgacgaaac tcagtgttac ggtacatggg ttcctattgg gcttgctatc cctgaaaatg    960
agggtggtgc tctgagggt ggcggttctg agggtggcgg ttctgagggt ggcggtacta     1020
aacctcctga gtacggtgat acacctattc cgggctatac ttatatcaac cctctcgacg    1080
gcacttatcc gcctggtact gagcaaaacc ccgctaatcc taatccttct cttgaggagt    1140
ctcagcctct taatactttc atgtttcaga ataataggtt ccgaaatagg cagggtgcat    1200
taactgttta tacgggcact gttactcaag gcactgaccc cgttaaaact tattaccagt    1260
acactcctgt atcatcaaaa gccatgtatg acgcttactg gaacggtaaa ttcagagact    1320
gcgctttcca ttctggcttt aatgaggatc cattcgtttg tgaatatcaa ggccaatcgt    1380
ctgacctgcc tcaacctcct gtcaatgctg gcggcggctc tggtggtggt tctggtggcg    1440
gctctgaggg tggcggctct gagggtggcg gttctgaggg tggcggctct gagggtggcg    1500
gttccggtgg cggctccggt tccggtgatt ttgattatga aaaaatggca aacgctaata    1560
agggggctat gaccgaaaat gccgatgaaa acgcgctaca gtctgacgct aaaggcaaac    1620
ttgattctgt cgctactgat tacggtgctg ctatcgatgg tttcattggt gacgtttccg    1680
gccttgctaa tggtaatggt gctactggtg attttgctgg ctctaattcc caaatggctc    1740
aagtcggtga cggtgataat tcacctttaa tgaataattt ccgtcaatat ttaccttctt    1800
tgcctcagtc ggttgaatgt cgcccttatg tctttggcgc tggtaaacca tatgaatttt    1860
ctattgattg tgacaaaata aacttattcc gtggtgtctt tgcgtttctt ttatatgttg    1920
ccacctttat gtatgtattt tcgacgtttg ctaacatact gcgtaataag gagtcttaat    1980
aagaattcac tggccgtcgt tttacaacgt cgtgactggg aaaaccctgg cgttacccaa    2040
cttaatcgcc ttgcagcaca tccccctttc gccagctggc gtaatagcga agaggcccgc    2100
accgatcgcc cttcccaaca gttgcgcagc ctgaatggcg aatggcgcct gatgcggtat    2160
tttctcctta cgcatctgtg cggtatttca caccgcatac gtcaaagcaa ccatagtacg    2220
cgccctgtag cggcgcatta agcgcggcgg gtgtggtggt tacgcgcagc gtgaccgcta    2280
cacttgccag cgccctagcg cccgctcctt tcgctttctt cccttccttt ctcgccacgt    2340
tcgccggctt tccccgtcaa gctctaaatc ggggctccc tttagggttc cgatttagtg     2400
ctttacggca cctcgacccc aaaaaacttg atttgggtga tggttcacgt agtgggccat    2460
cgccctgata acggtttttc gccctttga cgttggagtc cacgttcttt aatagtggac      2520
tcttgttcca aactggaaca acactcaacc ctatctcggg ctattctttt gatttataag    2580
ggattttgcc gatttcggcc tattggttaa aaaatgagct gatttaacaa aaatttaacg    2640
cgaattttaa caaaatatta cgtttacaa ttttatggtg cactctcagt acaatctgct      2700
ctgatgccgc atagttaagc cagccccgac acccgccaac cccgctgacg cgccctgac      2760 gggcttgtct gctcccggca tccgcttaca gacaagctgt gaccgtctcc gggagctgca    2820
tgtgtcagag gttttcaccg tcatcaccga aacgcgcgag acgaaagggc ctcgtgatac    2880
```

```
gcctattttt ataggttaat gtcatgataa aatggtttc ttagacgtca ggtggcactt      2940
ttcggggaaa tgtgcgcgga accctattt gtttatttt ctaaatacat tcaaatatgt       3000
atccgctcat gagacaataa ccctgataaa tgcttcaata atattgaaaa aggaagagta     3060
tgagtattca acatttccgt gtcgcccta ttccttttt tgcggcattt tgccttcctg       3120
tttttgctca cccagaaacg ctggtgaaag taaaagatgc tgaagatcag ttgggtgcac     3180
gagtgggtta catcgaactg gatctcaaca gcggtaagat ccttgagagt tttcgccccg     3240
aagaacgttt tccaatgatg agcacttta aagttctgct atgtggcgcg gtattatccc     3300
gtattgacgc cgggcaagag caactcggtc gccgcataca ctattctcag aatgacttgg    3360
ttgagtactc accagtcaca gaaaagcatc ttacggatgg catgacagta agagaattat    3420
gcagtgctgc cataaccatg agtgataaca ctgcggccaa cttacttctg acaacgatcg    3480
gaggaccgaa ggagctaacc gcttttttgc acaacatggg gatcatgta actcgccttg     3540 atcgttggga accggagctg aatgaagcca taccaaacga cgagcgtgac accacgatgc    3600
ctgtagcaat ggcaacaacg ttgcgcaaac tattaactgg cgaactactt actctagctt    3660
cccggcaaca attaatagac tggatggagg cggataaagt tgcaggacca cttctgcgct    3720 cggccttcc ggctggctgg tttattgctg ataaatctgg agccggtgag cgtgggtctc     3780
gcggtatcat tgcagcactg gggccagatg gtaagccctc ccgtatcgta gttatctaca    3840
cgacggggag tcaggcaact atggatgaac gaaatagaca gatcgctgag ataggtgcct    3900
cactgattaa gcattggtaa ctgtcagacc aagtttactc atatatactt tagattgatt    3960
taaaacttca ttttaattt aaaaggatct aggtgaagat ccttttgat aatctcatga      4020 ccaaaatccc ttaacgtgag ttttcgttcc actgagcgtc agaccccgta gaaaagatca    4080
aaggatcttc ttgagatcct ttttttctgc gcgtaatctg ctgcttgcaa acaaaaaaac    4140
caccgctacc agcggtggtt tgtttgccgg atcaagagct accaactctt tttccgaagg    4200
taactggctt cagcagagcg cagataccaa atactgtcct tctagtgtag ccgtagttag    4260
gccaccactt caagaactct gtagcaccgc ctacatacct cgctctgcta atcctgttac    4320
cagtggctgc tgccagtggc gataagtcgt gtcttaccgg gttggactca agacgatagt    4380
taccggataa ggcgcagcgg tcgggctgaa cggggggttc gtgcacacag cccagcttgg    4440
agcgaacgac ctacaccgaa ctgagatacc tacagcgtga gctatgagaa agcgccacgc    4500
ttcccgaagg gagaaaggcg gacaggtatc cggtaagcgg cagggtcgga acaggagagc    4560
gcacgaggga gcttccaggg ggaaacgcct ggtatcttta tagtcctgtc gggtttcgcc    4620
acctctgact tgagcgtcga ttttgtgat gctcgtcagg ggcggagc ctatggaaaa       4680 acgccagcaa cgcggccttt ttacggttcc tggccttttg ctggcctttt gctcacatgt    4740
tctttcctgc gttatcccct gattctgtgg ataaccgtat taccgccttt gagtgagctg    4800
ataccgctcg ccgcagccga acgaccgagc gcagcgagtc agtgagcgag gaagcggaag    4860
```

<210> SEQ ID NO 23
<211> LENGTH: 4860
<212> TYPE: DNA
<213> ORGANISM: Artificial Sequence
<220> FEATURE:
<223> OTHER INFORMATION: Description of Artificial Sequence: Synthetic
      pHen-sdAb Nef20 polynucleotide

<400> SEQUENCE: 23

```
agcgcccaat acgcaaaccg cctctccccg cgcgttggcc gattcattaa tgcagctggc        60
```

```
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
catgcaaatt ctatttcaag agacagtca taatgaaata cctattgcct acggcagccg    300
ctggattgtt attactcgcg gcccagccgg ccatggccga ggtgcagctg gtggagtctg    360
ggggaggctt ggtgcaggct gggggctctc tgagactctt ctgtgcggcc tctggattca    420
ccttcggtac cagtaatatg gcctggctcc gccaggctcc agggaagcgt cgcgagtggg    480
tcgcacttat tacgattagt ggctacacag actatgcaga ctccgtgaag gaccgattca    540
ccatatccag agacaacgcc aagaacacgg tgtctctgca aatgaacagc ctgaaacctg    600
aggacacggc catttatttt tgcgcccggc gtgtagggtc tgagtatgat ttgtggggcc    660
aggggaccca ggtcactgtc tcctcagcgg ccgcagaaca aaaactcatc tcagaagagg    720
atctgaatgg ggccgcacat caccaccatc accatgggag ctagactgtt gaaagttgtt    780
tagcaaaacc tcatacagaa aattcattta ctaacgtctg gaaagacgac aaaactttag    840
atcgttacgc taactatgag ggctgtctgt ggaatgctac aggcgttgtg gtttgtactg    900
gtgacgaaac tcagtgttac ggtacatggg ttcctattgg gcttgctatc cctgaaaatg    960
agggtggtgg ctctgagggt ggcggttctg agggtggcgg ttctgagggt ggcggtacta   1020
aacctcctga gtacggtgat acacctattc cgggctatac ttatatcaac cctctcgacg   1080
gcacttatcc gcctggtact gagcaaaacc ccgctaatcc taatccttct cttgaggagt   1140
ctcagcctct taatactttc atgtttcaga ataataggtt ccgaaatagg cagggtgcat   1200
taactgttta tacgggcact gttactcaag gcactgaccc cgttaaaact tattaccagt   1260
acactcctgt atcatcaaaa gccatgtatg acgcttactg gaacggtaaa ttcagagact   1320
gcgctttcca ttctggcttt aatgaggatc cattcgtttg tgaatatcaa ggccaatcgt   1380
ctgacctgcc tcaacctcct gtcaatgctg gcggcggctc tggtggtggt tctggtggcg   1440
gctctgaggg tggcggctct gagggtggcg ttctgaggg tggcggctct gagggtggcg   1500
gttccggtgg cggctccggt tccggtgatt ttgattatga aaaaatggca aacgctaata   1560
agggggctat gaccgaaaat gccgatgaaa acgcgctaca gtctgacgct aaaggcaaac   1620
ttgattctgt cgctactgat tacggtgctg ctatcgatgg tttcattggt gacgtttccg   1680
gccttgctaa tggtaatggt gctactggtg attttgctgg ctctaattcc caaatggctc   1740
aagtcggtga cggtgataat tcacctttaa tgaataattt ccgtcaatat ttaccttctt   1800
tgcctcagtc ggttgaatgt cgcccttatg tctttggcgc tggtaaacca tatgaatttt   1860
ctattgattg tgacaaaata aacttattcc gtggtgtctt tgcgtttctt ttatatgttg   1920
ccacctttat gtatgtattt tcgacgtttg ctaacatact gcgtaataag gagtcttaat   1980
aagaattcac tggccgtcgt tttacaacgt cgtgactggg aaaaccctgg cgttacccaa   2040
cttaatcgcc ttgcagcaca tccccctttc gccagctggc gtaatagcga agaggcccgc   2100
accgatcgcc cttcccaaca gttgcgcagc ctgaatggcg aatggcgcct gatgcggtat   2160
tttctcctta cgcatctgtg cggtatttca caccgcatac gtcaaagcaa ccatagtacg   2220
cgccctgtag cggcgcatta agcgcggcgg gtgtggtggt tacgcgcagc gtgaccgcta   2280
cacttgccag cgccctagcg cccgctcctt tcgctttctt cccttccttt ctcgccacgt   2340
tcgccggctt tccccgtcaa gctctaaatc ggggcctccc tttagggttc cgatttagtg   2400
ctttacggca cctcgacccc aaaaaacttg atttgggtga tggttcacgt agtgggccat   2460
```

```
cgccctgata gacggttttt cgccctttga cgttggagtc cacgttcttt aatagtggac    2520
tcttgttcca aactggaaca acactcaacc ctatctcggg ctattctttt gatttataag    2580
ggattttgcc gatttcggcc tattggttaa aaatgagct gatttaacaa aaatttaacg     2640
cgaattttaa caaatatta acgtttacaa ttttatggtg cactctcagt acaatctgct     2700
ctgatgccgc atagttaagc cagccccgac acccgccaac acccgctgac gcgccctgac    2760
gggcttgtct gctcccggca tccgcttaca gacaagctgt gaccgtctcc gggagctgca    2820
tgtgtcagag gttttcaccg tcatcaccga aacgcgcgag acgaaagggc ctcgtgatac    2880 gcctatttt ataggttaat gtcatgataa taatggtttc ttagacgtca ggtggcactt     2940
ttcggggaaa tgtgcgcgga acccctattt gtttatttt ctaaatacat tcaaatatgt    3000
atccgctcat gagacaataa ccctgataaa tgcttcaata atattgaaaa aggaagagta    3060
tgagtattca acatttccgt gtcgccctta ttcccttttt tgcggcattt tgccttcctg    3120
tttttgctca cccagaaacg ctggtgaaag taaaagatgc tgaagatcag ttgggtgcac    3180
gagtgggtta catcgaactg gatctcaaca gcggtaagat ccttgagagt tttcgccccg    3240
aagaacgttt tccaatgatg agcacttta aagttctgct atgtggcgcg gtattatccc    3300
gtattgacgc cgggcaagag caactcggtc gccgcataca ctattctcag aatgacttgg    3360
ttgagtactc accagtcaca gaaaagcatc ttacgatgg catgacagta agagaattat    3420
gcagtgctgc cataaccatg agtgataaca ctgcggccaa cttacttctg acaacgatcg    3480
gaggaccgaa ggagctaacc gcttttttgc acaacatggg ggatcatgta actcgccttg    3540
atcgttggga accggagctg aatgaagcca taccaaacga cgagcgtgac accacgatgc    3600
ctgtagcaat ggcaacaacg ttgcgcaaac tattaactgg cgaactactt actctagctt    3660
cccggcaaca attaatagac tggatggagg cggataaagt tgcaggacca cttctgcgct    3720
cggcccttcc ggctggctgg tttattgctg ataaatctgg agccggtgag cgtgggtctc    3780
gcggtatcat tgcagcactg gggccagatg gtaagccctc ccgtatcgta gttatctaca    3840
cgacggggag tcaggcaact atggatgaac gaaatagaca gatcgctgag ataggtgcct    3900
cactgattaa gcattggtaa ctgtcagacc aagtttactc atatatactt tagattgatt    3960
taaaacttca ttttaatttt aaaaggatct aggtgaagat ccttttgat aatctcatga    4020 ccaaaatccc ttaacgtgag ttttcgttcc actgagcgtc agaccccgta gaaaagatca    4080
aaggatcttc ttgagatcct ttttttctgc gcgtaatctg ctgcttgcaa acaaaaaaac    4140
caccgctacc agcggtggtt tgtttgccgg atcaagagct accaactctt tttccgaagg    4200
taactggctt cagcagagcg cagataccaa atactgtcct tctagtgtag ccgtagttag    4260
gccaccactt caagaactct gtagcaccgc ctacatacct cgctctgcta atcctgttac    4320
cagtggctgc tgccagtggc gataagtcgt gtcttaccgg gttggactca agacgatagt    4380
taccggataa ggcgcagcgg tcgggctgaa cggggggttc gtgcacacag cccagcttgg    4440
agcgaacgac ctacaccgaa ctgagatacc tacagcgtga gctatgagaa agcgccacgc    4500
ttcccgaagg gagaaaggcg gacaggtatc cggtaagcgg cagggtcgga acaggagagc    4560
gcacgaggga gcttccaggg ggaaacgcct ggtatcttta tagtcctgtc gggtttcgcc    4620
acctctgact tgagcgtcga ttttttgtgat gctcgtcagg gggcggagc ctatggaaaa    4680 acgccagcaa cgcggccttt ttacggttcc tggcctttg ctggcctttt gctcacatgt    4740
tctttcctgc gttatcccct gattctgtgg ataaccgtat taccgccttt gagtgagctg    4800
```
ataccgctcg ccgcagccga acgaccgagc gcagcgagtc agtgagcgag gaagcggaag    4860

<210> SEQ ID NO 24
<211> LENGTH: 4942
<212> TYPE: DNA
<213> ORGANISM: Artificial Sequence
<220> FEATURE:
<223> OTHER INFORMATION: Description of Artificial Sequence: Synthetic
      pET-sdAb Nef1 polynucleotide

<400> SEQUENCE: 24
cgtcggccgc catgccggcg ataatggcct gcttctcgcc gaaacgtttg gtggcgggac      60
cagtgacgaa ggcttgagcg agggcgtgca agattccgaa taccgcaagc gacaggccga    120
tcatcgtcgc gctccagcga aagcggtcct cgccgaaaat gacccagagc gctgccggca    180
cctgtcctac gagttgcatg ataaagaaga cagtcataag tgcggcgacg atagtcatgc    240
cccgcgccca ccggaaggag ctgactgggt tgaaggctct caagggcatc ggtcgacgct    300
ctcccttatg cgactcctgc attaggaagc agcccagtag taggttgagg ccgttgagca    360
ccgccgccgc aaggaatggt gcatgcaagg agatggcgcc caacagtccc ccggccacgg    420
ggcctgccac catacccacg ccgaaacaag cgctcatgag cccgaagtgg cgagcccgat    480
cttccccatc ggtgatgtcg gcgatatagg cgccagcaac cgcacctgtg gcgccggtga    540
tgccggccac gatgcgtccg gcgtagagga tcgagatctc gatcccgcga aattaatacg    600
actcactata gggagaccac aacggtttcc ctctagaaat aattttgttt aactttaaga    660
aggagatata ccatggccga ggtgcagctg gtggagtctg ggggaggctt ggtgcagcct    720
ggggggtctc tgaaactctc ctgtgcagcc tctggaagca tcttcagagc caatgccatg    780
cgctggtacc gccaggctcc aggaaaacag cgcgagtggg tcgcaagtgt tattagtgat    840
gatttcacag actatgtaga ctctgtgagg ggccgattca ccatctccaa agacaacgcc    900
cagaacacgg tgtatctcca aatgaacagc ctgaaacctg aggacacggc cgtctattac    960
tgtaatgcgc aactcggcgg agtcaactac tggggccagg ggacccaggt caccgtctcc   1020
tcagcggccg cacaccacca tcatcatcac ggatcctaag cttgctgagc aataactagc   1080
ataacccctt ggggcctcta aacgggtctt gaggggtttt tgctgaaag gaggaactat   1140 atccggatat ccacaggacg ggtgtggtcg ccatgatcgc gtagtcgata gtggctccaa   1200
gtagcgaagc gagcaggact gggcggcggc caaagcggtc ggacagtgct ccgagaacgg   1260
gtgcgcatag aaattgcatc aacgcatata gcgctagcag cacgccatag tgactggcga   1320
tgctgtcgga atggacgata tcccgcaaga ggcccggcag taccggcata accaagccta   1380
tgcctacagc atccagggtg acggtgccga ggatgacgat gagcgcattg ttagatttca   1440
tacacggtgc ctgactgcgt tagcaattta actgtgataa actaccgcat taaagcttat   1500
cgatgataag ctgtcaaaca tgagaattct tgaagacgaa agggcctcgt gatacgccta   1560
tttttatagg ttaatgtcat gataataatg gtttcttaga cgtcaggtgg cacttttcgg   1620
ggaaatgtgc gcggaacccc tatttgttta ttttctaaa tacattcaaa tatgtatccg   1680
ctcatgagac aataaccctg ataaatgctt caataatatt gaaaaaggaa gagtatgagt   1740
attcaacatt tccgtgtcgc ccttattccc ttttttgcgg catttttgcct tcctgttttt   1800 gctcacccag aaacgctggt gaaagtaaaa gatgctgaag atcagttggg tgcacgagtg   1860
ggttacatcg aactggatct caacagcggt aagatccttg agagttttcg ccccgaagaa   1920
cgttttccaa tgatgagcac ttttaaagtt ctgctatgtg gcgcggtatt atcccgtgtt   1980

-continued

```
gacgccgggc aagagcaact cggtcgccgc atacactatt ctcagaatga cttggttgag   2040
tactcaccag tcacagaaaa gcatcttacg gatggcatga cagtaagaga attatgcagt   2100
gctgccataa ccatgagtga taacactgcg gccaacttac ttctgacaac gatcggagga   2160
ccgaaggagc taaccgcttt tttgcacaac atgggggatc atgtaactcg ccttgatcgt   2220
tgggaaccgg agctgaatga agccatacca aacgacgagc gtgacaccac gatgcctgca   2280
gcaatggcaa caacgttgcg caaactatta actggcgaac tacttactct agcttcccgg   2340
caacaattaa tagactggat ggaggcggat aaagttgcag gaccacttct gcgctcggcc   2400
cttccggctg gctggtttat tgctgataaa tctggagccg gtgagcgtgg gtctcgcggt   2460
atcattgcag cactggggcc agatggtaag ccctcccgta tcgtagttat ctacacgacg   2520
gggagtcagg caactatgga tgaacgaaat agacagatcg ctgagatagg tgcctcactg   2580
attaagcatt ggtaactgtc agaccaagtt tactcatata ctttagat tgatttaaaa     2640
cttcattttt aatttaaaag gatctaggtg aagatccttt ttgataatct catgaccaaa   2700
atcccttaac gtgagttttc gttccactga gcgtcagacc ccgtagaaaa gatcaaagga   2760
tcttcttgag atcctttttt tctgcgcgta atctgctgct tgcaaacaaa aaaaccaccg   2820
ctaccagcgg tggtttgttt gccggatcaa gagctaccaa ctcttttcc gaaggtaact    2880
ggcttcagca gagcgcagat accaaatact gtccttctag tgtagccgta gttaggccac   2940
cacttcaaga actctgtagc accgcctaca tacctcgctc tgctaatcct gttaccagtg   3000
gctgctgcca gtggcgataa gtcgtgtctt accgggttgg actcaagacg atagttaccg   3060
gataaggcgc agcggtcggg ctgaacgggg gttcgtgca cacagcccag cttggagcga   3120
acgacctaca ccgaactgag atacctacag cgtgagctat gagaaagcgc cacgcttccc   3180
gaagggagaa aggcggacag gtatccggta agcggcaggg tcggaacagg agagcgcacg   3240
agggagcttc caggggggaaa cgcctggtat ctttatagtc ctgtcgggtt tcgccacctc   3300
tgacttgagc gtcgattttt gtgatgctcg tcagggggc ggagcctatg gaaaaacgcc    3360
agcaacgcgg ccttttttacg gttcctggcc ttttgctggc cttttgctca catgttcttt   3420
cctgcgttat cccctgattc tgtggataac cgtattaccg cctttgagtg agctgatacc   3480
gctcgccgca gccgaacgac cgagcgcagc gagtcagtga gcgaggaagc ggaagagcgc   3540
ctgatgcggt attttctcct tacgcatctg tgcggtattt cacaccgcat atatggtgca   3600
ctctcagtac aatctgctct gatgccgcat agttaagcca gtatacactc cgctatcgct   3660
acgtgactgg gtcatggctg cgccccgaca cccgccaaca cccgctgacg cgccctgacg   3720
ggcttgtctg ctcccggcat ccgcttacag acaagctgtg accgtctccg ggagctgcat   3780
gtgtcagagg ttttcaccgt catcaccgaa acgcgcgagg cagctgcggt aaagctcatc   3840
agcgtggtcg tgaagcgatt cacagatgtc tgcctgttca tccgcgtcca gctcgttgag   3900
tttctccaga agcgttaatg tctggcttct gataaagcgg ccatgttaa gggcggtttt    3960
ttcctgtttg gtcactgatg cctccgtgta aggggggattt ctgttcatgg gggtaatgat   4020
accgatgaaa cgagagagga tgctcacgat acgggttact gatgatgaac atgcccggtt   4080
actgaacgt tgtgagggta aacaactggc ggtatggatg cggcgggacc agagaaaaat    4140
cactcagggt caatgccagc gcttcgttaa tacagatgta ggtgttccac agggtagcca   4200
gcagcatcct gcgatgcaga tccggaacat aatggtgcag ggcgctgact ccgcgtttc    4260
cagactttac gaaacacgga aaccgaagac cattcatgtt gttgctcagg tcgcagacgt   4320
tttgcagcag cagtcgcttc acgttcgctc gcgtatcggt gattcattct gctaaccagt   4380
```

```
aaggcaaccc cgccagccta gccgggtcct caacgacagg agcacgatca tgcgcacccg    4440
tggccaggac ccaacgctgc ccgagatgcg ccgcgtgcgg ctgctggaga tggcggacgc    4500
gatggatatg ttctgccaag ggttggtttg cgcattcaca gttctccgca agaattgatt    4560
ggctccaatt cttggagtgg tgaatccgtt agcgaggtgc cgccggcttc cattcaggtc    4620
gaggtggccc ggctccatgc accgcgacgc aacgcgggga ggcagacaag gtatagggcg    4680
gcgcctacaa tccatgccaa cccgttccat gtgctcgccg aggcggcata aatcgccgtg    4740
acgatcagcg gtccagtgat cgaagttagg ctggtaagag ccgcgagcga tccttgaagc    4800
tgtccctgat ggtcgtcatc tacctgcctg gacagcatgg cctgcaacgc gggcatcccg    4860
atgccgccgg aagcgagaag aatcataatg gggaaggcca tccagcctcg cgtcgcgaac    4920
gccagcaaga cgtagcccag cg                                              4942
```

<210> SEQ ID NO 25
<211> LENGTH: 4954
<212> TYPE: DNA
<213> ORGANISM: Artificial Sequence
<220> FEATURE:
<223> OTHER INFORMATION: Description of Artificial Sequence: Synthetic
      pET-sdAb Nef2 polynucleotide

<400> SEQUENCE: 25

```
cgtcggccgc catgccggcg ataatggcct gcttctcgcc gaaacgtttg gtggcgggac      60
cagtgacgaa ggcttgagcg agggcgtgca agattccgaa taccgcaagc gacaggccga     120
tcatcgtcgc gctccagcga aagcggtcct cgccgaaaat gacccagagc gctgccggca     180
cctgtcctac gagttgcatg ataaagaaga cagtcataag tgcggcgacg atagtcatgc     240
cccgcgccca ccggaaggag ctgactgggt tgaaggctct caagggcatc ggtcgacgct     300
ctcccttatg cgactcctgc attaggaagc agcccagtag taggttgagg ccgttgagca     360
ccgccgccgc aaggaatggt gcatgcaagg agatggcgcc caacagtccc ccggccacgg     420
ggcctgccac catacccacg ccgaaacaag cgctcatgag cccgaagtgg cgagcccgat     480
cttccccatc ggtgatgtcg gcgatatagg cgccagcaac cgcacctgtg gcgccggtga     540
tgccggccac gatgcgtccg gcgtagagga tcgagatctc gatcccgcga aattaatacg     600
actcactata gggagaccac aacggtttcc ctctagaaat aattttgttt aactttaaga     660
aggagatata ccatggccga ggtgcagctg gtggagtctg ggggaggctt ggtgcaggct     720
ggagggtctc tgatactctc ctgtgcaacc tctggtagga tcttcggtat caatgccatg     780
ggctggtacc gccaggctcc agggaaggag cgcgagttgg tcgcagttat taccagtggt     840
ggaaacacaa actatgcaga ctccgtgaag ggccgattca ccatctccaa agacaatgcc     900
aagaacacgc tgtatctgca aatgaatagc ctgaaatttg aggacacggc ccggtactac     960
tgtgtgagat ccctccctgg gtggttctac ggcatggact actggggcaa agggacccag    1020
gtcaccgtct cctcagcggc cgcacaccac catcatcatc acggatccta agcttgctga    1080
gcaataacta gcataacccc ttggggcctc taaacgggtc ttgaggggtt ttttgctgaa    1140
aggaggaact atatccggat atccacagga cgggtgtggt cgccatgatc gcgtagtcga    1200
tagtggctcc aagtagcgaa gcgagcagga ctgggcggcg ccaaagcgg tcggacagtg     1260 ctccgagaac gggtgcgcat agaaattgca tcaacgcata tagcgctagc agcacgccat    1320
agtgactggc gatgctgtcg gaatggacga tatcccgcaa gaggcccggc agtaccggca    1380
taaccaagcc tatgcctaca gcatccaggg tgacggtgcc gaggatgacg atgagcgcat    1440
```

```
tgttagattt catacacggt gcctgactgc gttagcaatt taactgtgat aaactaccgc    1500
attaaagctt atcgatgata agctgtcaaa catgagaatt cttgaagacg aaagggcctc    1560
gtgatacgcc tatttttata ggttaatgtc atgataataa tggtttctta gacgtcaggt    1620
ggcacttttc ggggaaatgt gcgcggaacc cctatttgtt tattttttcta aatacattca    1680 aatatgtatc cgctcatgag acaataaccc tgataaatgc ttcaataata ttgaaaaagg    1740
aagagtatga gtattcaaca tttccgtgtc gcccttattc ccttttttgc ggcattttgc    1800
cttcctgttt ttgctcaccc agaaacgctg gtgaaagtaa aagatgctga agatcagttg    1860
ggtgcacgag tgggttacat cgaactggat ctcaacagcg gtaagatcct tgagagtttt    1920
cgccccgaag aacgttttcc aatgatgagc acttttaaag ttctgctatg tggcgcggta    1980
ttatcccgtg ttgacgccgg gcaagagcaa ctcggtcgcc gcatacacta ttctcagaat    2040
gacttggttg agtactcacc agtcacagaa aagcatctta cggatggcat gacagtaaga    2100
gaattatgca gtgctgccat aaccatgagt gataacactg cggccaactt acttctgaca    2160
acgatcggag gaccgaagga gctaaccgct tttttgcaca acatggggga tcatgtaact    2220
cgccttgatc gttgggaacc ggagctgaat gaagccatac caaacgacga gcgtgacacc    2280
acgatgcctg cagcaatggc aacaacgttg cgcaaactat taactggcga actacttact    2340
ctagcttccc ggcaacaatt aatagactgg atggaggcgg ataaagttgc aggaccactt    2400
ctgcgctcgg cccttccggc tggctggttt attgctgata aatctggagc cggtgagcgt    2460
gggtctcgcg gtatcattgc agcactgggg ccagatggta agccctcccg tatcgtagtt    2520
atctacacga cggggagtca ggcaactatg gatgaacgaa atagacagat cgctgagata    2580
ggtgcctcac tgattaagca ttggtaactg tcagaccaag tttactcata tactttag     2640 attgatttaa aacttcattt ttaatttaaa aggatctagg tgaagatcct tttgataat    2700 ctcatgacca aaatccctta acgtgagttt cgttccact gagcgtcaga ccccgtagaa     2760
aagatcaaag gatcttcttg agatccttt tttctgcgcg taatctgctg cttgcaaaca    2820
aaaaaaccac cgctaccagc ggtggtttgt ttgccggatc aagagctacc aactcttttt    2880
ccgaaggtaa ctggcttcag cagagcgcag ataccaaata ctgtccttct agtgtagccg    2940
tagttaggcc accacttcaa gaactctgta gcaccgccta catacctcgc tctgctaatc    3000
ctgttaccag tggctgctgc cagtggcgat aagtcgtgtc ttaccgggtt ggactcaaga    3060
cgatagttac cggataaggc gcagcggtcg ggctgaacgg ggggttcgtg cacacagccc    3120
agcttggagc gaacgaccta caccgaactg agatacctac agcgtgagct atgagaaagc    3180
gccacgcttc ccgaagggag aaaggcggac aggtatccgg taagcggcag gtcggaaca     3240 ggagagcgca cgagggagct tccagggga aacgcctggt atctttatag tcctgtcggg    3300
tttcgccacc tctgacttga gcgtcgattt ttgtgatgct cgtcaggggg cggagccta     3360 tggaaaaacg ccagcaacgc ggcctttta cggttcctgg ccttttgctg gcttttgct     3420 cacatgttct ttcctgcgtt atcccctgat tctgtggata accgtattac cgcctttgag    3480
tgagctgata ccgctcgccg cagccgaacg accgagcgca gcgagtcagt gagcgaggaa    3540
gcggaagagc gcctgatgcg gtattttctc cttacgcatc tgtgcggtat ttcacaccgc    3600
atatatggtg cactctcagt acaatctgct ctgatgccgc atagttaagc cagtatacac    3660
tccgctatcg ctacgtgact gggtcatggc tgcgccccga cacccgccaa cacccgctga    3720
cgcgccctga cgggcttgtc tgctcccggc atccgcttac agacaagctg tgaccgtctc    3780
```

```
cgggagctgc atgtgtcaga ggttttcacc gtcatcaccg aaacgcgcga ggcagctgcg      3840
gtaaagctca tcagcgtggt cgtgaagcga ttcacagatg tctgcctgtt catccgcgtc      3900
cagctcgttg agtttctcca gaagcgttaa tgtctggctt ctgataaagc gggccatgtt      3960
aagggcggtt ttttcctgtt tggtcactga tgcctccgtg taaggggat ttctgttcat       4020 gggggtaatg ataccgatga acgagagag gatgctcacg atacgggtta ctgatgatga      4080
acatgcccgg ttactggaac gttgtgaggg taaacaactg gcggtatgga tgcggcggga     4140
ccagagaaaa atcactcagg gtcaatgcca gcgcttcgtt aatacagatg taggtgttcc     4200
acagggtagc cagcagcatc ctgcgatgca gatccggaac ataatggtgc agggcgctga     4260
cttccgcgtt tccagacttt acgaaacacg gaaaccgaag accattcatg ttgttgctca     4320
ggtcgcagac gttttgcagc agcagtcgct tcacgttcgc tcgcgtatcg gtgattcatt     4380
ctgctaacca gtaaggcaac cccgccagcc tagccgggtc ctcaacgaca ggagcacgat     4440
catgcgcacc cgtggccagg acccaacgct gcccgagatg cgccgcgtgc ggctgctgga     4500
gatggcggac gcgatggata tgttctgcca agggttggtt tgcgcattca cagttctccg     4560
caagaattga ttggctccaa ttcttggagt ggtgaatccg ttagcgaggt gccgccggct     4620
tccattcagg tcgaggtggc ccggctccat gcaccgcgac gcaacgcggg gaggcagaca     4680
aggtataggg cggcgcctac aatccatgcc aacccgttcc atgtgctcgc cgaggcggca    4740
taaatcgccg tgacgatcag cggtccagtg atcgaagtta ggctggtaag agccgcgagc    4800
gatccttgaa gctgtccctg atggtcgtca tctacctgcc tggacagcat ggcctgcaac    4860
gcgggcatcc cgatgccgcc ggaagcgaga agaatcataa tggggaaggc catccagcct    4920
cgcgtcgcga acgccagcaa gacgtagccc agcg                                 4954
```

<210> SEQ ID NO 26
<211> LENGTH: 4975
<212> TYPE: DNA
<213> ORGANISM: Artificial Sequence
<220> FEATURE:
<223> OTHER INFORMATION: Description of Artificial Sequence: Synthetic
      pET-sdAb Nef5 polynucleotide

<400> SEQUENCE: 26

```
cgtcggccgc catgccggcg ataatggcct gcttctcgcc gaaacgtttg gtggcgggac        60
cagtgacgaa ggcttgagcg agggcgtgca agattccgaa taccgcaagc gacaggccga       120
tcatcgtcgc gctccagcga aagcggtcct cgccgaaaat gacccagagc gctgccggca       180
cctgtcctac gagttgcatg ataaagaaga cagtcataag tgcggcgacg atagtcatgc       240
ccgcgcccca ccggaaggag ctgactgggt tgaaggctct caagggcatc ggtcgacgct       300
ctcccttatg cgactcctgc attaggaagc agcccagtag taggttgagg ccgttgagca       360
ccgccgccgc aaggaatggt gcatgcaagg agatggcgcc caacagtccc ccggccacgg       420
ggcctgccac catacccacg ccgaaacaag cgctcatgag cccgaagtgg cgagcccgat       480
cttccccatc ggtgatgtcg gcgatatagg cgccagcaac cgcacctgtg cgccggtga       540 tgccggccac gatgcgtccg gcgtagagga tcgagatctc gatcccgcga aattaatacg       600
actcactata gggagaccac aacggtttcc ctctagaaat aattttgttt aactttaaga       660
aggagatata ccatggccga ggtgcagctg gtggagtctg ggggaggatc ggtgcaggct       720
ggggaatctc tgaggctcac ctgtatgagc tctggacacg ccttcgctac caatactatg       780
gcgtggttcc gtctggtggc agggaaggaa cgtgaatttg tcgcagctgc gtctcggggt       840
```

```
attgagaccg cgctctatgc agactccgtg aggggccgat tcaccatctc tagagacaac    900
gccaagaaca cggtgtatct gcaaatgaac agcctgaaat ctgaggacac ggccgtttat    960
tactgtgcac aaagcattga caggactggt tactccttgg gtaatattcg gagctattcc   1020
tactggggcc aggggaccca ggtcactgtc tcctcagcgg ccgcacacca ccatcatcat   1080
cacggatcct aagcttgctg agcaataact agcataaccc cttggggcct ctaaacgggt   1140
cttgaggggt tttttgctga aggaggaac tatatccgga tatccacagg acgggtgtgg    1200
tcgccatgat cgcgtagtcg atagtggctc caagtagcga agcgagcagg actgggcggc   1260
ggccaaagcg gtcggacagt gctccgagaa cgggtgcgca tagaaattgc atcaacgcat   1320
atagcgctag cagcacgcca tagtgactgg cgatgctgtc ggaatggacg atatcccgca   1380
agaggcccgg cagtaccggc ataaccaagc ctatgcctac agcatccagg gtgacggtgc   1440
cgaggatgac gatgagcgca ttgttagatt tcatacacgg tgcctgactg cgttagcaat   1500
ttaactgtga taaactaccg cattaaagct tatcgatgat aagctgtcaa acatgagaat   1560
tcttgaagac gaaagggcct cgtgatacgc ctatttttat aggttaatgt catgataata   1620
atggtttctt agacgtcagg tggcacttttt cggggaaatg tgcgcggaac ccctatttgt   1680
ttatttttct aaatacattc aaatatgtat ccgctcatga acaataaacc ctgataaatg   1740
cttcaataat attgaaaaag gaagagtatg agtattcaac atttccgtgt cgcccttatt   1800
cccttttttg cggcattttg ccttcctgtt tttgctcacc cagaaacgct ggtgaaagta   1860
aaagatgctg aagatcagtt gggtgcacga gtgggttaca tcgaactgga tctcaacagc   1920
ggtaagatcc ttgagagttt tcgccccgaa gaacgttttc caatgatgag cacttttaaa   1980
gttctgctat gtggcgcggt attatcccgt gttgacgccg ggcaagagca actcggtcgc   2040
cgcatacact attctcagaa tgacttggtt gagtactcac cagtcacaga aaagcatctt   2100
acggatggca tgacagtaag agaattatgc agtgctgcca taaccatgag tgataacact   2160
gcggccaact tacttctgac aacgatcgga ggaccgaagg agctaaccgc ttttttgcac   2220
aacatggggg atcatgtaac tcgccttgat cgttgggaac cggagctgaa tgaagccata   2280
ccaaacgacg agcgtgacac cacgatgcct gcagcaatgg caacaacgtt gcgcaaacta   2340
ttaactggcg aactacttac tctagcttcc cggcaacaat taatagactg gatggaggcg   2400
gataaagttg caggaccact tctgcgctcg gcccttccgg ctggctggtt tattgctgat   2460
aaatctggag ccggtgagcg tgggtctcgc ggtatcattg cagcactggg gccagatggt   2520
aagccctccc gtatcgtagt tatctacacg acggggagtc aggcaactat ggatgaacga   2580
aatagacaga tcgctgagat aggtgcctca ctgattaagc attggtaact gtcagaccaa   2640
gtttactcat atatacttta gattgattta aaacttcatt tttaatttaa aaggatctag   2700
gtgaagatcc tttttgataa tctcatgacc aaaatccctt aacgtgagtt ttcgttccac   2760
tgagcgtcag accccgtaga aaagatcaaa ggatcttctt gagatccttt ttttctgcgc   2820
gtaatctgct gcttgcaaac aaaaaaacca ccgctaccag cggtggtttg tttgccggat   2880
caagagctac caactctttt tccgaaggta actggcttca gcagagcgca gataccaaat   2940
actgtccttc tagtgtagcc gtagttaggc caccacttca agaactctgt agcaccgcct   3000
acatacctcg ctctgctaat cctgttacca gtggctgctg ccagtggcga taagtcgtgt   3060
cttaccgggt tggactcaag acgatagtta ccggataagg cgcagcggtc gggctgaacg   3120
gggggttcgt gcacacagcc cagcttggag cgaacgacct acaccgaact gagataccta   3180
cagcgtgagc tatgagaaag cgccacgctt cccgaaggga gaaaggcgga caggtatccg   3240
```

```
gtaagcggca gggtcggaac aggagagcgc acgagggagc ttccaggggg aaacgcctgg      3300
tatctttata gtcctgtcgg gtttcgccac ctctgacttg agcgtcgatt tttgtgatgc      3360
tcgtcagggg ggcggagcct atggaaaaac gccagcaacg cggccttttt acggttcctg      3420
gccttttgct ggccttttgc tcacatgttc tttcctgcgt tatcccctga ttctgtggat      3480
aaccgtatta ccgcctttga gtgagctgat accgctcgcc gcagccgaac gaccgagcgc      3540
agcgagtcag tgagcgagga gcggaagag cgcctgatgc ggtattttct ccttacgcat      3600
ctgtgcggta tttcacaccg catatatggt gcactctcag tacaatctgc tctgatgccg      3660
catagttaag ccagtataca ctccgctatc gctacgtgac tgggtcatgg ctgcgccccg      3720
acacccgcca cacccgctg acgcgcctg acgggcttgt ctgctcccgg catccgctta      3780
cagacaagct gtgaccgtct ccgggagctg catgtgtcag aggttttcac cgtcatcacc      3840
gaaacgcgcg aggcagctgc ggtaaagctc atcagcgtgg tcgtgaagcg attcacagat      3900
gtctgcctgt tcatccgcgt ccagctcgtt gagtttctcc agaagcgtta atgtctggct      3960
tctgataaag cgggccatgt taagggcggt ttttcctgt ttggtcactg atgcctccgt      4020
gtaaggggga tttctgttca tgggggtaat gataccgatg aaacgagaga ggatgctcac      4080
gatacgggtt actgatgatg aacatgcccg gttactggaa cgttgtgagg gtaaacaact      4140
ggcggtatgg atgcggcggg accagagaaa aatcactcag ggtcaatgcc agcgcttcgt      4200
taatacagat gtaggtgttc cacagggtag ccagcagcat cctgcgatgc agatccggaa      4260
cataatggtg cagggcgctg acttccgcgt ttccagactt tacgaaacac ggaaaccgaa      4320
gaccattcat gttgttgctc aggtcgcaga cgttttgcag cagcagtcgc ttcacgttcg      4380
ctcgcgtatc ggtgattcat tctgctaacc agtaaggcaa ccccgccagc ctagccgggt      4440
cctcaacgac aggagcacga tcatgcgcac ccgtggccag gacccaacgc tgcccgagat      4500
gcgccgcgtg cggctgctgg agatggcgga cgcgatggat atgttctgcc aagggttggt      4560
ttgcgcattc acagttctcc gcaagaattg attggctcca attcttggag tggtgaatcc      4620
gttagcgagg tgccgccggc ttccattcag gtcgaggtgg cccggctcca tgcaccgcga      4680
cgcaacgcgg ggaggcagac aaggtatagg gcggcgccta caatccatgc caacccgttc      4740
catgtgctcg ccgaggcggc ataaatcgcc gtgacgatca gcggtccagt gatcgaagtt      4800
aggctggtaa gagccgcgag cgatccttga agctgtccct gatggtcgtc atctacctgc      4860
ctggacagca tggcctgcaa cgcgggcatc ccgatgccgc cggaagcgag aagaatcata      4920
atggggaagg ccatccagcc tcgcgtcgcg aacgccagca agacgtagcc cagcg           4975
```

<210> SEQ ID NO 27
<211> LENGTH: 4954
<212> TYPE: DNA
<213> ORGANISM: Artificial Sequence
<220> FEATURE:
<223> OTHER INFORMATION: Description of Artificial Sequence: Synthetic
      pET-sdAb Nef12 polynucleotide

<400> SEQUENCE: 27

```
cgtcggccgc catgccggcg ataatggcct gcttctcgcc gaaacgtttg gtggcgggac        60
cagtgacgaa ggcttgagcg agggcgtgca agattccgaa taccgcaagc gacaggccga       120
tcatcgtcgc gctccagcga aagcggtcct cgccgaaaat gacccagagc gctgccggca       180
cctgtcctac gagttgcatg ataaagaaga cagtcataag tgcggcgacg atagtcatgc       240
cccgcgccca ccggaaggag ctgactgggt tgaaggctct caagggcatc ggtcgacgct       300
```

```
ctcccttatg cgactcctgc attaggaagc agcccagtag taggttgagg ccgttgagca      360
ccgccgccgc aaggaatggt gcatgcaagg agatggcgcc caacagtccc ccggccacgg      420
ggcctgccac catacccacg ccgaaacaag cgctcatgag cccgaagtgg cgagcccgat      480
cttccccatc ggtgatgtcg gcgatatagg cgccagcaac cgcacctgtg cgccggtga      540 tgccggccac gatgcgtccg gcgtagagga tcgagatctc gatcccgcga aattaatacg      600
actcactata gggagaccac aacggtttcc ctctagaaat aattttgttt aactttaaga      660
aggagatata ccatggccga ggtgcagctg gtggagtctg ggggaggctt ggtgcagcct      720 gggggtctc tgagactcac ctgtgcagcc tctggattca ccttcagtag cagtgccatg      780
agctgggtcc gccaggctcc aggaaagggg ctcgagtggg tctcaaatat tagtagtggt      840
ggtggtagca caagctatgc agacttcgtg aagggccgat tcaccatctc cagagacaac      900
gccaagaaca tgctgtatct gcagatggac agtttggaac ctgaggacac ggccgtttat      960
tactgtacgg cctggctttg gggttcggct gagtatgact actggggcca ggggacccag     1020
gtcaccgtct cctcagcggc cgcacaccac catcatcatc acggatccta agcttgctga     1080
gcaataacta gcataacccc ttggggcctc taaacgggtc ttgagggggtt ttttgctgaa     1140 aggaggaact atatccggat atccacagga cgggtgtggt cgccatgatc gcgtagtcga     1200
tagtggctcc aagtagcgaa gcgagcagga ctgggcggcg gccaaagcgg tcggacagtg     1260
ctccgagaac gggtgcgcat agaaattgca tcaacgcata tagcgctagc agcacgccat     1320
agtgactggc gatgctgtcg gaatggacga tatcccgcaa gaggcccggc agtaccggca     1380
taaccaagcc tatgcctaca gcatccaggg tgacggtgcc gaggatgacg atgagcgcat     1440
tgttagattt catacacggt gcctgactgc gttagcaatt taactgtgat aaactaccgc     1500
attaaagctt atcgatgata agctgtcaaa catgagaatt cttgaagacg aaagggcctc     1560
gtgatacgcc tatttttata ggttaatgtc atgataataa tggtttctta gacgtcaggt     1620
ggcacttttc ggggaaatgt gcgcggaacc cctatttgtt tatttttcta aatacattca     1680
aatatgtatc cgctcatgag acaataaccc tgataaatgc ttcaataata ttgaaaaagg     1740
aagagtatga gtattcaaca tttccgtgtc gcccttattc cctttttgc ggcattttgc      1800 cttcctgttt ttgctcaccc agaaacgctg gtgaaagtaa aagatgctga agatcagttg     1860
ggtgcacgag tgggttacat cgaactggat ctcaacagcg gtaagatcct tgagagtttt     1920
cgccccgaag aacgttttcc aatgatgagc acttttaaag ttctgctatg tggcgcggta     1980
ttatcccgtg ttgacgccgg gcaagagcaa ctcggtcgcc gcatacacta ttctcagaat     2040
gacttggttg agtactcacc agtcacagaa aagcatctta cggatggcat gacagtaaga     2100
gaattatgca gtgctgccat aaccatgagt gataacactg cggccaactt acttctgaca     2160
acgatcggag gaccgaagga gctaaccgct tttttgcaca acatggggga tcatgtaact     2220
cgccttgatc gttgggaacc ggagctgaat gaagccatac caaacgacga gcgtgacacc     2280
acgatgcctg cagcaatggc aacaacgttg cgcaaactat taactggcga actacttact     2340
ctagcttccc ggcaacaatt aatagactgg atggaggcgg ataaagttgc aggaccactt     2400
ctgcgctcgg cccttccggc tggctggttt attgctgata aatctggagc cggtgagcgt     2460
gggtctcgcg gtatcattgc agcactgggg ccagatggta agccctcccg tatcgtagtt     2520
atctacacga cggggagtca ggcaactatg gatgaacgaa atagacagat cgctgagata     2580
ggtgcctcac tgattaagca ttggtaactg tcagaccaag tttactcata tatactttag     2640
```

| | |
|---|---|
| attgatttaa aacttcattt ttaatttaaa aggatctagg tgaagatcct ttttgataat | 2700 |
| ctcatgacca aaatcccctta acgtgagttt tcgttccact gagcgtcaga ccccgtagaa | 2760 |
| aagatcaaag gatcttcttg agatcctttt tttctgcgcg taatctgctg cttgcaaaca | 2820 |
| aaaaaaccac cgctaccagc ggtggtttgt ttgccggatc aagagctacc aactcttttt | 2880 |
| ccgaaggtaa ctggcttcag cagagcgcag ataccaaata ctgtccttct agtgtagccg | 2940 |
| tagttaggcc accacttcaa gaactctgta gcaccgccta catacctcgc tctgctaatc | 3000 |
| ctgttaccag tggctgctgc cagtggcgat aagtcgtgtc ttaccgggtt ggactcaaga | 3060 |
| cgatagttac cggataaggc gcagcggtcg ggctgaacgg ggggttcgtg cacacagccc | 3120 |
| agcttggagc gaacgaccta caccgaactg agatacctac agcgtgagct atgagaaagc | 3180 |
| gccacgcttc ccgaagggag aaaggcggac aggtatccgg taagcggcag ggtcggaaca | 3240 |
| ggagagcgca cgagggagct tccaggggga aacgcctggt atctttatag tcctgtcggg | 3300 |
| tttcgccacc tctgacttga gcgtcgattt ttgtgatgct cgtcaggggg gcggagccta | 3360 |
| tggaaaaacg ccagcaacgc ggccttttta cggttcctgg ccttttgctg gccttttgct | 3420 |
| cacatgttct ttcctgcgtt atcccctgat tctgtggata accgtattac cgcctttgag | 3480 |
| tgagctgata ccgctcgccg cagccgaacg accgagcgca gcgagtcagt gagcgaggaa | 3540 |
| gcggaagagc gcctgatgcg gtattttctc cttacgcatc tgtgcggtat ttcacaccgc | 3600 |
| atatatggtg cactctcagt acaatctgct ctgatgccgc atagttaagc cagtatacac | 3660 |
| tccgctatcg ctacgtgact gggtcatggc tgcgccccga cacccgccaa cacccgctga | 3720 |
| cgcgccctga cgggcttgtc tgctcccggc atccgcttac agacaagctg tgaccgtctc | 3780 |
| cgggagctgc atgtgtcaga ggttttcacc gtcatcaccg aaacgcgcga ggcagctgcg | 3840 |
| gtaaagctca tcagcgtggt cgtgaagcga ttcacagatg tctgcctgtt catccgcgtc | 3900 |
| cagctcgttg agtttctcca gaagcgttaa tgtctggctt ctgataaagc gggccatgtt | 3960 |
| aagggcggtt ttttcctgtt tggtcactga tgcctccgtg taaggggat ttctgttcat | 4020 |
| gggggtaatg ataccgatga aacgagagag gatgctcacg atacgggtta ctgatgatga | 4080 |
| acatgcccgg ttactggaac gttgtgaggg taaacaactg gcggtatgga tgcggcggga | 4140 |
| ccagagaaaa atcactcagg gtcaatgcca gcgcttcgtt aatacagatg taggtgttcc | 4200 |
| acagggtagc cagcagcatc ctgcgatgca gatccggaac ataatggtgc agggcgctga | 4260 |
| cttccgcgtt tccagacttt acgaaacacg gaaaccgaag accattcatg ttgttgctca | 4320 |
| ggtcgcagac gttttgcagc agcagtcgct tcacgttcgc tcgcgtatcg gtgattcatt | 4380 |
| ctgctaacca gtaaggcaac cccgccagcc tagccgggtc ctcaacgaca ggagcacgat | 4440 |
| catgcgcacc cgtggccagg acccaacgct gcccgagatg cgccgcgtgc ggctgctgga | 4500 |
| gatggcggac gcgatggata tgttctgcca agggttggtt tgcgcattca cagttctccg | 4560 |
| caagaattga ttggctccaa ttcttggagt ggtgaatccg ttagcgaggt gccgccggct | 4620 |
| tccattcagg tcgaggtggc ccggctccat gcaccgcgac gcaacgcggg gaggcagaca | 4680 |
| aggtataggg cggcgcctac aatccatgcc aacccgttcc atgtgctcgc cgaggcggca | 4740 |
| taaatcgccg tgacgatcag cggtccagtg atcgaagtta ggctggtaag agccgcgagc | 4800 |
| gatccttgaa gctgtccctg atggtcgtca tctacctgcc tggacagcat ggcctgcaac | 4860 |
| gcgggcatcc cgatgccgcc ggaagcgaga agaatcataa tggggaaggc catccagcct | 4920 |
| cgcgtcgcga acgccagcaa gacgtagccc agcg | 4954 |

<210> SEQ ID NO 28
<211> LENGTH: 4945
<212> TYPE: DNA
<213> ORGANISM: Artificial Sequence
<220> FEATURE:
<223> OTHER INFORMATION: Description of Artificial Sequence: Synthetic pET-sdAb Nef19 polynucleotide

<400> SEQUENCE: 28

| | | | | | |
|---|---|---|---|---|---|
| cgtcggccgc | catgccggcg | ataatggcct | gcttctcgcc | gaaacgtttg | gtggcgggac | 60 |
| cagtgacgaa | ggcttgagcg | agggcgtgca | agattccgaa | taccgcaagc | gacaggccga | 120 |
| tcatcgtcgc | gctccagcga | aagcggtcct | cgccgaaaat | gacccagagc | gctgccggca | 180 |
| cctgtcctac | gagttgcatg | ataaagaaga | cagtcataag | tgcggcgacg | atagtcatgc | 240 |
| cccgcgccca | ccggaaggag | ctgactgggt | tgaaggctct | caagggcatc | ggtcgacgct | 300 |
| ctcccttatg | cgactcctgc | attaggaagc | agcccagtag | taggttgagg | ccgttgagca | 360 |
| ccgccgccgc | aaggaatggt | gcatgcaagg | agatggcgcc | caacagtccc | ccggccacgg | 420 |
| ggcctgccac | catacccacg | ccgaaacaag | cgctcatgag | cccgaagtgg | cgagcccgat | 480 |
| cttccccatc | ggtgatgtcg | gcgatatagg | cgccagcaac | cgcacctgtg | cgccggtga | 540 |
| tgccggccac | gatgcgtccg | cgtagagga | tcgagatctc | gatcccgcga | aattaatacg | 600 |
| actcactata | gggagaccac | aacggtttcc | ctctagaaat | aattttgttt | aactttaaga | 660 |
| aggagatata | ccatggccga | ggtgcagctg | gtggagtctg | ggggaggctt | ggtgcaggct | 720 |
| gggggctctc | tgagactctt | ctgtgcggcc | tctggattca | ccttcggtac | cagtaatatg | 780 |
| gcctggctcc | gccaggctcc | agggaagcgt | cgcgagtggg | tcgcacttat | tacgattagt | 840 |
| ggctacacag | actatgcaga | ctccgtgaag | gaccgattca | ccatatccag | agacaacgcc | 900 |
| aagaacacgg | tgtctctgca | aatgaacagc | ctgaaacctg | aggacacggc | catttatttt | 960 |
| tgcgcccggc | gtgtagggtc | tgagtatgat | ttgtggggcc | aggggaccca | ggtcactgtc | 1020 |
| tcctcagcgg | ccgcacacca | ccatcatcat | cacggatcct | aagcttgctg | agcaataact | 1080 |
| agcataaccc | cttggggcct | ctaaacgggt | cttgaggggt | tttttgctga | aggaggaac | 1140 |
| tatatccgga | tatccacagg | acgggtgtgg | tcgccatgat | cgcgtagtcg | atagtggctc | 1200 |
| caagtagcga | agcgagcagg | actgggcggc | ggccaaagcg | gtcggacagt | gctccgagaa | 1260 |
| cgggtgcgca | tagaaattgc | atcaacgcat | atagcgctag | cagcacgcca | tagtgactgg | 1320 |
| cgatgctgtc | ggaatggacg | atatcccgca | agaggcccgg | cagtaccggc | ataaccaagc | 1380 |
| ctatgcctac | agcatccagg | gtgacggtgc | cgaggatgac | gatgagcgca | ttgttagatt | 1440 |
| tcatacacgg | tgcctgactg | cgttagcaat | ttaactgtga | taaactaccg | cattaaagct | 1500 |
| tatcgatgat | aagctgtcaa | acatgagaat | tcttgaagac | gaaagggcct | cgtgatacgc | 1560 |
| ctatttttat | aggttaatgt | catgataata | atggtttctt | agacgtcagg | tggcactttt | 1620 |
| cggggaaatg | tgcgcggaac | ccctatttgt | ttatttttct | aaatacattc | aaatatgtat | 1680 |
| ccgctcatga | gacaataacc | ctgataaatg | cttcaataat | attgaaaaag | gaagagtatg | 1740 |
| agtattcaac | atttccgtgt | cgcccttatt | cccttttttg | cggcattttg | ccttcctgtt | 1800 |
| tttgctcacc | cagaaacgct | ggtgaaagta | aaagatgctg | aagatcagtt | gggtgcacga | 1860 |
| gtgggttaca | tcgaactgga | tctcaacagc | ggtaagatcc | ttgagagttt | tcgccccgaa | 1920 |
| gaacgttttc | caatgatgag | cacttttaaa | gttctgctat | gtggcgcggt | attatcccgt | 1980 |
| gttgacgccg | ggcaagagca | actcggtcgc | cgcatacact | attctcagaa | tgacttggtt | 2040 |
| gagtactcac | cagtcacaga | aaagcatctt | acggatggca | tgacagtaag | agaattatgc | 2100 |

```
agtgctgcca taaccatgag tgataacact gcggccaact tacttctgac aacgatcgga    2160
ggaccgaagg agctaaccgc ttttttgcac aacatggggg atcatgtaac tcgccttgat    2220
cgttgggaac cggagctgaa tgaagccata ccaaacgacg agcgtgacac cacgatgcct    2280
gcagcaatgg caacaacgtt gcgcaaacta ttaactggcg aactacttac tctagcttcc    2340
cggcaacaat taatagactg gatggaggcg gataaagttg caggaccact tctgcgctcg    2400
gcccttccgg ctggctggtt tattgctgat aaatctggag ccgtgagcg tgggtctcgc     2460
ggtatcattg cagcactggg gccagatggt aagccctccc gtatcgtagt tatctacacg    2520
acggggagtc aggcaactat ggatgaacga atagacaga tcgctgagat aggtgcctca     2580
ctgattaagc attggtaact gtcagaccaa gtttactcat atatacttta gattgattta    2640
aaacttcatt tttaatttaa aaggatctag gtgaagatcc ttttttgataa tctcatgacc    2700
aaaatccctt aacgtgagtt ttcgttccac tgagcgtcag accccgtaga aaagatcaaa    2760
ggatcttctt gagatccttt ttttctgcgc gtaatctgct gcttgcaaac aaaaaaacca    2820
ccgctaccag cggtggtttg tttgccggat caagagctac caactctttt tccgaaggta    2880
actggcttca gcagagcgca gataccaaat actgtccttc tagtgtagcc gtagttaggc    2940
caccacttca agaactctgt agcaccgcct acatacctcg ctctgctaat cctgttacca    3000
gtggctgctg ccagtggcga taagtcgtgt cttaccgggt tggactcaag acgatagtta    3060
ccggataagg cgcagcggtc gggctgaacg ggggggttcgt gcacacagcc cagcttggag    3120
cgaacgacct acaccgaact gagataccta cagcgtgagc tatgagaaag cgccacgctt    3180
cccgaaggga gaaaggcgga caggtatccg gtaagcggca gggtcggaac aggagagcgc    3240
acgagggagc ttccaggggg aaacgcctgg tatctttata gtcctgtcgg gtttcgccac    3300
ctctgacttg agcgtcgatt tttgtgatgc tcgtcagggg ggcggagcct atggaaaaac    3360
gccagcaacg cggccttttt acggttcctg gccttttgct ggccttttgc tcacatgttc    3420
tttcctgcgt tatcccctga ttctgtggat aaccgtatta ccgcctttga gtgagctgat    3480
accgctcgcc gcagccgaac gaccgagcgc agcgagtcag tgagcgagga agcggaagag    3540
cgcctgatgc ggtattttct ccttacgcat ctgtgcggta tttcacaccg catatatggt    3600
gcactctcag tacaatctgc tctgatgccg catagttaag ccagtataca ctccgctatc    3660
gctacgtgac tgggtcatgg ctgcgccccg acacccgcca cacccgctg acgcgccctg     3720
acgggcttgt ctgctcccgg catccgctta cagacaagct gtgaccgtct ccgggagctg    3780
catgtgtcag aggttttcac cgtcatcacc gaaacgcgcg aggcagctgc ggtaaagctc    3840
atcagcgtgg tcgtgaagcg attcacagat gtctgcctgt tcatccgcgt ccagctcgtt    3900
gagtttctcc agaagcgtta atgtctggct tctgataaag cgggccatgt taagggcggt    3960
ttttcctgt ttggtcactg atgcctccgt gtaagggga tttctgttca tgggggtaat      4020
gataccgatg aaacgagaga ggatgctcac gatacgggtt actgatgatg aacatgcccg    4080
gttactggaa cgttgtgagg gtaaacaact ggcggtatgg atgcggcggg accagagaaa    4140
aatcactcag ggtcaatgcc agcgcttcgt taatacagat gtaggtgttc cacagggtag    4200
ccagcagcat cctgcgatgc agatccggaa cataatggtg cagggcgctg acttccgcgt    4260
ttccagactt tacgaaacac ggaaaccgaa gaccattcat gttgttgctc aggtcgcaga    4320
cgttttgcag cagcagtcgc ttcacgttcg ctcgcgtatc ggtgattcat tctgctaacc    4380
agtaaggcaa ccccgccagc ctagccgggt cctcaacgac aggagcacga tcatgcgcac    4440
```

```
ccgtggccag acccaacgc tgcccgagat gcgccgcgtg cggctgctgg agatggcgga      4500
cgcgatggat atgttctgcc aagggttggt ttgcgcattc acagttctcc gcaagaattg      4560
attggctcca attcttggag tggtgaatcc gttagcgagg tgccgccggc ttccattcag      4620
gtcgaggtgg cccggctcca tgcaccgcga cgcaacgcgg ggaggcagac aaggtatagg      4680
gcggcgccta caatccatgc caacccgttc catgtgctcg ccgaggcggc ataaatcgcc      4740
gtgacgatca gcggtccagt gatcgaagtt aggctggtaa gagccgcgag cgatccttga      4800
agctgtccct gatggtcgtc atctacctgc ctggacagca tggcctgcaa cgcgggcatc      4860
ccgatgccgc cggaagcgag aagaatcata tggggaagg ccatccagcc tcgcgtcgcg      4920
aacgccagca agacgtagcc cagcg                                            4945

<210> SEQ ID NO 29
<211> LENGTH: 4945
<212> TYPE: DNA
<213> ORGANISM: Artificial Sequence
<220> FEATURE:
<223> OTHER INFORMATION: Description of Artificial Sequence: Synthetic
      pET-sdAb Nef20 polynucleotide

<400> SEQUENCE: 29
cgtcggccgc catgccggcg ataatggcct gcttctcgcc gaaacgtttg gtggcgggac        60
cagtgacgaa ggcttgagcg agggcgtgca agattccgaa taccgcaagc gacaggccga       120
tcatcgtcgc gctccagcga aagcggtcct cgccgaaaat gacccagagc gctgccggca       180
cctgtcctac gagttgcatg ataaagaaga cagtcataag tgcggcgacg atagtcatgc       240
cccgcgccca ccggaaggag ctgactgggt tgaaggctct caagggcatc ggtcgacgct       300
ctcccttatg cgactcctgc attaggaagc agcccagtag taggttgagg ccgttgagca       360
ccgccgccgc aaggaatggt gcatgcaagg agatggcgcc caacagtccc ccggccacgg       420
ggcctgccac catacccacg ccgaaacaag cgctcatgag cccgaagtgg cgagcccgat       480
cttccccatc ggtgatgtcg gcgatatagg cgccagcaac cgcacctgtg cgccggtga        540 tgccggccac gatgcgtccg gcgtagagga tcgagatctc gatcccgcga aattaatacg       600
actcactata gggagaccac aacggtttcc ctctagaaat aattttgttt aactttaaga       660
aggagatata ccatggccga ggtgcagctg gtggagtctg ggggaggctt ggtgcaggct       720
gggggctctc tgagactctt ctgtgcggcc tctggattca ccttcggtac cagtaatatg       780
gcctggctcc gccaggctcc agggaagcgt cgcgagtggg tcgcacttat tacgattagt       840
ggctacacag actatgcaga ctccgtgaag gaccgattca ccatatccag agacaacgcc       900
aagaacacgg tgtctctgca aatgaacagc ctgaaacctg aggacacggc catttatttt       960
tgcgcccggc gtgtagggtc tgagtatgat ttgtggggcc aggggaccca ggtcactgtc      1020
tcctcagcgg ccgcacacca ccatcatcat cacggatcct aagcttgctg agcaataact      1080
agcataaccc cttggggcct ctaaacgggt cttgaggggt tttttgctga aggaggaac       1140 tatatccgga tatccacagg acgggtgtgg tcgccatgat cgcgtagtcg atagtggctc      1200
caagtagcga agcgagcagg actgggcggc ggccaaagcg gtcggacagt gctccgagaa      1260
cgggtgcgca tagaaattgc atcaacgcat atagcgctag cagcacgcca tagtgactgg      1320
cgatgctgtc ggaatggacg atatcccgca agaggcccgg cagtaccggc ataaccaagc      1380
ctatgcctac agcatccagg gtgacggtgc cgaggatgac gatgagcgca ttgttagatt      1440
tcatacacgg tgcctgactg cgttagcaat ttaactgtga taaactaccg cattaaagct      1500
```

```
tatcgatgat aagctgtcaa acatgagaat tcttgaagac gaaagggcct cgtgatacgc    1560
ctatttttat aggttaatgt catgataata atggtttctt agacgtcagg tggcactttt    1620
cggggaaatg tgcgcggaac ccctatttgt ttattttttct aaatacattc aaatatgtat   1680
ccgctcatga gacaataacc ctgataaatg cttcaataat attgaaaaag gaagagtatg    1740
agtattcaac atttccgtgt cgcccttatt ccctttttg cggcattttg ccttcctgtt     1800
tttgctcacc cagaaacgct ggtgaaagta aaagatgctg aagatcagtt gggtgcacga    1860
gtgggttaca tcgaactgga tctcaacagc ggtaagatcc ttgagagttt tcgccccgaa    1920
gaacgttttc caatgatgag cacttttaaa gttctgctat gtggcgcggt attatcccgt    1980
gttgacgccg ggcaagagca actcggtcgc cgcatacact attctcagaa tgacttggtt    2040
gagtactcac cagtcacaga aaagcatctt acggatggca tgacagtaag agaattatgc    2100
agtgctgcca taaccatgag tgataacact gcggccaact tacttctgac aacgatcgga    2160
ggaccgaagg agctaaccgc ttttttgcac aacatggggg atcatgtaac tcgccttgat    2220
cgttgggaac cggagctgaa tgaagccata ccaaacgacg agcgtgacac cacgatgcct    2280
gcagcaatgg caacaacgtt gcgcaaacta ttaactggcg aactacttac tctagcttcc    2340
cggcaacaat taatagactg gatggaggcg gataaagttg caggaccact tctgcgctcg    2400
gcccttccgg ctggctggtt tattgctgat aaatctggag ccggtgagcg tgggtctcgc    2460
ggtatcattg cagcactggg gccagatggt aagccctccc gtatcgtagt tatctacacg    2520
acggggagtc aggcaactat ggatgaacga atagacaga tcgctgagat aggtgcctca     2580
ctgattaagc attggtaact gtcagaccaa gtttactcat atatacttta gattgattta    2640
aaacttcatt tttaatttaa aaggatctag gtgaagatcc ttttttgataa tctcatgacc   2700
aaaatccctt aacgtgagtt ttcgttccac tgagcgtcag accccgtaga aaagatcaaa    2760
ggatcttctt gagatccttt ttttctgcgc gtaatctgct gcttgcaaac aaaaaaacca    2820
ccgctaccag cggtggtttg tttgccggat caagagctac caactctttt tccgaaggta    2880
actggcttca gcagagcgca gataccaaat actgtccttc tagtgtagcc gtagttaggc    2940
caccacttca agaactctgt agcaccgcct acatacctcg ctctgctaat cctgttacca    3000
gtggctgctg ccagtggcga taagtcgtgt cttaccgggt tggactcaag acgatagtta    3060
ccggataagg cgcagcggtc gggctgaacg ggggggttcgt gcacacagcc cagcttggag    3120
cgaacgacct acaccgaact gagataccta cagcgtgagc tatgagaaag cgccacgctt    3180
cccgaaggga gaaaggcgga caggtatccg gtaagcggca gggtcggaac aggagagcgc    3240
acgagggagc ttccaggggg aaacgcctgg tatctttata gtcctgtcgg gtttcgccac    3300
ctctgacttg agcgtcgatt tttgtgatgc tcgtcagggg gcggagcct atggaaaaac     3360
gccagcaacg cggccttttt acggttcctg gccttttgct ggccttttgc tcacatgttc    3420
tttcctgcgt tatcccctga ttctgtggat aaccgtatta ccgcctttga gtgagctgat    3480
accgctcgcc gcagccgaac gaccgagcgc agcgagtcag tgagcgagga agcggaagag    3540
cgcctgatgc ggtattttct ccttacgcat ctgtgcggta tttcacaccg catatatggt    3600
gcactctcag tacaatctgc tctgatgccg catagttaag ccagtataca ctccgctatc    3660
gctacgtgac tgggtcatgg ctgcgccccg acacccgcca cacccgctg acgcgccctg      3720
acgggcttgt ctgctcccgg catccgctta cagacaagct gtgaccgtct ccgggagctg    3780
catgtgtcag aggttttcac cgtcatcacc gaaacgcgcg aggcagctgc ggtaaagctc    3840
atcagcgtgg tcgtgaagcg attcacagat gtctgcctgt tcatccgcgt ccagctcgtt    3900
```

```
gagtttctcc agaagcgtta atgtctggct tctgataaag cgggccatgt taagggcggt    3960 ttttcctgt ttggtcactg atgcctccgt gtaagggga tttctgttca tgggggtaat    4020
gataccgatg aaacgagaga ggatgctcac gatacgggtt actgatgatg aacatgcccg    4080
gttactggaa cgttgtgagg gtaaacaact ggcggtatgg atgcggcggg accagagaaa    4140
aatcactcag ggtcaatgcc agcgcttcgt taatacagat gtaggtgttc cacagggtag    4200
ccagcagcat cctgcgatgc agatccggaa cataatggtg cagggcgctg acttccgcgt    4260
ttccagactt tacgaaacac ggaaaccgaa gaccattcat gttgttgctc aggtcgcaga    4320
cgttttgcag cagcagtcgc ttcacgttcg ctcgcgtatc ggtgattcat tctgctaacc    4380
agtaaggcaa ccccgccagc ctagccgggt cctcaacgac aggagcacga tcatgcgcac    4440
ccgtggccag gacccaacgc tgcccgagat gcgccgcgtg cggctgctgg agatggcgga    4500
cgcgatggat atgttctgcc aagggttggt ttgcgcattc acagttctcc gcaagaattg    4560
attggctcca attcttggag tggtgaatcc gttagcgagg tgccgccggc ttccattcag    4620
gtcgaggtgg cccggctcca tgcaccgcga cgcaacgcgg ggaggcagac aaggtatagg    4680
gcggcgccta caatccatgc caacccgttc catgtgctcg ccgaggcggc ataaatcgcc    4740
gtgacgatca gcggtccagt gatcgaagtt aggctggtaa gagccgcgag cgatccttga    4800
agctgtccct gatggtcgtc atctacctgc ctggacagca tggcctgcaa cgcgggcatc    4860
ccgatgccgc cggaagcgag aagaatcata atggggaagg ccatccagcc tcgcgtcgcg    4920
aacgccagca agacgtagcc cagcg                                          4945
```

<210> SEQ ID NO 30
<211> LENGTH: 5837
<212> TYPE: DNA
<213> ORGANISM: Artificial Sequence
<220> FEATURE:
<223> OTHER INFORMATION: Description of Artificial Sequence: Synthetic
      pcDNA-sdAb Nef19 polynucleotide

<400> SEQUENCE: 30

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattccac    960
```

-continued

```
catggccgag gtgcagctgg tggagtctgg gggaggcttg gtgcaggctg ggggctctct      1020
gagactcttc tgtgcggcct ctggattcac cttcggtacc agtaatatgg cctggctccg      1080
ccaggctcca gggaagcgtc gcgagtgggt cgcacttatt acgattagtg gctacacaga      1140
ctatgcagac tccgtgaagg accgattcac catatccaga gacaacgcca agaacacggt      1200
gtctctgcaa atgaacagcc tgaaacctga ggacacggcc atttattttt gcgcccggcg      1260
tgtagggtct gagtatgatt tgtggggcca ggggacccag gtcactgtct cctcagcggc      1320
cgcagaacaa aaactcatct cagaagagga tctgaatggg gccgcacatc accaccatca      1380
ccatgggagc tagctcgagt ctagagggcc cgtttaaacc cgctgatcag cctcgactgt      1440
gccttctagt tgccagccat ctgttgtttg cccctccccc gtgccttcct tgaccctgga      1500
aggtgccact cccactgtcc tttcctaata aaatgaggaa attgcatcgc attgtctgag      1560
taggtgtcat tctattctgg ggggtgggt ggggcaggac agcaaggggg aggattggga      1620
agacaatagc aggcatgctg gggatgcggt gggctctatg gcttctgagg cggaaagaac      1680
cagctggggc tctagggggt atccccacgc gccctgtagc ggcgcattaa gcgcggcggg      1740
tgtggtggtt acgcgcagcg tgaccgctac acttgccagc gccctagcgc ccgctccttt      1800
cgctttcttc ccttcctttc tcgccacgtt cgccggcttt ccccgtcaag ctctaaatcg      1860
ggggctccct ttagggttcc gatttagtgc tttacggcac ctcgacccca aaaaacttga      1920
ttagggtgat ggttcacgta gtgggccatc gccctgatag acggttttc gccctttgac       1980 gttggagtcc acgttcttta atagtggact cttgttccaa actggaacaa cactcaaccc      2040
tatctcggtc tattcttttg atttataagg gattttgccg atttcggcct attggttaaa      2100
aaatgagctg atttaacaaa aatttaacgc gaattaattc tgtggaatgt gtgtcagtta      2160
gggtgtggaa agtccccagg ctccccagca ggcagaagta tgcaaagcat gcatctcaat      2220
tagtcagcaa ccaggtgtgg aaagtcccca ggctccccag caggcagaag tatgcaaagc      2280
atgcatctca attagtcagc aaccatagtc ccgcccctaa ctccgcccat cccgccccta      2340
actccgccca gttccgccca ttctccgccc catggctgac taatttttttt tatttatgca      2400 gaggccgagg ccgcctctgc ctctgagcta ttccagaagt agtgaggagg cttttttgga      2460
ggcctaggct tttgcaaaaa gctcccggga gcttgtatat ccattttcgg atctgatcaa      2520
gagacaggat gaggatcgtt tcgcatgatt gaacaagatg gattgcacgc aggttctccg      2580
gccgcttggg tggagaggct attcggctat gactgggcac aacagacaat cggctgctct      2640
gatgccgccg tgttccggct gtcagcgcag gggcgcccgg ttcttttgt caagaccgac      2700 ctgtccggtg ccctgaatga actgcaggac gaggcagcgc ggctatcgtg ctggccacg       2760 acgggcgttc cttgcgcagc tgtgctcgac gttgtcactg aagcgggaag ggactggctg      2820
ctattgggcg aagtgccggg gcaggatctc ctgtcatctc accttgctcc tgccgagaaa      2880
gtatccatca tggctgatgc aatgcggcgg ctgcatacgc ttgatccggc tacctgccca      2940
ttcgaccacc aagcgaaaca tcgcatcgag cgagcacgta ctcggatgga agccggtctt      3000
gtcgatcagg atgatctgga cgaagagcat caggggctcg cgccagccga actgttcgcc      3060
aggctcaagg cgcgcatgcc cgacggcgag gatctcgtcg tgacccatgg cgatgcctgc      3120
ttgccgaata tcatggtgga aaatggccgc ttttctggat tcatcgactg tggccggctg      3180
ggtgtggcgg accgctatca ggacatagcg ttggctaccc gtgatattgc tgaagagctt      3240
ggcggcgaat gggctgaccg cttcctcgtg ctttacggta tcgccgctcc cgattcgcag      3300
```

```
cgcatcgcct tctatcgcct tcttgacgag ttcttctgag cgggactctg ggttcgaaa      3360 tgaccgacca agcgacgccc aacctgccat cacgagattt cgattccacc gccgccttct      3420
atgaaaggtt gggcttcgga atcgttttcc gggacgccgg ctggatgatc ctccagcgcg      3480
gggatctcat gctggagttc ttcgcccacc ccaacttgtt tattgcagct tataatggtt      3540
acaaataaag caatagcatc acaaatttca caaataaagc attttttca ctgcattcta       3600 gttgtggttt gtccaaactc atcaatgtat cttatcatgt ctgtataccg tcgacctcta      3660
gctagagctt ggcgtaatca tggtcatagc tgtttcctgt gtgaaattgt tatccgctca      3720
caattccaca acatacga gccggaagca taaagtgtaa agcctggggt gcctaatgag        3780
tgagctaact cacattaatt gcgttgcgct cactgcccgc tttccagtcg ggaaacctgt      3840
cgtgccagct gcattaatga atcggccaac gcgcggggag aggcggtttg cgtattgggc      3900
gctcttccgc ttcctcgctc actgactcgc tgcgctcggt cgttcggctg cggcgagcgg      3960
tatcagctca ctcaaaggcg gtaatacggt tatccacaga atcaggggat aacgcaggaa      4020
agaacatgtg agcaaaaggc cagcaaaagg ccaggaaccg taaaaaggcc gcgttgctgg      4080
cgttttccca taggctccgc cccctgacg agcatcacaa aaatcgacgc tcaagtcaga       4140
ggtggcgaaa cccgacagga ctataaagat accaggcgtt tccccctgga agctccctcg      4200
tgcgctctcc tgttccgacc ctgccgctta ccggatacct gtccgccttt ctcccttcgg      4260
gaagcgtggc gctttctcat agctcacgct gtaggtatct cagttcggtg taggtcgttc      4320
gctccaagct gggctgtgtg cacgaacccc ccgttcagcc cgaccgctgc gccttatccg      4380
gtaactatcg tcttgagtcc aacccggtaa gacacgactt atcgccactg gcagcagcca      4440
ctggtaacag gattagcaga gcgaggtatg taggcggtgc tacagagttc ttgaagtggt      4500
ggcctaacta cggctacact agaagaacag tatttggtat ctgcgctctg ctgaagccag      4560
ttaccttcgg aaaaagagtt ggtagctctt gatccggcaa acaaaccacc gctggtagcg      4620
gtttttttgt ttgcaagcag cagattacgc gcagaaaaaa aggatctcaa gaagatcctt      4680
tgatcttttc tacggggtct gacgctcagt ggaacgaaaa ctcacgttaa gggattttgg      4740
tcatgagatt atcaaaaagg atcttcacct agatcctttt aaattaaaaa tgaagtttta      4800
aatcaatcta agtatatat gagtaaactt ggtctgacag ttaccaatgc ttaatcagtg      4860
aggcacctat ctcagcgatc tgtctatttc gttcatccat agttgcctga ctccccgtcg      4920
tgtagataac tacgatacgg gagggcttac catctggccc cagtgctgca atgataccgc      4980
gagacccacg ctcaccggct ccagatttat cagcaataaa ccagccagcc ggaagggccg      5040
agcgcagaag tggtcctgca actttatccg cctccatcca gtctattaat tgttgccggg      5100
aagctagagt aagtagttcg ccagttaata gtttgcgcaa cgttgttgcc attgctacag      5160
gcatcgtggt gtcacgctcg tcgtttggta tggcttcatt cagctccggt tcccaacgat      5220
caaggcgagt tacatgatcc cccatgttgt gcaaaaaagc ggttagctcc ttcggtcctc      5280
cgatcgttgt cagaagtaag ttggccgcag tgttatcact catggttatg gcagcactgc      5340
ataattctct tactgtcatg ccatccgtaa gatgcttttc tgtgactggt gagtactcaa      5400
ccaagtcatt ctgagaatag tgtatgcggc gaccgagttg ctcttgcccg gcgtcaatac      5460
gggataatac cgcgccacat agcagaactt taaaagtgct catcattgga aaacgttctt      5520
cggggcgaaa actctcaagg atcttaccgc tgttgagatc cagttcgatg taacccactc      5580
gtgcacccaa ctgatcttca gcatctttta ctttcaccag cgtttctggg tgagcaaaaa      5640
caggaaggca aaatgccgca aaaaagggaa taagggcgac acggaaatgt tgaatactca      5700
```

```
tactcttcct ttttcaatat tattgaagca tttatcaggg ttattgtctc atgagcggat    5760
acatatttga atgtatttag aaaaataaac aaatagggt tccgcgcaca tttccccgaa    5820
aagtgccacc tgacgtc                                                  5837
```

<210> SEQ ID NO 31
<211> LENGTH: 157
<212> TYPE: PRT
<213> ORGANISM: Artificial Sequence
<220> FEATURE:
<223> OTHER INFORMATION: Description of Artificial Sequence: Synthetic
      Nef 13 polypeptide

<400> SEQUENCE: 31

```
Met Gly His His His His His Gly Ser Glu Ala Gln Glu Glu Glu
1               5                   10                  15

Glu Val Gly Phe Pro Val Thr Pro Gln Val Pro Leu Arg Pro Met Thr
            20                  25                  30

Tyr Lys Ala Ala Val Asp Leu Ser His Phe Leu Lys Glu Lys Gly Gly
        35                  40                  45

Leu Glu Gly Leu Ile His Ser Gln Arg Arg Gln Asp Ile Leu Asp Leu
    50                  55                  60

Trp Ile Tyr His Thr Gln Gly Tyr Phe Pro Asp Trp Gln Asn Tyr Thr
65                  70                  75                  80

Pro Gly Pro Gly Val Arg Tyr Pro Leu Thr Phe Gly Trp Cys Tyr Lys
                85                  90                  95

Leu Val Pro Val Glu Pro Asp Lys Val Glu Glu Ala Asn Lys Gly Glu
            100                 105                 110

Asn Thr Ser Leu Leu His Pro Val Ser Leu His Gly Met Asp Asp Pro
        115                 120                 125

Glu Arg Glu Val Leu Glu Trp Arg Phe Asp Ser Arg Leu Ala Phe His
    130                 135                 140

His Val Ala Arg Glu Leu His Pro Glu Tyr Phe Lys Asn
145                 150                 155
```

<210> SEQ ID NO 32
<211> LENGTH: 160
<212> TYPE: PRT
<213> ORGANISM: Artificial Sequence
<220> FEATURE:
<223> OTHER INFORMATION: Description of Artificial Sequence: Synthetic
      Nef W12 polypeptide

<400> SEQUENCE: 32

```
Met Gly His His His His His Gly Ser Ala Trp Leu Glu Ala Gln
1               5                   10                  15

Glu Glu Glu Glu Val Gly Phe Pro Val Thr Pro Gln Val Pro Leu Arg
            20                  25                  30

Pro Met Thr Tyr Lys Ala Ala Val Asp Leu Ser His Phe Leu Lys Glu
        35                  40                  45

Lys Gly Gly Leu Glu Gly Leu Ile His Ser Gln Arg Arg Gln Asp Ile
    50                  55                  60

Leu Asp Leu Trp Ile Tyr His Thr Gln Gly Tyr Phe Pro Asp Trp Gln
65                  70                  75                  80

Asn Tyr Thr Pro Gly Pro Gly Val Arg Tyr Pro Leu Thr Phe Gly Trp
                85                  90                  95

Cys Tyr Lys Leu Val Pro Val Glu Pro Asp Lys Val Glu Glu Ala Asn
            100                 105                 110
```

Lys Gly Glu Asn Thr Ser Leu Leu His Pro Val Ser Leu His Gly Met
        115                 120                 125

Asp Asp Pro Glu Arg Glu Val Leu Glu Trp Arg Phe Asp Ser Arg Leu
    130                 135                 140

Ala Phe His His Val Ala Arg Glu Leu His Pro Glu Tyr Phe Lys Asn
145                 150                 155                 160

<210> SEQ ID NO 33
<211> LENGTH: 162
<212> TYPE: PRT
<213> ORGANISM: Artificial Sequence
<220> FEATURE:
<223> OTHER INFORMATION: Description of Artificial Sequence: Synthetic
      Nef W10 polypeptide

<400> SEQUENCE: 33

Met Gly Trp Leu Glu Ala Gln Glu Glu Glu Val Gly Phe Pro Val
1               5                   10                  15

Thr Pro Gln Val Pro Leu Arg Pro Met Thr Tyr Lys Ala Ala Val Asp
            20                  25                  30

Leu Ser His Phe Leu Lys Glu Lys Gly Gly Leu Glu Gly Leu Ile His
        35                  40                  45

Ser Gln Arg Arg Gln Asp Ile Leu Asp Leu Trp Ile Tyr His Thr Gln
    50                  55                  60

Gly Tyr Phe Pro Asp Trp Gln Asn Tyr Thr Pro Gly Pro Gly Val Arg
65                  70                  75                  80

Tyr Pro Leu Thr Phe Gly Trp Cys Tyr Lys Leu Val Pro Val Glu Pro
                85                  90                  95

Asp Lys Val Glu Glu Ala Asn Lys Gly Glu Asn Thr Ser Leu Leu His
            100                 105                 110

Pro Val Ser Leu His Gly Met Asp Asp Pro Glu Arg Glu Val Leu Glu
        115                 120                 125

Trp Arg Phe Asp Ser Arg Leu Ala Phe His His Val Ala Arg Glu Leu
    130                 135                 140

His Pro Glu Tyr Phe Lys Asn Ala Ala Ala His His His His His
145                 150                 155                 160

Gly Ser

<210> SEQ ID NO 34
<211> LENGTH: 71
<212> TYPE: DNA
<213> ORGANISM: Artificial Sequence
<220> FEATURE:
<223> OTHER INFORMATION: Description of Artificial Sequence: Synthetic
      5' Nef-Nco1-pET oligonucleotide
<220> FEATURE:
<221> NAME/KEY: modified_base
<222> LOCATION: (47)..(47)
<223> OTHER INFORMATION: a, c, g, t or u
<220> FEATURE:
<221> NAME/KEY: modified_base
<222> LOCATION: (50)..(50)
<223> OTHER INFORMATION: a, c, g, t or u

<400> SEQUENCE: 34
ctttaagaag gagatatacc atgggccayc aycaycayca ycayggntcn gaagcacaag    60
aggaggagga g                                                        71

<210> SEQ ID NO 35
<211> LENGTH: 46

<212> TYPE: DNA
<213> ORGANISM: Artificial Sequence
<220> FEATURE:
<223> OTHER INFORMATION: Description of Artificial Sequence: Synthetic
      3' Nef-Blp1-pET oligonucleotide

<400> SEQUENCE: 35
ggggttatgc tagttattgc tcagcgttct tgaagtactc cggatg         46

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      5'Nef.Nco1.W oligonucleotide

<400> SEQUENCE: 36
ctttaagaag gagatatacc atgggccacc accatcatca tcacggatcc gcctggctag    60
aagcacaaga ggaggaggag                                                80

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence: Synthetic
      3' Nef-Blp1-pET oligonucleotide

<400> SEQUENCE: 37
ggggttatgc tagttattgc tcagcgttct tgaagtactc cggatg         46

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence: Synthetic
      5'Nef/pET oligonucleotide
<220> FEATURE:
<221> NAME/KEY: modified_base
<222> LOCATION: (30)..(30)
<223> OTHER INFORMATION: a, c, g, t or u
<220> FEATURE:
<221> NAME/KEY: modified_base
<222> LOCATION: (36)..(36)
<223> OTHER INFORMATION: a, c, g, t or u

<400> SEQUENCE: 38
ttaagaagga gatataccat gggctggctn gargcncarg argaggagga ggtgggt    57

<210> SEQ ID NO 39
<211> LENGTH: 84
<212> TYPE: DNA
<213> ORGANISM: Artificial Sequence
<220> FEATURE:
<223> OTHER INFORMATION: Description of Artificial Sequence: Synthetic
      3'Nef/pJF-pET oligonucleotide

<400> SEQUENCE: 39
ggggttatgc tagttagctc agcaagctta ggatccgtga tgatgatggt ggtgtgcggc    60
cgcgttcttg aagtactccg gatg                                           84

<210> SEQ ID NO 40
<211> LENGTH: 18
<212> TYPE: DNA
<213> ORGANISM: Artificial Sequence

```
<220> FEATURE:
<223> OTHER INFORMATION: Description of Artificial Sequence: Synthetic
      5' Int.Nef oligonucleotide

<400> SEQUENCE: 40
cacacaaggc tacttccc                                                   18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      3' Int.Nef oligonucleotide

<400> SEQUENCE: 41
caactggtac tagcttgtag                                                 20

<210> SEQ ID NO 42
<211> LENGTH: 53
<212> TYPE: DNA
<213> ORGANISM: Artificial Sequence
<220> FEATURE:
<223> OTHER INFORMATION: Description of Artificial Sequence: Synthetic
      Sup-6HisGS/P3 oligonucleotide

<400> SEQUENCE: 42
catcaccacc atcaccatgg gagctagact gttgaaagtt gtttagcaaa acc            53

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      Inf-6HisGS/cmyc oligonucleotide

<400> SEQUENCE: 43
gctcccatgg tgatggtggt gatgtgcggc cccattcaga tcctc                     45

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      Amont-Hind3 oligonucleotide

<400> SEQUENCE: 44
aacagctatg accatg                                                     16

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      Aval-Bsm1 oligonucleotide

<400> SEQUENCE: 45
gcaagcccaa taggaaccc                                                  19

<210> SEQ ID NO 46
<211> LENGTH: 57
<212> TYPE: DNA
<213> ORGANISM: Artificial Sequence
<220> FEATURE:
```

<223> OTHER INFORMATION: Description of Artificial Sequence: Synthetic
      5' PhoA/pHen oligonucleotide

<400> SEQUENCE: 46
ggattgttat tactcgcggc ccagccggcc atggcagccg atcctcgaga gctcccg        57

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      3' PhoA/pHen oligonucleotide

<400> SEQUENCE: 47
gagatgagtt tttgttctgc ggccgctttc agccccagag cggctttc        48

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      3' CH2FORTA4 oligonucleotide

<400> SEQUENCE: 48
cgccatcaag gtaccagttg a        21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      3'CH2-2 oligonucleotide

<400> SEQUENCE: 49
ggtacgtgct gttgaactgt tcc        23

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      3' RC-IgG2 oligonucleotide

<400> SEQUENCE: 50
ggagctgggg tcttcgctgt ggtgcg        26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      3' RC-IgG3 oligonucleotide

<400> SEQUENCE: 51
tggttgtggt tttggtgtct tgggtt        26

<210> SEQ ID NO 52
<211> LENGTH: 57
<212> TYPE: DNA
<213> ORGANISM: Artificial Sequence

```
<220> FEATURE:
<223> OTHER INFORMATION: Description of Artificial Sequence: Synthetic
      5'VH1-Sfi oligonucleotide

<400> SEQUENCE: 52
catgccatga ctcgcggccc agccggccat ggcccaggtg cagctggtgc agtctgg      57

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence: Synthetic
      5'VH2-Sfi oligonucleotide

<400> SEQUENCE: 53
catgccatga ctcgcggccc agccggccat ggcccaggtc accttgaagg agtctgg      57

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence: Synthetic
      5'VH3-Sfi oligonucleotide

<400> SEQUENCE: 54
catgccatga ctcgcggccc agccggccat ggccgaggtg cagctggtgg agtctgg      57

<210> SEQ ID NO 55
<211> LENGTH: 57
<212> TYPE: DNA
<213> ORGANISM: Artificial Sequence
<220> FEATURE:
<223> OTHER INFORMATION: Description of Artificial Sequence: Synthetic
      5'VH4-Sfi oligonucleotide

<400> SEQUENCE: 55
catgccatga ctcgcggccc agccggccat ggcccaggtg cagctgcagg agtcggg      57

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      3'VHH-Not oligonucleotide

<400> SEQUENCE: 56
cacgattctg cggccgctga ggagacaggt gacctgggtc c                       41

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      ANefEcoK5p oligonucleotide

<400> SEQUENCE: 57
gaattccacc atggccgagg tgcagctggt g                                  31

<210> SEQ ID NO 58
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      ANefXho3p oligonucleotide

<400> SEQUENCE: 58
ctcgagctag ctcccatggt gatggtg                                            27
```

SINGLE-DOMAIN ANTIBODIES THAT BIND TO HIV-1 NEF WITH HIGH AFFINITY

This application is the U.S. national phase of International Application No. PCT/IB2008/054832, filed 18 Nov. 2008, which designated the U.S. and claims the benefit of FR Application No. 07/08189, filed 22 Nov. 2007, the entire contents of each of which are hereby incorporated by reference.

The invention relates to single-domain antibody (sdAb) fragments capable of inhibiting the HIV Nef protein and to the immunological applications thereof, more particularly in immunotherapy for AIDS treatment.

BACKGROUND OF THE INVENTION

The recognition specificity of antibodies for hitting a given target has been exploited for the diagnosis and therapy of various pathological conditions, and most particularly in the case of acquired immunodeficiency syndrome (AIDS), where the target can be a protein of human immunodeficiency viruses type 1 or 2 (HIV-1 and HIV-2).

In the context of the search for candidate antibodies for neutralizing an HIV protein, the inventors have oriented their studies toward particular antibodies, devoid of a light chain, identified in camelids (camel, dromedary, llama) (Hamers-Casterman et al., 1993).

Camelid single heavy-chain antibody variable domains (VHH), which specifically recognize one type of antigen, have been selected from an immunized animal and have been produced from plasmid constructs. As shown in the examples, these antibody fragments have been found to be capable of specifically targeting regions of the HIV Nef (negative regulatory factor) protein that are involved in the development of acquired immunodeficiency syndrome (AIDS).

The aim of the invention is therefore to provide single heavy-chain antibody fragments (also called sdAbs for single-domain antibodies), having the desired target and epitope recognition properties.

The aim of the invention is also to provide a method for producing these antibody fragments. According to yet another aspect, the invention is directed toward the immunotherapeutic applications thereof.

SUMMARY OF THE INVENTION

The sdAb fragments of the invention are characterized in that they are anti-HIV Nef protein fragments corresponding to all or part of the VHH domains of camelids, in particular llamas.

According to an aspect of general interest, these fragments exhibit great stability and can be obtained in large amounts in soluble forms in bacteria, yeasts or any other system of production from prokaryotic or eukaryotic cells.

Their high stability enables them to acquire and maintain correct folding and therefore to remain soluble even under conditions which do not allow the formation of disulfide bridges, such as the cytoplasm of bacteria or of eukaryotic cells.

The invention is in particular directed toward the anti-Nef antibody fragments having an amino acid sequence as encoded by a nucleotide sequence chosen from the group comprising the sequences SEQ ID Nos. 1 to 6.

The invention is thus more especially directed toward the anti-Nef antibody fragments having an amino acid sequence chosen from the group comprising the sequences SEQ ID Nos. 7 to 12.

The invention is also directed toward CDRs of these sdAb fragments.

The nucleic acids capable of encoding said fragments also come within the field of the invention. The invention is in particular directed toward, as novel products, the nucleic acids corresponding to the sequences SEQ ID Nos. 1 to 6.

The invention is also directed toward a method for producing the anti-Nef antibody fragments defined above.

This method is characterized in that it comprises:
  immunization of camelids, in particular of llamas, with the Nef protein as immunogen,
  purification of the B lymphocytes recovered from the blood,
  construction of a VHH library, and
  isolation of the sdAb fragments from the library and purification of said fragments.

More especially, the Nef protein used for the immunization lacks its first 56 amino acids.

The construction of the library advantageously comprises:
  extraction of the total RNA from the B lymphocytes,
  reverse transcription of the RNAs so as to obtain the corresponding cDNAs,
  PCR amplification of the genes encoding the variable regions of the anti-Nef single heavy-chain antibodies,
  ligation of VHH DNA fragments, obtained by enzyme cleavage of the amplified DNAs with a phagemid.

Preferably, the sdAbs are isolated from the libraries by means of the phage display technique and are purified.

The various sdAbs obtained have been validated in terms of specificity and affinity, as illustrated by the examples.

In accordance with the invention, the selected sdAb genes have subsequently been inserted into expression vectors, in particular plasmids, so as to produce various anti-Nef sdAbs capable of binding to Nef in HIV-infected cells.

These expression vectors also constitute novel products, and the invention is therefore also directed toward said expression vectors.

The invention is more especially directed toward expression vectors, in particular plasmids, containing between two unique restriction enzyme sites, the promoters, the signal sequences and the nucleotide sequences capable of encoding the sdAb fragments defined above, or the CDRs regions of the sdAbs.

These vectors, in particular these plasmids, are capable of expressing the fragments of the invention in large amounts, in soluble forms, for example in bacteria.

The invention is thus directed towards the plasmids pET14bNef13, pET14bNefW12, pET14bNefW10, pHen6HisGS, pHenPhoA6His, pHen-sdAb Nef1, pHen-sdAb Nef2, pHen-sdAb Nef5, pHen-sdAb Nef12, pHen-sdAb Nef19, pHen-sdAb Nef20, pET-sdAb Nef1, pET-sdAb Nef2, pET-sdAb Nef5, pET-sdAb Nef12, pET-sdAb Nef19, pET-sdAb Nef20, pcDNA-sdAb Nef19 having the sequences SEQ ID Nos. 13 to 30, respectively.

The genes encoding the sdAbs are inserted between unique restriction enzyme sites in the various plasmids.

The plasmids according to the invention are capable of expressing the sdAbs defined above in large amounts, in soluble forms, for example in bacteria. The regions encoding the sdAbs can be easily transferred into other prokaryotic or alternatively eukaryotic expression systems or else transferred into plasmids intended to be transfected in to eukaryotic cells.

The identification, in accordance with the invention, of a new target for intervention, represented by a direct inhibition of the functions of the Nef viral protein during natural infection with HIV, constitutes an original approach for developing antiviral molecules capable of disrupting HIV replication in the target cell, but also of improving the immune response of the infected patients.

The invention is therefore directed toward benefiting from the immunological properties of the antibody fragments in immunotherapy.

In a first embodiment, the invention is more especially directed toward the antibody fragments defined above, where appropriate, vectorized, for use as medicaments.

The pharmaceutical compositions of the invention are then characterized in that they contain an effective amount of at least one sdAb fragment as defined above, in combination with a pharmaceutically acceptable carrier.

According to one embodiment of the invention, these compositions can be used as antiviral medicaments. In this application, the sdAb fragments are vectorized in order to cross the cell membrane and to be released within the infected cell.

The vector, for example, a peptide sequence, may be conjugated to the sequence of the fragments.

As a variant, the vector is combined with the sdAb fragments and corresponds, for example, to lipid compounds.

According to another embodiment, the pharmaceutical compositions of the invention are used in immunotherapy in order to inhibit Nef molecules released into the plasma environment.

The pharmaceutical compositions above are advantageously in forms suitable for oral or injectable administration.

In another embodiment, the invention is directed toward a gene therapy medicament constituted of a transfection vector comprising a nucleic acid as defined above, encoding an sdAb fragment of the invention.

Vectors that can be used for gene therapy purposes comprise adenoviruses, adeno-associated viruses (AAVs) and retroviruses.

These medicaments are used for intracellular immunization by transfection of infected cells.

BRIEF DESCRIPTION OF THE DRAWINGS

Other characteristics and advantages of the invention will be given in the examples which follow, in which reference is made to FIGS. 1 to 10, which represent, respectively, FIG. 1, (A) titration curves for the sdAb Nef1-phage, sdAb Nef2-phage, sdAb Nef5-phage and sdAb Nef19-phage on the Nef protein adsorbed in the wells of a microplate and (B) curves of competition for the binding of the sdAb Nef5-phage and sdAb Nef19-phage to the Nef W10 protein adsorbed in the wells of a microplate, by the soluble Nef W10 protein, FIG. 2, an SDS-PAGE gel showing the fractions of the sdAb Nef19 protein purified on TALON, FIG. 3, (A) titration curves for sdAb Nef5 and sdAb Nef19 on the Nef W10 protein adsorbed in the wells of a microplate, (B) titration curve for sdAb Nef5 after amplification of the signal, and (C) curve of competition for the binding of sdAb Nef19 to the Nef W10 protein adsorbed in the wells of a microplate, by the soluble Nef W10 protein, FIG. 4, table of the affinity constants of sdAb Nef19, obtained by Biacore, FIG. 5, co-localization, analyzed by immuno-fluorescence, of sdAb Nef19 with the Nef protein in HeLa cells, FIG. 6, (A) flow cytometry analysis of the inhibition, by sdAb Nef19, of the effect of Nef on the level of expression of CD4 at the surface of HPB-ALL T cells and (B) flow cytometry analysis of the inhibition, by sdAb Nef19, of the effect of Nef on the level of expression of CD4 at the surface of HeLa cells, FIG. 7 (A) flow cytometry analysis of the inhibition, by sdAb Nef19, of the ability of Nef to interact with the cellular machinery of the endocytosis pathway when it is expressed in the form of a CD8-Nef fusion in HeLa cells and (B) immunofluorescence analysis of the inhibition, by sdAb Nef19, of the ability of Nef to interact with the cellular machinery of the endocytosis pathway when it is expressed in the form of a CD8-Nef fusion in HeLa cells, FIG. 8, analysis, by means of coimmuno-precipitation experiments, of the interaction of sdAb Nef19 with the Nef protein in 293T cells, FIG. 9, analysis of the inhibition, by sdAb Nef19, of the infection capacity of HIV-1 during a single replication cycle measured on (A) HeLa-CD4 cells and (B) HPB-ALL T cells, FIG. 10, analysis of the incorporation of sdAb Nef19 into viral particles.

DETAILED DESCRIPTION OF THE INVENTION

Example 1

Figure 1:
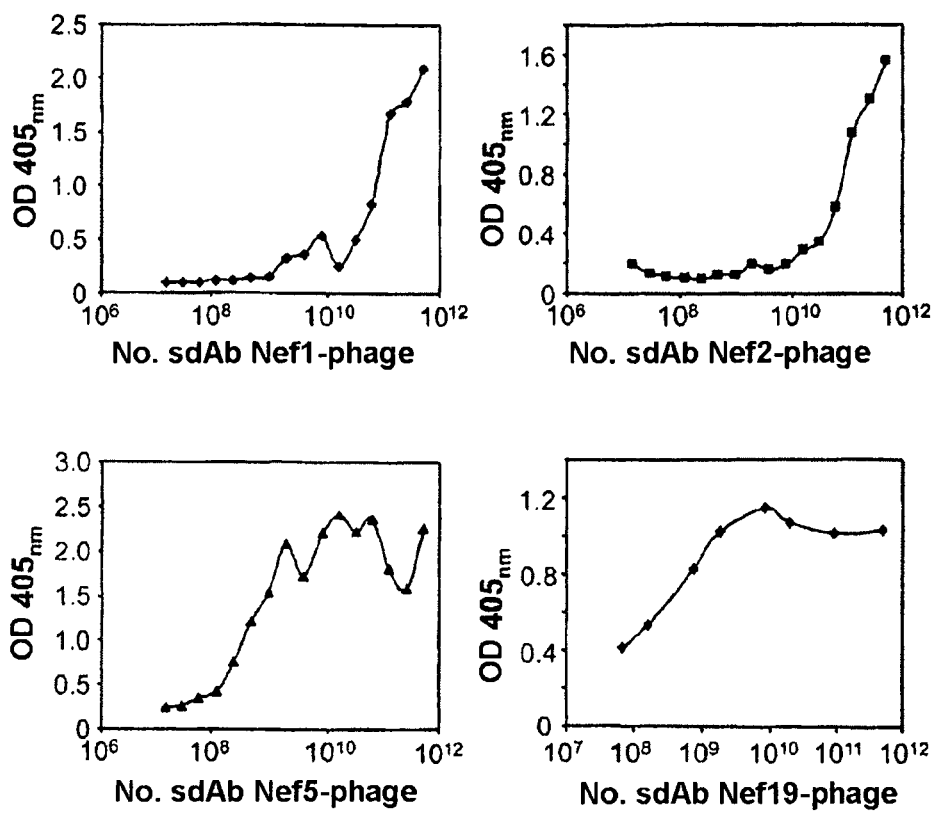
Figure 1:
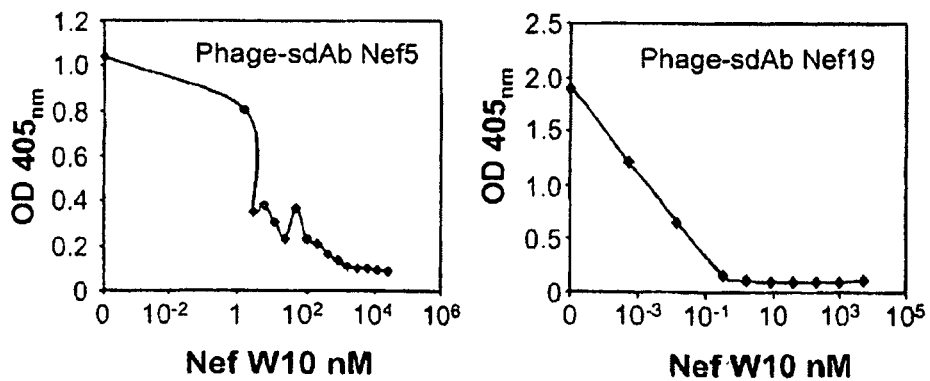

Construction of the various expression vectors for producing recombinant truncated Nef proteins in *E. coli* and for selecting sdAbs from sdAb-phage libraries a—Cloning of Various Versions of The Nef Protein in pET14b for their Production in *E. coli* a1—Obtaining of the Nef 13 Clone

Oligonucleotides Used:

5'Nef-Nco1-pET
SEQ ID No. 34:
CTTTAAGAAGGAGATATACCATGGGCCAYCAYCAYCAYCAYCAYGGNTCN
GAAGCACAAGAGGAGGAGGAG

3'Nef-Blp1-pET
SEQ ID No. 35:
GGGGTTATGCTAGTTATTGCTCAGCGTTCTTGAAGTACTCCGGATG

PCR Conditions:

One μl (5 ng) of plasmid pNef-GST (gene encoding amino acids 57 to 205 of the Nef protein inserted into the plasmid pGEX-2T (GE Healthcare)), 5 μl of 10× Deep-Vent buffer, 1 μl of 100 mM MgSO$_4$, 4 μl of 2.5 mM dNTP mix, 10 μM of each oligonucleotide (5' Nef-Nco-pET and 3' Nef-Blp1-pET), 0.5 U of Deep Vent in a final volume of 50 μl (94° C., 3 min; 94° C., 1 min; 55° C., 1 min; 72° C., 1 min, 30 cycles and then 72° C. 10 min). The PCR products are purified using a 2% agarose gel (Qiagen gel extraction kit, final volume 30 μl).

Cloning of the PCR Fragment into the Plasmid pET14b:

20 μl of the PCR fragment and 5 μl (2.5 μg) of the pET14b vector (Novagen) are cleaved with 10 U of Nco I and Blp I for 16H at 37° C. The enzymes are inactivated for 10 minutes at 65° C. Each DNA is then precipitated and taken up with 20 μl of H$_2$O.

The ligation is carried out with 5 μl of fragment, 0.5 μl of vector and 3 Weiss units of T4 DNA ligase (Biolabs) in a final volume of 10 μl for 2H at ambient temperature. Competent (CaCl$_2$ technique) BL21(DE3) bacteria are transformed with 5 μl of the ligation product. The plasmid pET14bNef13, the nucleotide sequence of which is given in the appendix (SEQ ID No. 13), is thus obtained, and makes it possible to produce the Nef13 clone, the amino acid sequence of which is given in the appendix (SEQ ID No. 31).

a2—Obtaining of the NefW12 Clone
Oligonucleotides Used:

```
5'Nef.Nco1.W
SEQ ID No. 36:
CTTTAAGAAGGAGATATACCATGGGCCACCACCATCATCATCACGGATCC
GCCTGGCTAGAAGCACAAGAGGAGGAGGAG

3'Nef-Blp1-pET
SEQ ID No. 37:
GGGGTTATGCTAGTTATTGCTCAGCGTTCTTGAAGTACTCCGGATG
```

PCR Conditions on pET14bNef13:

One µl (5 ng) of plasmid pET14bNef13, 10 µM of each oligonucleotide (5' Nef.Nco.W and 3' Nef-Blp1-pET), 0.5 U of Dynazyme (94° C., 3 min; 94° C., 1 min; 55° C., 1 min; 72° C., 1 min, 30 cycles, then 72° C., 10 min). The PCR products are purified using a 2% agarose gel (Qiagen gel extraction kit, final volume 50 µl).

Cloning of the PCR fragment into the plasmid pET14b: 20 µl of PCR fragment and 5 µl (2.5 µg) of the pET14b vector are cleaved with 10 U of NCo I and Blp I for 16H at 37° C. The enzymes are inactivated for 10 minutes at 65° C. Each DNA is then precipitated and the pellet is taken up with 20 µl of H$_2$O.

The ligation is carried out with 5 µl of fragment, 0.5 µl of vector and 3 Weiss units of T4 DNA ligase (Biolabs) in a final volume of 10 µl for 2H at ambient temperature. Competent (CaCl$_2$ technique) BL21(DE3) bacteria are transformed with 5 µl of the ligation product. The plasmid pET14bNefW12, the nucleotide sequence of which is given in the appendix (SEQ ID No. 14), is thus obtained and makes it possible to produce the Nef W12 clone, the amino acid sequence of which is given in SEQ ID No. 32.

a3—Obtaining of the Nef W10 Clone
Oligonucleotides Used:

```
5'Nef/pET
SEQ ID No. 38:
TTAAGAAGGAGATATACCATGGGCTGGCTNGARGCNCARGARGAGGAGGA
GGTGGGT

3'Nef/pJF-pET
SEQ ID No. 39:
GGGGTTATGCTAGTTAGCTCAGCAAGCTTAGGATCCGTGATGATGATGGT
GGTGTGCGGCCGCGTTCTTGAAGTACTCCGGATG
```

PCR Conditions on pET14bNef13:

One µl (5 ng) of plasmid pET14bNef13, 5 µl of 10× Dynazyme buffer, 4 µl of 2.5 mM dNTP mix, 10 µM of each oligonucleotide (5' Nef.Nco.W and 3' Nef-Blp1-pET), 0.5 U of Dynazyme, in a final volume of 50 µl (94° C., 3 min; 94° C., 1 min; 55° C., 1 min; 72° C., 1 min, 30 cycles then 72° C., 10 min). The PCR products are purified using a 2% agarose gel (Qiagen gel extraction kit, final volume 50 µl).

Cloning of the PCR fragment into the plasmid pET14b: 20 µl of PCR fragment and 5 µl (2.5 µg) of the pET14b vector are cleaved with 10 U of NCo I and Blp I for 16H at 37° C. The enzymes are inactivated for 10 minutes at 65° C. Each DNA is then precipitated and taken up with 20 µl of H$_2$O.

The ligation is carried out with 5 µl of fragment, 0.5 µl of the vector and 3 Weiss units of T4 DNA ligase (Biolabs) in a final volume of 10 µl for 2H at ambient temperature. Competent (CaCl$_2$ technique) BL21(DE3) bacteria are transformed with 5 µl of the ligation product. The plasmid pET14bNefW10, the nucleotide sequence of which is given in the appendix (SEQ ID No. 15), is thus obtained and makes it possible to produce the Nef W10 clone, the amino acid sequence of which is given in the annexe (SEQ ID No. 33).

All the genes encoding the various versions of Nef inserted into the plasmids of pET14b type were verified by sequencing on an ABI 310 with oligonucleotides internal to Nef:

```
5'Int.Nef
SEQ ID No. 40:        CACACAAGGCTACTTCCC

3' Int.Nef
SEQ ID No. 41:        CAACTGGTACTAGCTTGTAG
``` b—Construction of Phagemids pHen6HisGS and pHen6HisPhoA for Library Construction b1—Obtaining of the pHen6HisGS Phagemid The 6HisGlySer motif is inserted downstream of the sequence encoding the c-myc tag of the pHen1 phagemid (Hoogenboom et al., 1991) by overlapping PCR.

Oligonucleotides Used:

```
Sup-6HisGS/P3
SEQ ID No. 42:
5' CATCACCACCATCACCATGGGAGCTAGACTGTTGAAAGTTGTTTAGC
AAAACC

Inf-6HisGS/cmyc
SEQ ID No. 43:
5' GCTCCCATGGTGATGGTGGTGATGTGCGGCCCCATTCAGATCCTC

Amont[Upstream]-Hind3
SEQ ID No. 44:
5' AACAGCTATGACCATG

Aval[Downstream]-Bsm1
SEQ ID No. 45:
5' GCAAGCCCAATAGGAACCC
```

PCR1 and PCR2 Conditions:

One µl pHen1 at 50 ng/µl, 10 µl 10× Dynazyme buffer (Biolabs), 2 µl dNTP mix at 100 nM, 2 µl 5' oligonucleotide at 10 pmol/µl, 2 µl 3' oligonucleotide at 10 pmol/µl (pairs of primers used: PCR 1: Amont[Upstream]-Hind3 and Inf-6HisGS/cmyc; PCR 2: Sup-6HisGS/P3 and Aval[Downstream]-Bsm1), 0.7 µl of Dynazyme Taq polymerase (Biolabs), 82 µl H$_2$O.

PCR program used: 95° C., 3 min; 95° C., 45 s; 50° C., 45 s; 72° C., 45 s; 72° C., 3 min; 30 cycles. The size of the PCR1 and PCR2 fragments is verified on a 1% agarose gel and then the fragments are purified using the "Qiaquick gel extraction" kit (Qiagen). These two fragments are then used for the overlapping PCR3.

PCR 3 Conditions:

0.75 µl of each product of PCR1 and PCR2, 10 µl 10× Dynazyme buffer (Biolabs), 2 µl dNTP mix at 100 nM, 2 µl oligonucleotide Amont[Upstream]-Hind3 at 10 pmol/µl, 2 µl oligonucleotide Aval[Downstream]-Bsm1 at 10 pmol/µl, 0.7 µl of Dynazyme Taq polymerase (Biolabs), 82 µl H$_2$O.

PCR program used: 95° C., 3 min; 95° C., 45 s; 50° C., 45 s; 72° C., 45 s; 72° C., 3 min; 30 cycles. The size of the PCR3 fragment is verified on a 1% agarose gel and then the fragments are purified using the "Qiaquick gel extraction" kit (Qiagen). This fragment is then used for cloning.

The analysis of the PCR3 product on a 1% agarose gel is in accordance with what is expected (424 bp). This fragment was purified using the "Qiaquick gel extraction" kit (Qiagen) and was then cloned.

Cloning:

The PCR3 product is purified and cleaved, in a volume of 50 μl, with 20 units of HindIII restriction enzyme in the presence of BSA, at 37° C., for 4 h. Twenty units of the BsmI restriction enzyme are then added, and the sample is incubated at 65° C. for 4 h. The BsmI enzyme is denatured at 80° C. for 20 min.

Ten μg of pHen1 are cleaved, in a volume of 50 μl, with 20 units of HindIII restriction enzyme in the presence of BSA, at 37° C., for 4 h. Twenty units of the BsmI restriction enzyme are then added, and the sample is incubated at 65° C. for 4 h. The BsmI enzyme is denatured at 80° C. for 20 min.

The cleavage products are analyzed on a 0.7% agarose gel in order to verify the cleavage.

The PCR3 product and the pHen1 that have been cleaved with HindIII and BsmI are purified on a 0.7% gel using the "Qiaquick gel extraction" kit (Qiagen).

The PCR fragment is then cloned into the pHen1 phagemid between the HindIII and BsmI sites (insert DNA/phagemid molar ratio 1/5; 2000 units of T4 DNA ligase (Biolabs); 2 h at 20° C.). The ligase is denatured at 65° C. for 15 min.

Competent TG1 bacteria are transformed with 10 μl of ligation product. A phagemid preparation was then carried out using an isolated column and sequencing was carried out. The expression of the p3 protein of pHen6HisGS was verified by Western blotting using an antibody directed against the p3 protein. The sequence was found to be in accordance with what was expected. The nucleotide sequence of pHen6HisGS is given in the appendix (SEQ ID No. 16).

b2—Obtaining of the pHenPhoA6His Phagemid

The new pHen6HisGS vector can be directly used for constructing the naive library. It is advantageous to improve it in order to facilitate the evaluation of the cloning efficiency. This is because the isolation of VHH (or sdAb) with good specificity and in large number requires libraries of wide diversity to be obtained. Very good cloning efficiency is therefore necessary during library construction.

The phoA gene encoding alkaline phosphatase is inserted into the pHen6HisGS phagemid upstream of the gene encoding the c-myc tag.

This gene, inserted in the correct reading frame, allows the synthesis of a "PhoA-cmyc-6HisGs-p3" fusion protein which has the phosphatase activity. A colorimetric selection thus makes it possible to distinguish the vectors closed up on themselves (blue colonies) from the vectors having inserted, in place of the PhoA gene, the genes encoding VHH or sdAb (white colonies).

Firstly, the sequencing coding PhoA was amplified, from the plasmid p55PhoA6HisGS/NAB- (Baty et al., CNRS/INSERM patent WO/2006/064136) with specific primers for cloning into the pHen6HisGS phagemid.

Oligonucleotides Used:

5' PhoA/pHen
SEQ ID No. 46:
5' GGATTGTTATTACTCGCGGCCCAGCCGGCCATGGCAGCCGATCCTCG
AGAGCTCCCG

3' PhoA/pHen
SEQ ID No. 47:
5' GAGATGAGTTTTTGTTCTGCGGCCGCTTTCAGCCCCAGAGCGGCTTT
C

PCR Conditions:

One μl p55PhoA6HisGS/NAB- at 50 ng/μl, 10 μl 10× Dynazyme buffer (Biolabs), 2 μl dNTP mix at 100 nM, 2 μl 5' PhoA/pHen oligonucleotide at 10 pmol/μl, 2 μl 3' PhoA/pHen oligonucleotide at 10 pmol/μl, 0.7 μl of Dynazyme Taq polymerase (Biolabs), 82 μl $H_2O$.

PCR program used: 95° C., 3 min; 95° C., 1 min; 60° C., 1 min; 72° C., 1 min; 72° C., 10 min; 35 cycles.

The PCR product is analyzed on a 1% agarose gel. The PCR product purified using the "Qiaquick gel extraction" kit (Qiagen) is cleaved, in a volume of 50 μl, with 20 units of SfiI restriction enzyme in the presence of BSA, at 50° C., 16 h. Twenty units of the NotI restriction enzyme are then added, and the sample is incubated at 37° C. for 4 h.

Ten μg of pHen6HisGS are cleaved, in a volume of 50 μl, with 20 units of the SfiI restriction enzyme in the presence of BSA at 50° C. for 4 h. Twenty units of the NotI restriction enzyme are then added, and the sample is incubated at 37° C. for 4 h.

The PCR product and the pHen6HisGS that have been cleaved with SfiI and NotI are purified on a 0.7% gel using the "Qiaquick gel extraction" kit (Qiagen).

Cloning:

The PCR fragment is then cloned into the pHen6HisGS phagemid between the SfiI and NotI sites (insert DNA/phagemid molar ration 1/1; 1000 units of T4 DNA ligase (Biolabs); 2 h at 20° C.). The ligase is denatured at 65° C. for 15 min.

Competent TG1 bacteria are transformed with 10 μl of ligation product, and then plated out on LB medium/100 μg/ml ampicillin/30 μg/ml BCIP.

A preparation of the phagemid was then prepared using a blue colony. The expression of the PhoA-cmyc-6HisGS-p3 fusion protein was verified, as was the efficiency of the phagemid for infection. The nucleotide sequence of pHenPhoA6His phagemid is given in the appendix (SEQ ID No. 17).

c—Immunization of Llamas and Purification of B Lymphocytes

A male llama was immunized with region 57 to 205 of the recombinant Nef protein (Nef57-205) of HIV-1.

The animal was immunized every month, for three months, with 500 μg of Nef57-205. One hundred ml of blood were taken 15 days after each immunization. For each of the samples taken, the sera and the purified antibodies (IgG1, 2 and 3) were titered in order to detect the presence of antibodies against the Nef57-205 immunogen. The B lymphocytes were then purified on a Ficoll gradient (histopaque-1077, Sigma-Aldrich), and then washed twice with PBS.

d—Construction of Phage-sdAb Libraries: Purification of Total RNA, Reverse Transcription, PCR1, PCR2 and Cloning into the pHen6HisGS and pHenPhoA6His Phagemids d1—Purification of Total RNA Total RNA of the B lymphocytes is extracted according to the method using guanidium isothiocyanate (Chomczynski and Sacchi, 1987). After phenol/chloroform extraction in an acidic medium, the total RNA is precipitated with ethanol. The quality of the RNA and the quantification thereof are evaluated on a 1% agarose gel. It is then converted to cDNA by reverse transcription.

d2—Reverse Transcription and PCRs

Oligonucleotides Used:

3' CH2FORTA4
SEQ ID No. 48:
CGCCATCAAGGTACCAGTTGA

-continued

3'CH2-2
SEQ ID No. 49:
GGTACGTGCTGTTGAACTGTTCC

3'RC-IgG2
SEQ ID No. 50:
GGAGCTGGGGTCTTCGCTGTGGTGCG

3'RC-IgG3
SEQ ID No. 51:
TGGTTGTGGTTTTGGTGTCTTGGGTT

5'VH1-Sfi
SEQ ID No. 52:
CATGCCATGACTCGCGGCCCAGCCGGCCATGGCCCAGGTGCAGCTGGTGCAGTCTGG

5'VH2-Sfi
SEQ ID No. 53:
CATGCCATGACTCGCGGCCCAGCCGGCCATGGCCCAGGTCACCTTGAAGGAGTCTGG

5'VH3-Sfi
SEQ ID No. 54:
CATGCCATGACTCGCGGCCCAGCCGGCCATGGCCGAGGTGCAGCTGGTGGAGTCTGG

5'VH4-Sfi
SEQ ID No. 55:
CATGCCATGACTCGCGGCCCAGCCGGCCATGGCCCAGGTGCAGCTGCAGGAGTCGGG

3'VHH-Not
SEQ ID No. 56:
CACGATTCTGCGGCCGCTGAGGAGAC(AG)GTGACCTGGGTCC

Five μg of total RNA are hybridized with 1 pmol of 3' CH2FORTA4 (Arbabi Ghahroudi et al., 1997) or CH2-2 oligonucleotide specific for the CH2 domain of llama single heavy-chain IgGs, and reverse-transcribed with 150 U of superscript II (BRL) for 30 min at 50° C. The oligonucleotides specific for the hinge regions of IgG2 and 3, 3' RC-IgG2 and 3' RC-IgG3, can also be used. The single-stranded cDNAs are purified on beads (BioMagR Carboxyl Terminator, Polyscience Inc) and eluted with 17 μl of 10 mM Tris-acetate, pH 7.8.

d3—PCR1, PCR2

PCR1 Conditions:

Four μl of cDNA are amplified by PCR with 0.5 U of Dynazyme Extend DNA polymerase (Finnzymes), 10 pmol of the same 3' CH2FORTA4 or CH2-2 primer and 10 pmol of the four 5' VH1-4 Sfi primers specific for the VH domain of human IgGs, in a volume of 50 μl (94° C., 3 min; 94° C., 1 min; 60° C., 1 min; 72° C., 1 min; 37 cycles, then 72° C., 10 min).

Three DNA fragments are amplified: a fragment of approximately 900 bp encoding the VH-CH1-CH2 domains of IgG1; and 2 fragments of approximately 600 bp encoding the VHH-CH2 domains of IgG2 and 3.

PCR2 Conditions:

The 600 bp fragments are purified on a 1% agarose gel ("Qiaquick gel extraction" kit, Qiagen) and then amplified by PCR with 1 U of Deep Vent (Biolabs) and 10 pmol of the four 5' VH1-4 Sfi primers specific for the VH domain of human IgG and 10 pmol of the 3' VHH-NotI primer (94° C., 3 min; 94° C., 45 sec; 65° C., 45 sec; 72° C., 45 sec; 15 cycles, then 94° C., 45 sec; 60° C., 45 sec; 72° C., 45 sec; 15 further cycles, then 72° C., 10 min).

The fragments of approximately 400 bp encoding the VHHs are purified on a 1% agarose gel ("Qiaquick gel extraction" kit, Qiagen), combined and precipitated with ethanol. They are then cleaved with the NcoI and NotI, or BglI and NotI, restriction enzymes (Biolabs) so as to be cloned into the pHen16hisPhoA phagemid at the NcoI and NotI or SfiI and NotI sites.

d4—Cloning into the Phagemids

Preparation of the pHen6HisGS Phagemid (or pHen6HisPhoA phagemid for the "naive" library):

Twenty μg of pHen6HisGS phagemid are cleaved, in a volume of 300 μl, with 50 U of SfiI in the presence of BSA, at 50° C. for 16 h; or with 50 U of NcoI in the presence of BSA, at 37° C. for 16 h. The linearized phagemid is purified on a 0.7% agarose gel ("Qiaquick gel extraction" kit, Qiagen). The DNA eluted is then cleaved with 50 U of NotI at 37° C. in a volume of 200 μl for 16 h. The enzyme is destroyed by heat for 15 minutes at 65° C. and the DNA is extracted with phenol/chloroform and precipitated with ethanol. The cleaved pHen6HisGS is checked on a 0.7% agarose gel, quantified and adjusted to 200 ng/μl.

Preparation of the DNA Fragments Encoding the sdAbs:

Five μg of VHH fragments are cleaved, in a volume of 300 μl, with 50 U of BglI and NotI in the presence of BSA, at 37° C. for 16 h; or with 50 U of NcoI and NotI in the presence of BSA, at 37° C. for 16 h. The enzymes are denatured at 65° C. for 15 min; the DNAs are then extracted with phenol/chloroform and precipitated with ethanol in the presence of 10 μg of glycogen (Roche). The VHH fragments cleaved with NcoI and NotI are purified on a 1% agarose gel, and then checked on a 2% agarose gel, quantified and adjusted to 100 ng/μl.

Ligation:

One hundred and fifty ng of pHen6HisGS cleaved with SfiI and NotI are ligated with 60 ng of VHH fragment cleaved with BglI and NotI, in a volume of 20 μl, with 2000 U of T4 DNA ligase (Biolabs) at 16° C. for 17 h.

The ligase is inactivated at 65° C. for 15 min, and the ligation product is cleaved with 20 U of XhoI (Biolabs) so as to eliminate the unligated residual vector, at 37° C. for 4 h. Six ligations are thus performed. The ligation products are then combined in two tubes and extracted with phenol/chloroform, precipitated in the presence of 10 μg of glycogen and taken up in 2×18 μl of ultrapure H₂O. Two μl are used by electroporation. The colonies from various electroporations are combined. The male llama sdAb-phage library represents 4.1×10⁴ clones.

e—Construction of the "Naive" sdAB-Phage Library Using Nonimmunized Llamas

The library was constructed exactly as described for the immune library, with the following modifications:

the phagemid used is pHenPhoA6His,
the blood (approximately 2400 ml) was taken from about sixty nonimmunized llamas originating from 4 different farms.

The "naive" sdAb-phage library represents 3 10⁷ clones.

f—Selection of sdAbs from the Libraries Using the Phage-Display Technique

The various sdAbs were isolated using the phage-display technique (Smith, 1985; Hoogenboom et al., 1991) irrespective of the library used.

f1—Production of the Phage Library:

Ten μl of the library stock (TG1 cells transformed with the phagemids) are inoculated into 50 ml of 2TY containing 100 μg/ml of ampicillin and 2% glucose, and incubated at 37° C. until an OD600 equal to 0.5 is obtained. Five ml of the culture are then infected with 5 ml of M13KO7 at 10¹³ pfu/ml and incubated for 30 min at 37° C. with no agitation. After centrifugation, the phage pellet is taken up in 25 ml of 2TY containing 100 μg/ml of ampicillin and 25 μg/ml kanamycin. The culture is incubated for 16 h at 30° C. with agitation. The phages are then precipitated with 1/5 vol of 2.5M NaCl/20% PEG 6000 and concentrated 25-fold in PBS.

f2—sdAb Selection:

Two hundred μl of streptavidin-coated beads (Dynabeads M-280, Dynal) are equilibrated with 1 ml of 2% milk/PBS for 45 min at ambient temperature with agitation on a wheel. $10^{12}$ phages from the production previously described are also equilibrated with 2% milk/PBS in a final volume of 500 μl for 60 min at ambient temperature with agitation on a wheel.

The beads are compacted with a magnet, suspended in 250 μl of 2% milk/PBS and incubated with 200 μl of biotinylated antigen for 30 min at ambient temperature on a wheel. 150, 75 and 25 nM, final concentration, of biotinylated antigen are used in the 1st, 2nd and 3rd round, respectively.

500 μl of phages are added to the 450 μl of beads/antigen-biotin for 3 h at ambient temperature with agitation on a wheel. The beads/antigen-biotin/phage mixture is washed 5 times with 800 μl of 4% milk/PBS, and then transferred into a new Eppendorf tube. Five other washes are carried out with 800 μl of PBS/0.1% Tween, and the mixture is then transferred into a new Eppendorf tube. Finally, 5 washes are carried out with 800 μl of PBS.

The antibody phages bound to the beads/antigen-biotin are suspended in 200 μl of PBS and incubated for 30 min at 37° C., with no agitation, with 1 ml of TG1 made competent for binding of the phages to the pili (competent cells: starting from an overnight culture of TG1 in 2YT, a 1/100 dilution is made and 50 ml of 2YT are inoculated at 37° C. with agitation until an OD600 close to 0.5 is obtained). At each selection, the phages are counted and amplified for a further round of selection.

f3—Counting the Selections:

Dilutions of the TG1 cells transfected with the phages (see above) of $10^{-2}$ to $10^{-5}$ are made with 2YT. One, 10 and 100 μl of each dilution are plated out onto Petri dishes (2YT/100 μg/ml ampicillin/2% glucose). The dishes are incubated for 16 h at 30° C.

f4—Plating Out the Selection for Isolation of Colonies:

The 5 ml of transfected TG1 are centrifuged for 10 min at 3000 g in order to concentrate the cells, and the pellet is taken up with 1 ml of 2YT. Two hundred and fifty μl are plated out per Petri dish (12 cm×12 cm)(2TY/100 μg/ml ampicillin/2% glucose) and incubated for 16 h at 30° C.

f5—Selection Results Assessment f6—"Immune" Library

Two sdAbs specific for the Nef protein were isolated by this method: sdAb Nef19 (SEQ ID Nos. 1 and 7) and sdAb Nef20 (SEQ ID Nos. 2 and 8).

f7—"Naive" Library

Four sdAbs specific for the Nef protein were isolated by this method: sdAb Nef1 (SEQ ID Nos. 3 and 9), sdAb Nef2 (SEQ ID Nos. 4 and 10), sdAb Nef5 (SEQ ID Nos. 5 and 11) and sdAb Nef12 (SEQ ID Nos. 6 and 12).

The sequences were aligned according to the IMGT international nomenclature (The international ImmunoGeneTics information system)(Lefranc, 2003).

g—Production of sdAb-Phages and Counting g1—Unitary sdAb-Phage Production:

Twenty ml of 2TY (100 μg/ml ampicillin; 2% glucose) are inoculated with one isolated colony of TG1 containing the phagemid corresponding to the sdAb-phage selected. The culture is incubated at 37° C. with agitation until an OD600 nm close to 0.5 is obtained. Five ml of this culture are infected with 5 to 10 μl of M13KO7 helper phage ($10^{13}$ pfu/ml) and incubated for 30 min at 37° C. in a water bath (with no agitation). The culture is centrifuged for 10 min at 3000 g and the supernatant is removed. The pellet is taken up with 25 ml of 2TY (100 μg/ml ampicillin; 25 μg/ml kanamycin). The culture is incubated at 30° C. for 16 h with agitation, and then the vessel is placed in ice for 10 min. The culture is then centrifuged for 20 min at 3000 g, 4° C. The supernatant is removed and precipitated by adding 1/5 volume of 2.5M NaCl/20% PEG 6000 for 1 h in ice. The solution is centrifuged for 20 min at 3000 g, 4° C. The pellet is taken up with 1 ml of PBS and transferred into a siliconized Eppendorf tube. A rapid precipitation is carried out by adding 200 μl of NaCl/PEG, followed by centrifuging at 13 000 rpm. The pellet is taken up with 1 ml of PBS and centrifuged for 1 min at 13 000 rpm. The supernatant is filtered through 0.45 μm and transferred into a siliconized Eppendorf tube and then stored at 4° C.

g2—Counting of the sdAb-Page Solution:

TG1 cells are cultured in 2YT at 37° C. Successive dilutions (10-fold) of sdAb-phage are made in siliconized Eppendorf tubes containing 500 μl of 2YT. When the TG1 cells are at an OD600 nm of 0.5, 500 μl of TG1 are added, and then the cells are left for 30 min at 37° C. without agitation. One hundred μl of each tube are plated out on 2YT (100 μg/ml ampicillin; 2% glucose) Petri dishes. The dishes are incubated for 16 h at 30° C. or 37° C. The colonies are counted in order to determine the number of sdAb-phages in the starting solution. This solution will be used to characterize the sdAb-phages by ELISA.

h—Characterization of Anti-Nef sdAb-Phages by ELISA h1—sdAb-Phage ELISA:

Five μg/ml of biotinylated antigen (Nef W10) are bound to a streptavidin plate (BioBind Assembly Streptavidin Coated, ThermoLabsystems) presaturated with 2% milk/PBS. Various sdAb-phage dilutions are brought into contact with the antigen. The antigen/antibody binding is detected by means of an ELISA composed of a monoclonal antibody directed against the P8 protein of the phage (HRP/anti-M13 monoclonal conjugate, Pharmacia). Addition of the substrate, 10 mg ABTS (diammonium salt of 2,2'-azinobis(3-ethylbenzothiazoline-6-sulfonic acid), to 20 ml of revealing buffer (18 ml PBS, 1 ml of 1M citric acid, 1 ml of 1M sodium citrate, 10 ml of 30% $H_2O_2$) makes it possible to read the reaction at 405 nm (Tecan).

FIG. 1A shows the results obtained with the sdAb Nef1-phage, sdAb Nef2-phage and sdAb Nef5-phage obtained with the "naive" library and the sdAb Nef19-phage obtained from the "immune" library. In all the titration curves, a decrease in the measurement of the interaction between the sdAb-phages and the biotinylated Nef W10 protein, bound in streptavidin-coated wells of a microplate, is observed when the amount of sdAb-phage decreases. In order to demonstrate that this interaction is specific, competition ELISAs were carried out. For this, a constant amount of sdAb-phage (approximately $10^{10}$ phage particles) was pre-incubated with various amounts of nonbiotinylated Nef W10 protein for 16 h at 4° C. The ELISAs are then carried out as described previously. FIG. 1B shows that the binding of the sdAb Nef5-phage and the sdAb Nef19-phage to the biotinylated Nef W10 decreases when the nonbiotinylated Nef W10 protein is increased in the assay. This decrease proves the specificity of the interaction between the sdAb-phages and the Nef W10 protein. Equivalent results are obtained with the other sdAb-phages selected.

i—Production and Purification of sdAbs from the pHen6HisGS or pHen6HisPhoA Phagemids i1—sdAb Production:

An isolated colony is inoculated into 3 ml of 2YT/100 µg/ml ampicillin/2% glucose and incubated at 37° C. with agitation. Fifty ml of 2YT/100 µg/ml ampicillin/2% glucose are then inoculated with a dilution of the previous culture and incubated for 16 h at 30° C. with agitation. Four hundred ml of 2YT/100 µg/ml ampicillin are inoculated with the equivalent of 0.1 OD600 nm units, and incubated at 30° C. with agitation, until an OD600 nm of 0.5 to 0.7 is obtained. The culture is then induced with IPTG (isopropyl-β-D-thiogalactopyranoside; 0.1 mM of final concentration) and cultured at 30° C. for 16 h.

i2—Extraction of the Soluble Fraction of the Periplasm:

The cultures from which the sdAbs are produced are centrifuged at 4200 g, 4° C., for 40 min. The pellet is taken up in 4 ml of ice-cold TES (0.2M Tris-HCl, ph 8.0; 0.5 mM EDTA; 0.5M sucrose). 160 µl of lysozyme (10 mg/ml in TES, freshly prepared) are then added, followed by 24 ml of cold TES diluted to 1/2 in $H_2O$. The mixture is incubated for 30 min in ice. 150 µl of DNAse (10 mg/ml) and a final concentration of 5 mM of $MgCl_2$ are then added for 30 min at ambient temperature. After centrifugation at 4200 g, 4° C., for 40 min, the supernatant (corresponding to the periplasmic fraction) is recovered. The solution is dialyzed for 16 h against the equilibrating buffer (50 mM sodium acetate, 0.1M NaCl, pH 7.0).

i3—sdAb Purification:

The column (BD TALON™ Metal affinity, BD Biosciences Clontech) is equilibrated with the equilibrating buffer (50 mM sodium acetate, 0.1M NaCl, pH 7.0). The periplasmic fraction is loaded onto the column. After the column has been washed with 5 volumes of equilibrating buffer, the sdAb is eluted by means of a pH or imidazole gradient (gradient between the equilibrating buffer, pH 7.0, and the 50 mM sodium acetate solution, pH 5.0, or the imidazole solution from 0 to 200 mM). Each fraction is checked on an SDS/PAGE gel (15% acrylamide) after staining with coomassie blue. The fractions of interest are combined and dialyzed against PBS. The sdAb is concentrated on a membrane (Amicon Ultra 5000MWCO, Millipore) and assayed by the Lowry colorimetric method using the Biorad Protein Assay kit.

Figure 2:
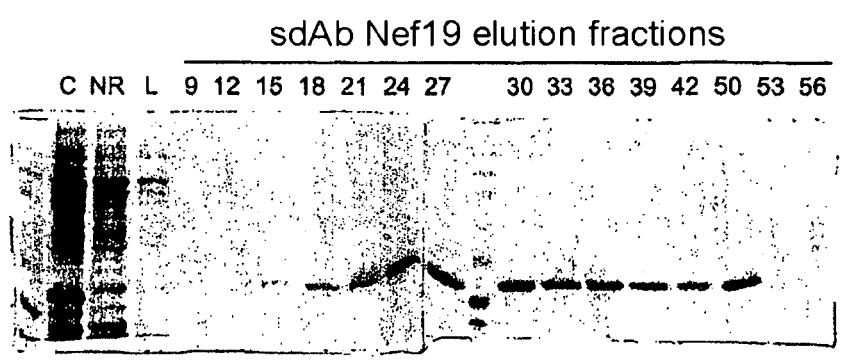

FIG. 2 shows a purification profile (C: load; NR: fraction not retained on the column; L: loading buffer wash). sdAb Nef19 is eluted (fractions 9 to 56) with a pH gradient of 7 to 5.

i4—Characterization of the Anti-Nef sdAbs by ELISA

Five µg/ml of biotinylated antigen (Nef W10) are bound to a streptavidin plate (BioBind Assembly Streptavidin Coated, ThermoLabsystems) presaturated with 2% milk/PBS. Each sdAb (range of 0.001 µg/ml to 1 µg/ml) is bound to the antigen adsorbed in the microwells. The binding is revealed with a monoclonal antibody, 9E10, directed against the c-myc tag (Santa Cruz Biotechnology, Inc), diluted to 1/1000, and a peroxidase-coupled goat polyclonal antibody directed against mouse IgG, diluted to 1/5000 (ref 55556, ICN), in the presence of ABTS (diammonium salt of 2,2'-azinobis(3-ethylbenzthiazoline sulfonate)(Roche).

Figure 3:
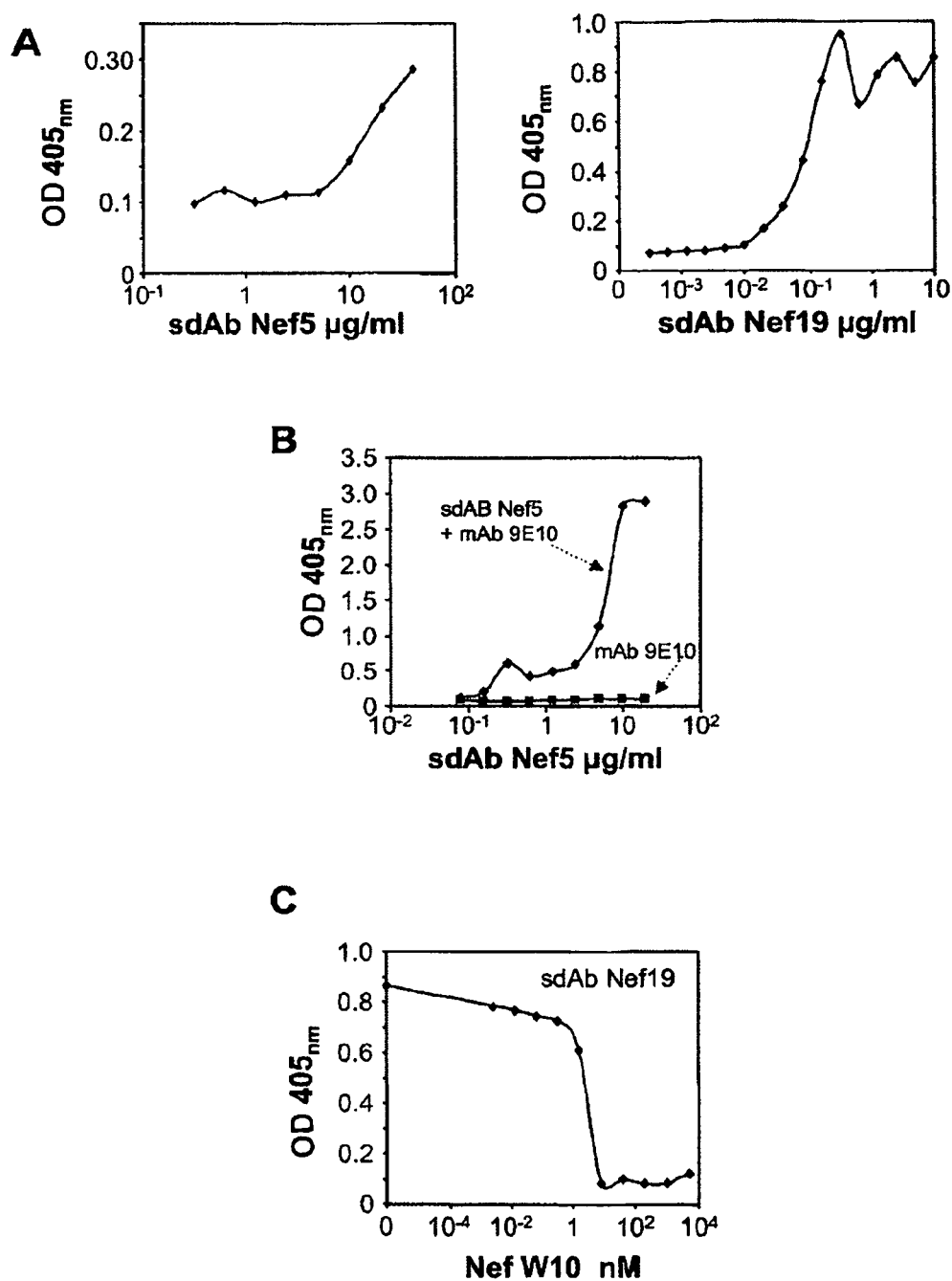

FIG. 3A gives the results obtained with sdAb Nef5 and sdAb Nef19. In all the titration curves, a decrease in the measurement of the interaction between the sdAbs and the biotinylated Nef W10 protein, bound in streptavidin-coated wells of a microplate, is observed when the amount of sdAb decreases. Since sdAb Nef5 has a lower affinity than sdAb Nef19, an amplification of the signal (FIG. 3B) was obtained by preincubating sdAb Nef5 with the mAb 9E10 for 1 h at 25° C. before depositing in the wells of the microplate. As a control, the mAb 9E10 was used in the absence of sdAb.

As for the sdAb-phages, competition ELISAs were carried out. For this, a constant amount of sdAb (5 µg/ml) was preincubated with various amounts of nonbiotinylated Nef W10 protein for 16 h at 4° C. The ELISAs are then carried out as described previously. FIG. 3C shows that the binding of sdAb Nef19 to the biotinylated Nef W10 decreases when the amount of nonbiotinylated Nef W10 protein in the assay is increased. This decrease proves the specificity of the interaction of sdAb Nef19 for the Nef W10 protein. Equivalent results are obtained with the other sdAbs.

j—Cloning of sdAb Nef19 into the Plasmid pET14bNefW10

10 µl of the pET14bNefW10 vector and 5 µl of the pHen-sdAb Nef19 vector are cleaved with 10 U of NcoI and NotI for 16 h at 37° C. The fragments are purified on 1% agarose (Qiagen gel extraction kit, final volume 50 µl for the pET14bNefW10 vector and 20 µl for the fragment corresponding to the sequence of sdAb Nef19).

The ligation is carried out with 10 µl of fragment and 1 µl of vector in a final volume of 15 µl in the presence of 3 Weiss units of T4 DNA ligase (Biolabs) for 2 h at ambient temperature.

Competent ($CaCl_2$ technique) BL21(DE3) bacteria are transformed with 7.5 µl of the ligation product. The plasmid pET-sdAb Nef19 (SEQ ID No. 28), the sequence of which is indicated in the appendix, is obtained.

h—Affinity Constants of The Anti-Nef Antibody Using Biacore

BIACORE uses the principle of surface plasmon resonance (SPR) to follow, in real time, the interactions between molecules without labeling said molecules. One of the interaction partners is covalently immobilized on a biosensor, while the other is injected in a continuous stream. The principle of detection by SPR makes it possible to follow the changes in mass at the surface of the biosensor, due to the formation and then the dissociation of molecular complexes. The response, quantified in resonance units (RU), is a direct indication of the degree of binding of the analyte by the measurement of the variation in refractive index. The recording of the signal (a sensorgram) is processed mathematically so as to obtain the association rate constant ka and the dissociation rate constant kd and the equilibrium association constant KA (KA=ka/kd) and the equilibrium dissociation constant KD (KD=kd/ka).

The interactions between Nef W10 and sdAb Nef19 produced either from the periplasm (sdAb Nef19P) or from the cytoplasm (sdAb Nef19C) of bacteria were studied on a BIACORE 3000 equipped with a CM5 biosensor on which 1089 RU of Nef W10 were covalently immobilized according to the standard amine-coupling procedure proposed by BIACORE (activation with NHS/EDC). sdAb Nef19P or sdAb Nef19C (in buffer: 10 mM HEPES; 150 mM NaCl; 3 mM EDTA; 0.005% surfactant P20) is then injected. In parallel, the injections are carried out on a control channel which has undergone the same chemical coupling, but without injection of protein. The affinity constants for sdAb Nef19P and sdAb Nef19C, of SEQ ID Nos. 1 and 7, are indicated in FIG. 4 (it should be noted that sdAb Nef19P and sdAb Nef19C have the same amino acid sequences).

k—Construction of The Plasmid Allowing Intracellular Expression of the sdAB Nef19 in Eukaryotic Cells and Study of the Cellular Distribution of sdAb Nef19 k1—Obtaining of the Plasmid pcDNA-sdAb Nef19
Oligonucleotides Used:

```
SEQ ID No. 57:
ANefEcoK5p
5'GAATTCCACCATGGCCGAGGTGCAGCTGGTG3'

SEQ ID No. 58:
ANefXho3p
5'CTCGAGCTAGCTCCCATGGTGATGGTG
```

The sequence encoding sdAb Nef19, truncated by removal of its signal peptide but tagged at its C-terminal end with the c-myc and 6His epitopes, was amplified by PCR from the pHEN-sdAb Nef19 vector using the 2 nucleotide primers ANefEcoK5p and ANefXho3p.

PCR Conditions:

One µl of pHen-sdAb Nef19 at 50 ng/µl, 10 µl of 10× Dynazyme buffer (Biolabs), 2 µl of dNTP mix at 100 nM, 2 µl of 5' oligonucleotide at 10 pmol/µl, 2 µl of 3' oligonucleotide at 10 pmol/µl (pairs of primers used: ANefEcoK5p and ANefXho3p), 0.7 µl of Dynazyme Taq polymerase (Biolabs), 82 µl of $H_2O$.

PCR program used: 95° C., 3 min; 95° C., 45 s; 50° C., 45 s; 72° C., 45 s; 72° C., 3 min; 30 cycles. The size of the PCR fragment is verified on a 1% agarose gel, and the fragments are then purified using the "Qiaquick gel extraction" kit (Qiagen).

Cloning:

Twenty µl of the purified PCR product are cleaved, in a volume of 100 µl, with 10 U of EcRI restriction enzyme and 10 U of XhoI restriction enzyme in the presence of BSA, at 37° C., for 12 h. The enzymes are then denatured at 65° C. for 20 min.

The pcDNA3.1+ vector (Invitrogen) was used for the expression of sdAb Nef19 in mammalian cells. 2.5 µg of pcDNA3.1+ are cleaved, in a volume of 100 µl, with 10 units of EcoRI restriction enzyme and 10 units of XhoI restriction enzyme in the presence of BSA, at 37° C., for 12 h. The enzymes are then denatured at 65° C. for 20 min.

The digestion products are analyzed on a 0.7% agarose gel in order to verify the digestion.

The PCR product and the pHen-sdAb Nef19 that have been cleaved with EcoRI and HindIII are purified on a 0.7% gel using the "Qiaquick gel extraction" kit (Qiagen).

The ligation is carried out with 5 µl of PCR fragment, 0.5 µl of the vector and 3 Weiss units of T4 DNA ligase (Biolabs) in a final volume of 10 µl, for 2 h at ambient temperature.

Competent TG1 bacteria are transformed with 10 µl of ligation product. A preparation of the plasmid was then carried out using an isolated colony and sequencing was carried out. The resulting plasmid, called pcDNA-sdAb Nef19, allows the production of sdAb Nef19 in eukaryotic cells transfected with this plasmid. The sequence of pcDNA-sdAb Nef19 is given in the appendix (SEQ ID No. 30).

k2—Colocalization of sdAb Nef19 with the Nef Protein at the Level of Cytoplasmic Membrane Structures The intracellular distribution of sdAb Nef19 was analyzed by indirect immunofluorescence on HeLa cells transiently expressing the Nef-GFP fusion protein or the GFP control protein, the expression vectors of which have been previously described (Burtey et al., 2007). The cells ($4\times10^5$) were transfected by the lipofection technique with Lipofectamine 2000 (Invitrogen) according to the procedure recommended by the manufacturer.

24 h after transfection, the cells were fixed for 20 min at 4° C. with a solution of PBS/4% paraformaldehyde (PFA), and then permeabilized with a solution of PBS/0.1% Triton X100 for 10 min. The sdAb was then detected using an antibody (Ab) directed against the c-myc epitope (9E10, Roche) in PBS/0.1% BSA, and then an anti-mouse IgG second Ab coupled to Alexa594 (Jackson Laboratories). The localization of the sdAb was compared with that of Nef-GFP by fluorescence microscopy using a Leica DMB microscope, and the images were edited using the Adobe Photoshop software.

Figure 5:
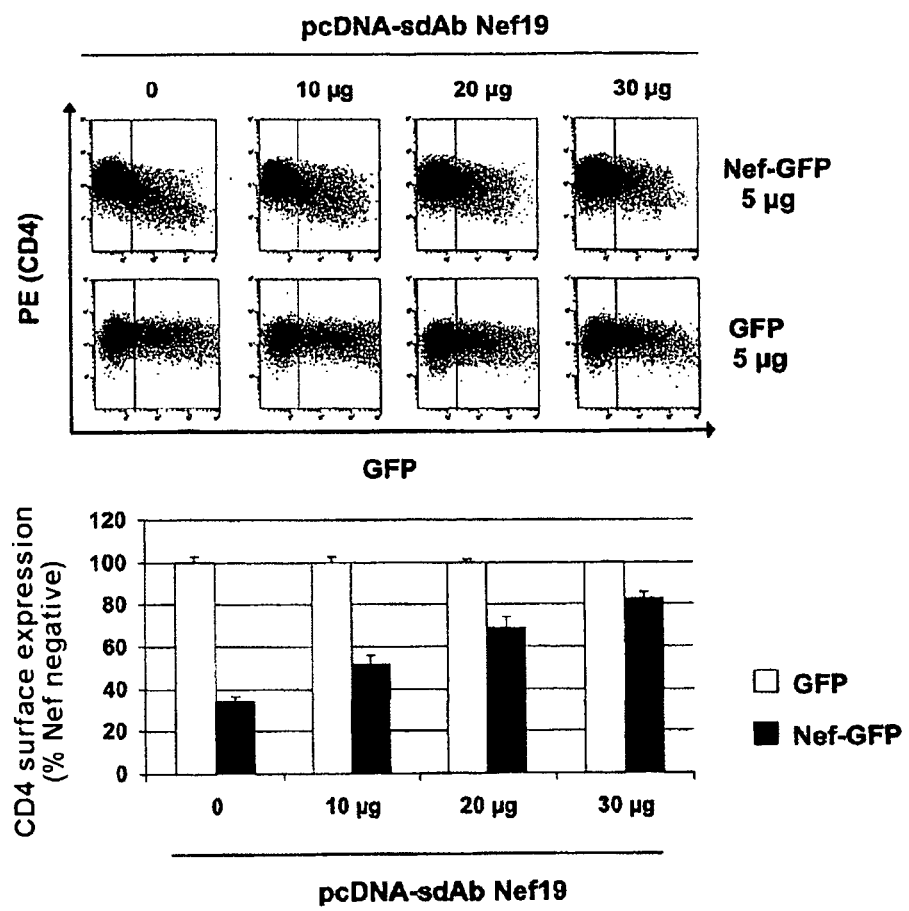
Figure 5:
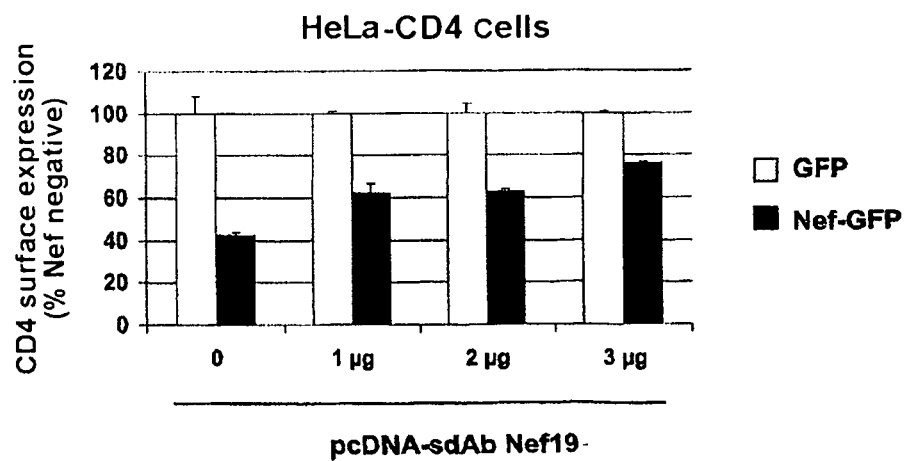

The results are illustrated in FIG. 5. While the sdAb is distributed diffusely between the cytoplasm and the nucleus (part A, central panel) in the cells expressing the GFP control protein (left panel), it becomes redistributed towards cytoplasmic membrane structures located in the perinuclear region where it colocalizes perfectly with the Nef-GFP protein (part B).

l—Study of the Effect of sdAb Nef19 on the Functional Properties of Nef l1—Inhibition of the Effect of Nef on the Level of CD4 Expression at the Cell Surface In order to explore the potential effects of sdAb Nef19 on the functional properties of Nef, its ability to modulate the expression of the CD4 receptor at the surface of CD4+ T lymphocytes was firstly analyzed in cells expressing the sdAb. Human T lymphoid cells of the HPB-ALL line ($10^7$), constitutively expressing the CD4 receptor, were cotransfected by electroporation (Burtey et al., 2007) with 10, 20 or 30 µg of the vector for expression of sdAb Nef19 (pcDNA-sdAb Nef19) and 5 µg of the vector for expression of the Nef-GFP fusion or of the GFP control protein. 24 h after transfection, the level of CD4 expression at the cell surface was analyzed on the cells expressing Nef-GFP or GFP by flow cytometry using a Cytomics FC500 instrument after labeling for 1 h at 4° C. with an anti-CD4 Ab directly coupled to phycoerythrin-CY5 (RPA-4, Beckton-Dickinson), and then fixing of the cells with a 3.7% formaldehyde solution.

Figure 6:
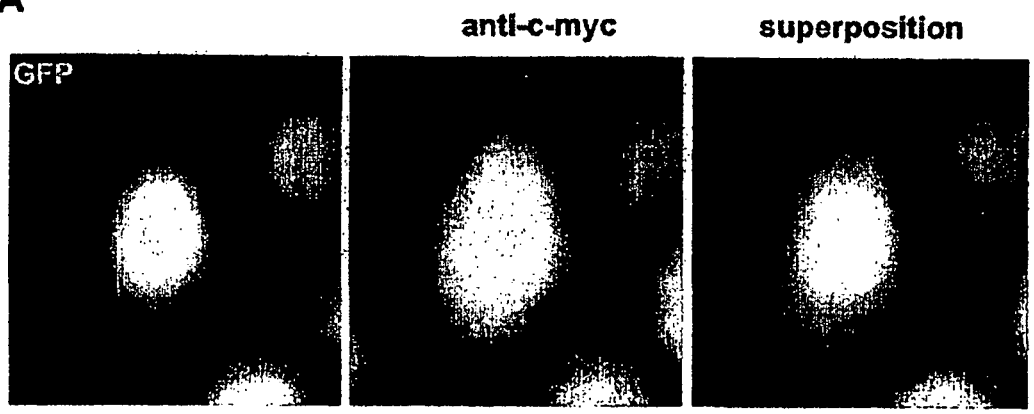
Figure 6:
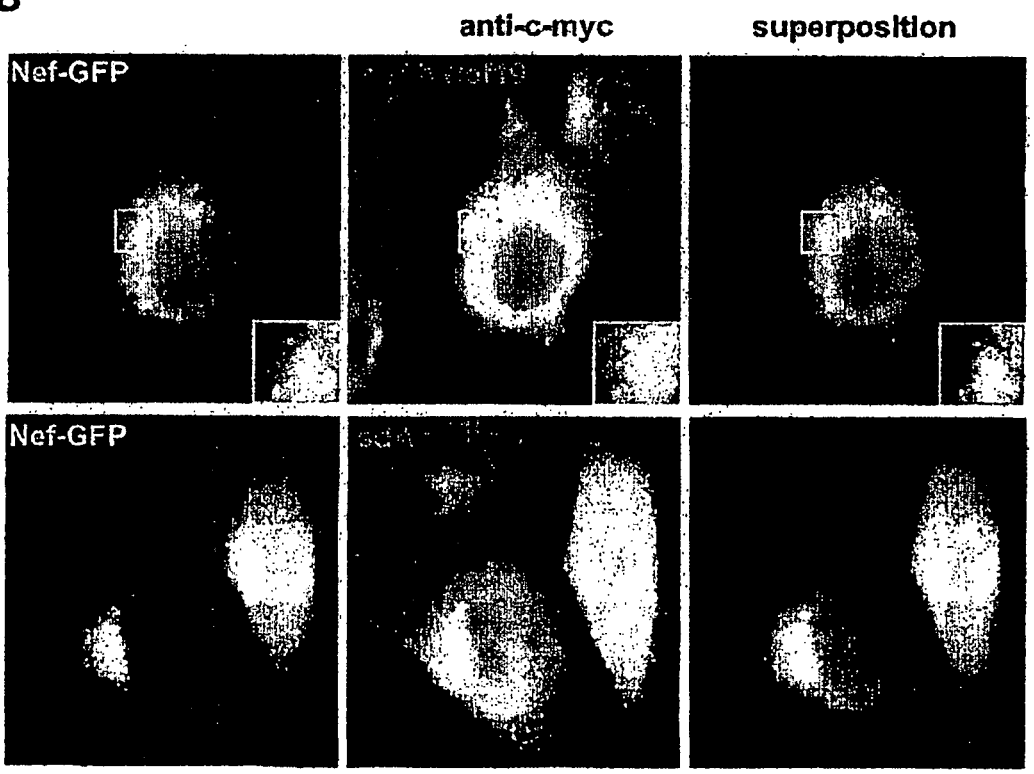

The results are illustrated in FIG. 6A. While a representative experiment is shown on the top panel, the bottom panel corresponds to the average of the results obtained from 3 independent experiments. In the absence of sdAb Nef19, Nef leads to a decrease of approximately 70% in the level of CD4 expression at the cell surface. The expression of increasing amounts of sdAb results in a dose-dependent reversion of this effect (black bars), since the level of CD4 present at the surface of the cells expressing Nef and transfected with 30 µg of the vector for expression of sdAb Nef19 is virtually comparable to that measured in the absence of Nef. The expression of the sdAb does not induce a nonspecific effect, since said expression, even at the highest dose, does not modify the level of CD4 present at the surface of the cells expressing the GFP control protein (white bars).

This inhibitory effect of sdAb Nef19 is also observed on nonlymphoid cells stably expressing the CD4 receptor. HeLa cells stably expressing CD4 (HeLa-CD4) were cotransfected as previously using the lipofection technique, with 1, 2 or 3 µg of the vector for expression of sdAb Nef19 and 1 µg of the vector expression of Nef-GFP or of the GFP control (Coleman et al., 2006). The level of CD4 surface expression was analyzed as previously by flow cytometry on the cells expressing Nef-GFP or GFP.

The results corresponding to the averages of 3 independent experiments are reported on FIG. 6B. They show that sdAb Nef19 is capable of inhibiting to a large extent the effect of the Nef-GFP fusion on the level of CD4 surface expression (black bars).

12—Study of the Inhibition by sdAb Nef19 of the Ability of Nef to Interact Directly with the Cellular Machinery of the Endocytosis Pathway The use, by several teams, of a CD8-Nef fusion protein in which the extracellular and membrane regions of CD8 are fused to the N-terminal end of Nef (CD8-Nef) has made it possible to show that the sequence of Nef contains determinants which allow it to interact directly with the machinery for vesicular transport of proteins in the endocytosis pathway. The CD8-Nef membrane chimera has, like the myristoylated native Nef protein, the property of modulating in trans the surface expression of the CD4 receptor, but also of modulating in cis its own level of expression at the cell surface, thus reflecting its ability to connect directly to the cellular machinery of the endocytosis pathway.

The inhibitory effect of sdAb Nef19 on the level of surface expression of the CD8-Nef chimera was therefore explored, by flow cytometry and by immunofluorescence, on HeLa cells.

For the cytometry analysis, the cells are cotransfected by lipofection with 1, 2 or 3 µg of the vector for expression of sdAb Nef19, 0.7 µg of the vector for expression of CD8-Nef or of the CD8-Stop control corresponding to the CD8 receptor devoid of cytoplasmic domain, and 0.3 µg of the vector for expression of GFP.

24 h after transfection, the cells are fixed for 20 min with a solution of PBS-4% PFA, and the level of expression of the CD8-Nef chimera at the surface of the cells expressing GFP was evaluated using an anti-CD8 Ab (SK1, Becton-Dickinson) coupled to phycoerythrin-Cy5.

For the immunofluorescence analysis, the cells were transfected with 1 µg of the vector for expression of CD8-Nef or CD8-Stop and 1 µg of the vector for expression of the sdAb. 24 h after transfection, the cells are fixed for 20 min with a solution of PBS-4% PFA and permeabilized with a solution of PBS-0.1% Triton X100. The sdAb was detected as previously (see FIG. 5), whereas the CD8-Nef fusion is detected with an anti-CD8 Ab coupled to FITC (SFCI, Coulter).

Figure 7:
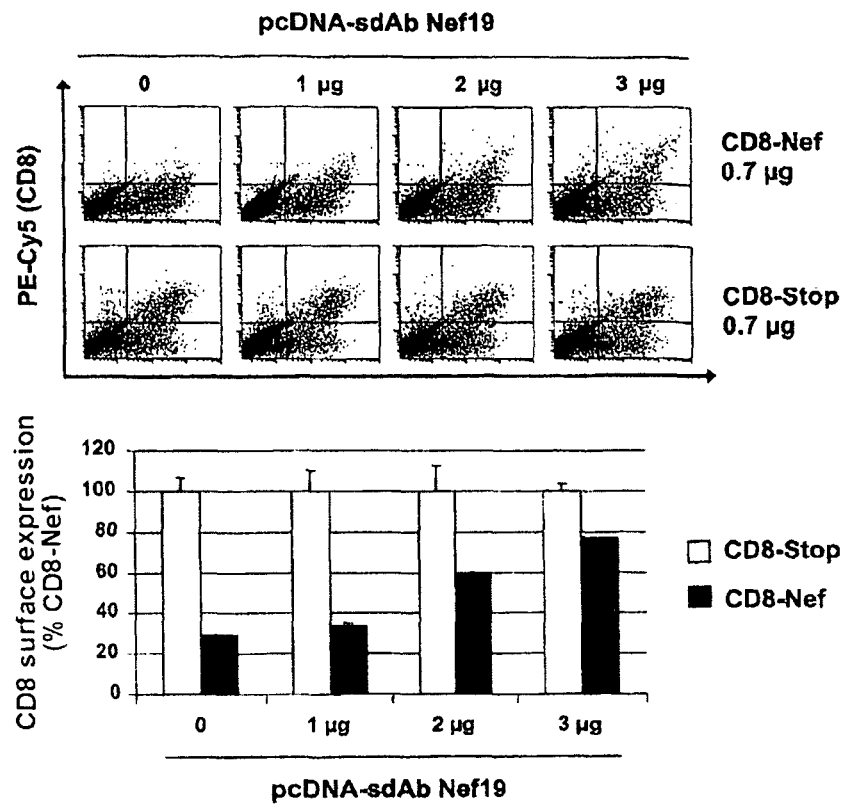
Figure 7:
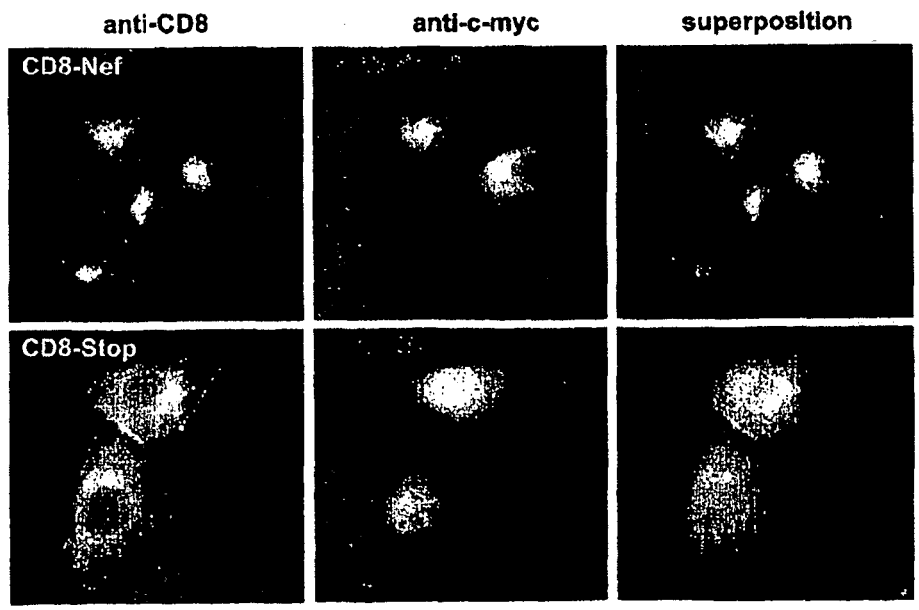

The results of these experiments are illustrated in FIG. 7. Part A corresponds to the results of the analysis by cytometry; the top panel represents a representative experiment while the bottom panel corresponds to the averages of 3 independent experiments. In the absence of sdAb Nef19, the level of expression of the CD8-Nef chimera is approximately five times lower than that of the control CD8-Stop protein (white bars). The expression of increasing amounts of the sdAb results in a gradual accumulation of the CD8-Nef protein at the cell surface (black bars). The expression of the sdAb has no effect on the level of expression of the CD8-Stop control (white bars).

The data from the immunofluorescence experiments reported on the top panels of FIG. 7B confirm these results, since a clear increase in labeling of the CD8-Nef protein at the plasma membrane is observed in the cells coexpressing sdAb Nef19 (indicated by arrows), whereas this labeling is almost exclusively concentrated in a perinuclear membrane compartment in the absence of the sdAb (cell indicated by an arrow head). As in FIG. 5, sdAb Nef19 is distributed diffusely between the cytoplasm and the nucleus in the control cells expressing the CD8-Stop protein (bottom panels), whereas it relocalizes to the intracellular membrane structures and at the plasma membrane that are also labeled with the anti-CD8 Ab in the cells expressing the CD8-Nef fusion (top panels).

The results of FIG. 7 confirm the recognition of Nef by sdAb Nef19 in the cell context; they also confirm the inhibitory effects of the sdAb on the interactions of Nef with the cellular machinery of the endocytosis pathway.

13—Interaction of sdAb Nef19 with the Nef Protein in the Cell Context

The direct recognition of Nef by sdAb Nef19 was explored at the cell level by means of coimmuno-precipitation experiments. 293T cells ($3\times10^6$) were cotransfected, by means of the calcium phosphate precipitation technique, with 5 µg of the vector for expression of the sdAb in combination with 5 µg of a vector for expression of the CD8-wild-type Nef fusion (CD8-Nef WT), or point mutants (CD8-NefLL164-165AA and CD8-NefE62-65A) or deletion mutants of Nef (CD8-Nef 1-61 and CD8-Nef 58-189). These constructs have been previously described (Janvier et al., 2003a,b; Madrid et al., 2005). The same type of experiment was also carried out on cells coexpressing the sdAb and the CD8 protein devoid of cytoplasmic domain (CD8-Stop) used as a control. 24 h after transfection, the cells were lyzed in a buffer containing 100 mM of $(NH_4)_2SO_4$, 20 mM of Tris (pH 7.5), 10% of glycerol, 1% of IGEPAL and a cocktail of protease inhibitors (Roche). The cell lyzate (600 µg of total proteins) was incubated for 1 h at 4° C. with 3 µg of the anti-CD8 Ab (32M4, Santa Cruz) and 30 µl of beads coated with protein A-sepharose. The immunoprecipitates were then analyzed by immunoblotting using an anti-CD8 Ab (H160, Santa Cruz) and an anti-c-myc Ab (9E10).

Figure 8:
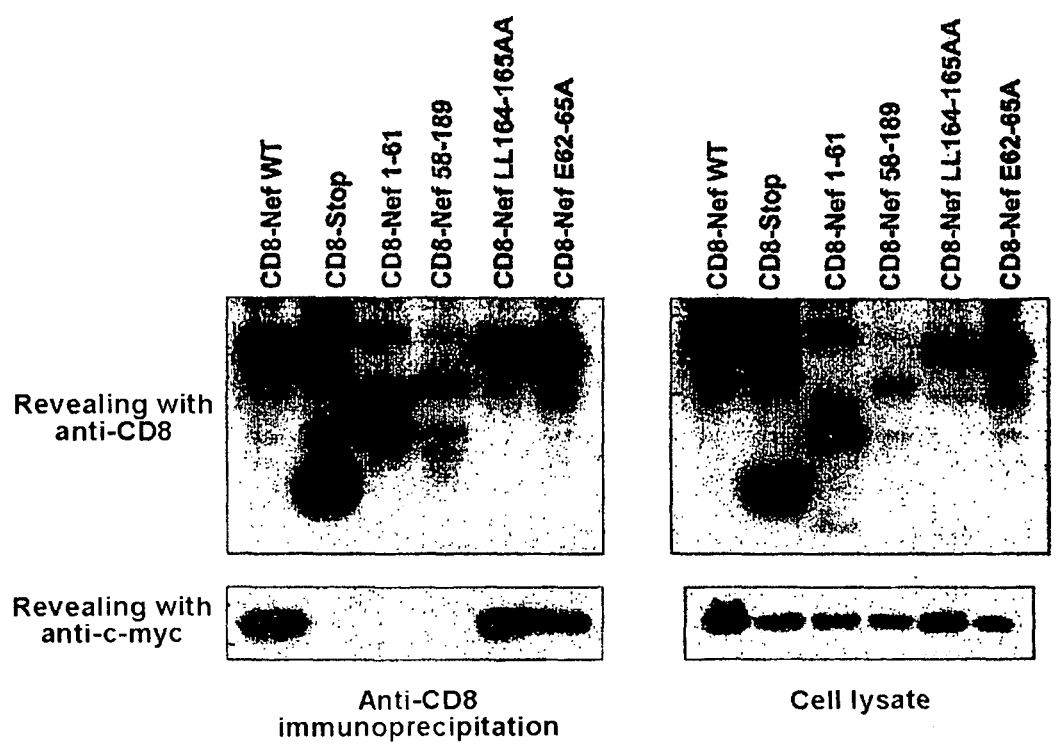

The results are illustrated in FIG. 8. As expected (left-hand panels), the band corresponding to sdAb Nef19 is specifically detected in the material immunoprecipitated from the cells expressing the CD8-Nef fusion protein, whereas it is not detected in the material immunoprecipitated from the cells expressing the control CD8-Stop protein. The analysis of the material immunoprecipitated from the cells expressing the mutated fusion proteins indicates that the sdAb is still capable of associating with the point mutants CD8-NefLL164-165AA and CD8-NefE62-65A, whereas the deletion mutants, CD8-Nef 1-61 and CD8-Nef 58-189, are not recognized by the sdAb. Since the immunogen used to generate sdAb Nef19 corresponded to a recombinant protein lacking the first 57 amino acids, the results of FIG. 8 suggest that the zone recognized by the sdAb is located at the C-terminal end of Nef, on a region between residues 190 and 206 of the protein.

14—Inhibition, by sdAb Nef19, of the Positive Effects of Nef on the Infectious Capacity of HIV The inhibitory activity of sdAb Nef19 on the contribution of Nef to the infectious properties of the viral particles was analyzed in an experimental system for evaluating the infectious capacity of HIV-1 during a single replication cycle (Madrid et al., 2005). Recombinant viral particles carrying the GFP reporter gene were produced by cotransfection of 293T cells as previously described (Basmaciogullari et al., 2006) with 8 µg of the vector for expression of the proteins derived from the gag and pol genes of HIV-1 (NL43 isolate) (Owens et al., 2003), 8 µg of the vector for expression of the GFP transgene, 2 µg of the vector for expression of the envelope of HIV-1 (89.6 isolate) or of VSV (VSV-G), 1 µg of the vector for expression of the Nef protein tagged at its C-terminal end with the HA epitope (Dorfman et al., 2002), and 8 µg of the vector for expression of the sdAb. The viral particles pseudotyped with the HIV-1 envelope or the VSV envelope were recovered in the culture supernatant 48 h after transfection and stored at −80° C. The virus stocks were titered by measuring reverse transcriptase (RT) activity, and then used to infect HeLa-CD4 cells or T cells of the HPB-ALL line. 3×10$^4$ HeLa-CD4 cells were infected in 24-well plates with 500 it of a dilution of 5×10$^5$ and 5×10$^4$ arbitrary units of RT/ml, of the virus stocks pseudotyped, respectively, with the HIV-1 or VSV envelope. In the case of the HPB-ALL line, 10$^5$ cells were infected with 1 ml of a dilution to 17×10$^4$ and 17×10$^3$ arbitrary units of RT/ml, of the virus stocks pseudotyped, respectively, with the HIV-1 or VSV envelope. 60 h after infection, the cells were recovered and fixed in a solution of PBS-3.7% formaldehyde, and then the percentage of cells infected, and therefore expressing GFP, is evaluated by flow cytometry.

Figure 9:
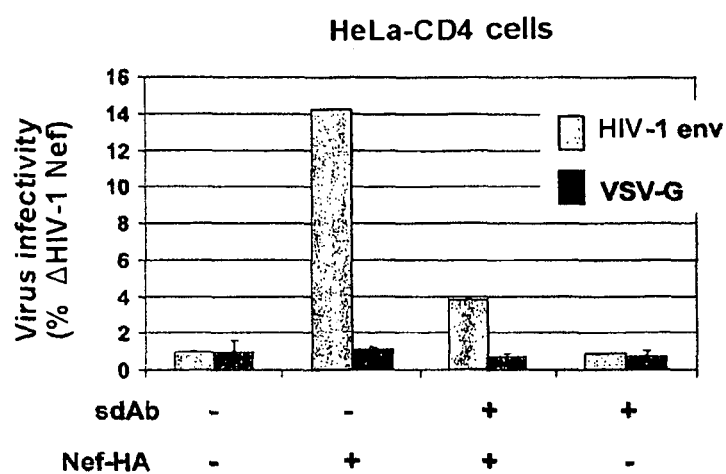
Figure 9:
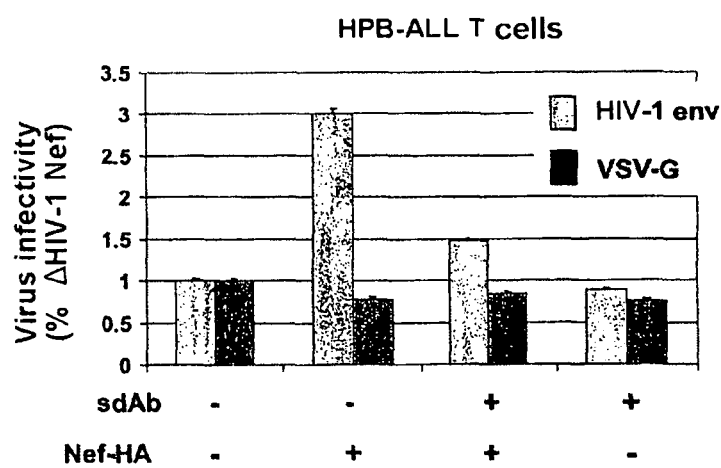

The results corresponding to the averages of 3 independent experiments are reported in FIG. 9. The top panel (A) corresponds to the infectious capacity of the viral particles, measured on HeLa-CD4 cells, and the bottom panel (B) corresponds to the infectious capacity measured on HPB-ALL T cells. The results are reported as a function of the infectious capacity of the viral particles pseudotyped with the HIV-1 envelope (blue bars) or the VSV envelope (maroon bars) and produced in the absence of Nef. As expected, Nef expression in the producer cells results in a clear increase in the infectious capacity of the viral particles expressing the HIV-1 envelope (14 times and 3 times, respectively, in the HeLa-CD4 and HPB-ALL cells), whereas the viruses expressing the VSV envelope are not influenced by the expression of Nef. The expression of sdAb Nef19 causes a significant and specific inhibition, of the order of 75%, of the effect of Nef on the infectious capacity of the viral particles, independently of the cell type used. Conversely, the expression of the sdAb does not influence the infectious capacity of the viral particles expressing the VSV G protein, whether the particles are produced in the absence or in the presence of Nef.

15—Incorporation of sdAb Nef19 into the Viral Particles

Since several studies had shown that the Nef protein of HIV-1 was incorporated into the viral particles budding at the surface of the infected cells, the influence of the expression of sdAb Nef19 in the producer cells, on the incorporation of Nef into the viral particles, was therefore explored. The viral particles were produced as previously (see FIG. 9) in 293T cells cotransfected with 1 or 4 μg of the vector for expression of sdAb Nef19. The culture supernatants were subjected to ultracentrifugation at 27 000 rpm for 1 h 30 at 4° C. on a PBS/sucrose cushion. The viral particles thus purified were then taken up in Laemli buffer and analyzed by immunoblotting using anti-HA (3F10, Roche), anti-c-myc (9E10, Roche) and anti-p24 (obtained from the "NIH AIDS Research and Reference Reagent Program") antibodies; the lysates of the producer cells were also analyzed by immunoblotting.

The results are illustrated in FIG. 10A. The left-hand panels correspond to the analysis of the cell lysates, whereas the right-hand panels correspond to the analysis of the purified viruses. In the absence of sdAb Nef19, the Nef-HA protein is correctly incorporated into the viral particles, as indicated by the detection of the 2 bands revealed with the anti-HA Ab (top panel), corresponding to the whole protein of 27 kDa and to the cleavage product of approximately 25 kDa (Chen et al., 1998; Welker et al., 1998). The incorporation of Nef does not appear to be disrupted by the expression of the sdAb, but the latter is also incorporated only when the viral particles have been produced from cells expressing Nef. These results show that the sdAb is specifically recruited into the infectious viral particles, probably by direct interaction with the Nef protein established in the producer cell. This recruitment of the sdAb could be responsible for its inhibitory effect on the infectious capacities of the viral particles produced.

In order to confirm that the incorporation of sdAb Nef19 into the viral particles is indeed the result of association with the Nef protein in the producer cells, the ability of the sdAb to interact with the Nef-HA protein was explored as previously by coimmunoprecipitation from 293T cells cotransfected with the vectors for, respectively, the expression of the sdAb and of Nef-HA. 600 μg of proteins derived from the soluble fraction of the cell lysates were incubated for 1 h at 4° C. with 3 μg of the anti-HA Ab (3F10) and 30 μl of beads coated with protein A-sepharose. The immunoprecipitated material was then analyzed by immunoblotting using an Ab specifically directed against the Nef protein (Ab a56 obtained from the "NIH AIDS Research and Reference Reagent Program") and the anti-c-myc Ab (9E10).

Figure 10:
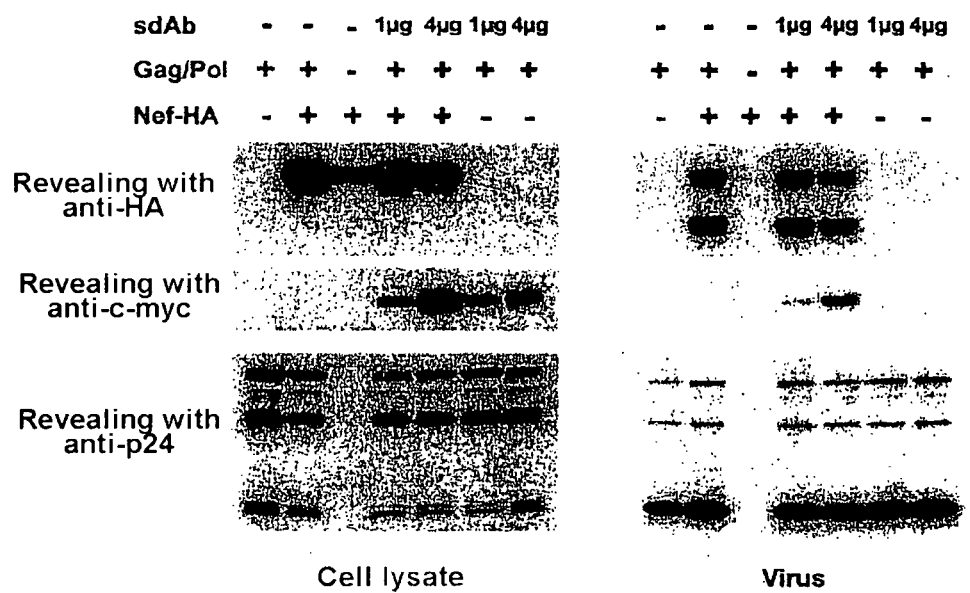
Figure 10:
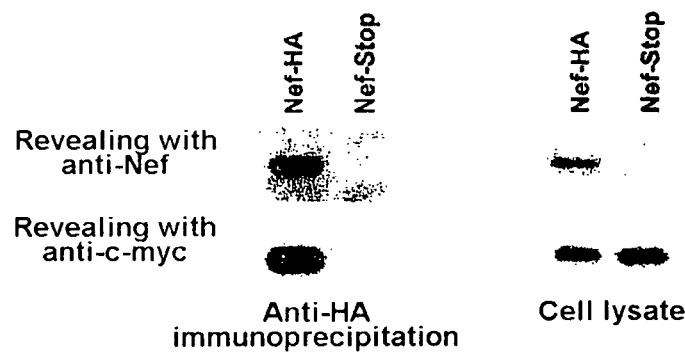

As shown by the results reported in part B of FIG. 10, the sdAb is detected only in the immunoprecipitate of the cells expressing Nef-HA, but is not detected in the material precipitated from the cells transfected with the Nef-Stop control vector (left-hand panels) enabling the expression of a polypeptide corresponding to the first 46 residues of the Nef protein, even though the sdAb is clearly expressed in these cells (right-hand panels).

LITERATURE REFERENCES 1. (Hamers-Casterman et al., 1993)
2. (Hoogenboom et al., 1991)
3. (Chomczynski and Sacchi, 1987)
4. (Arbabi Ghahroudi et al., 1997)
5. (Smith, 1985; Hoogenboom et al., 1991)
6. (Lefranc, 2003)
7. (Janvier et al., 2003a,b; Madrid et al., 2005)
8. (Chen et al., 1998; Welker et al., 1998)

The invention claimed is:

1. A single-domain antibody (sdAb), comprising the amino acid sequence selected from the group consisting of SEQ ID NO: 7 to SEQ ID NO: 12.

2. The sdAb of claim 1, wherein the amino acid sequence is encoded by a nucleotide sequence selected from the group consisting of SEQ ID NO: 1 to SEQ ID NO: 6.

3. A method for producing the sdAbs of claim 1, comprising the following steps:
   immunizing camelids with an immunogenic composition comprising recombinant purified HIV-1 Nef;
   isolating peripheral blood mononuclear cells (PBMCs) from the blood of said camelid;
   preparing a VHH phagemid library from total RNA isolated from said PBMCs;
   selecting for phage clones encoding Nef-specific sdAbs using biotinylated recombinant Nef;
   amplifying said clones using suitable primers and PCR; and
   inserting said amplified product into a suitable expression vector.

4. The method of claim 3, wherein said HIV-1 Nef lacks the first 56 amino acids.

5. The method of claim 3, wherein the VHH phagemid library preparation comprises the following steps:
   preparing cDNA from the isolated PBMC total RNA;
   PCR amplifying VHH gene fragments from said cDNA to create a VHH library; and
   purifying the resulting VHH fragments and ligating them into a suitable phagemid.

6. The method of claim 3, further comprising isolating the sdAbs by phage display technique and purifying.

7. A pharmaceutical composition, comprising at least one sdAb according to claim 1, and a pharmaceutically acceptable carrier.

8. The pharmaceutical composition of claim 7, wherein the sdAb is configured to allow the sdAb to cross the cell membrane and to be released within a cell.

9. The pharmaceutical composition of claim 8, wherein the sdAb is conjugated to a peptide, or the sdAb is combined with a lipid compound.

10. The sdAb of claim 1, consisting of the amino acid sequence selected from the group consisting of SEQ ID NO: 7 to SEQ ID NO: 12.

* * * * *